(12) United States Patent
Muramatsu et al.

(10) Patent No.: US 8,980,615 B2
(45) Date of Patent: Mar. 17, 2015

(54) RECOMBINANT MICROORGANISM AND METHOD FOR PRODUCING ALIPHATIC POLYESTER USING THE SAME

(75) Inventors: Masayoshi Muramatsu, Miyoshi (JP); Hiromi Kambe, Seto (JP); Masakazu Ito, Toyota (JP); Takashi Shimamura, Toyota (JP); Katsunori Kohda, Nisshin (JP)

(73) Assignee: Toyota Jidosha Kabushiki Kaisha, Aichi (JP)

( * ) Notice: Subject to any disclaimer, the term of this patent is extended or adjusted under 35 U.S.C. 154(b) by 157 days.

(21) Appl. No.: 13/636,830

(22) PCT Filed: Mar. 24, 2011

(86) PCT No.: PCT/JP2011/057077
§ 371 (c)(1),
(2), (4) Date: Nov. 1, 2012

(87) PCT Pub. No.: WO2011/118671
PCT Pub. Date: Sep. 29, 2011

(65) Prior Publication Data
US 2013/0045516 A1 Feb. 21, 2013

(30) Foreign Application Priority Data
Mar. 25, 2010 (JP) ................... 2010-069688

(51) Int. Cl.
C12N 1/20 (2006.01)
C12P 7/62 (2006.01)
C12N 9/10 (2006.01)

(52) U.S. Cl.
CPC .............. *C12P 7/625* (2013.01); *C12N 9/1029* (2013.01); *C12Y 203/01* (2013.01); *C12Y 208/03001* (2013.01); *C12N 9/13* (2013.01)
USPC .................. 435/252.3; 435/135; 435/193

(58) Field of Classification Search
CPC ................ C12P 7/62; C12N 9/1029
USPC .................. 435/135, 193, 252.3, 320.1
See application file for complete search history.

(56) References Cited

U.S. PATENT DOCUMENTS

| 8,748,137 B2 * | 6/2014 | Obata et al. ............... 435/135 |
| 2005/0227340 A1 | 10/2005 | Kim et al. |
| 2011/0008855 A1 | 1/2011 | Park et al. |
| 2011/0183388 A1 | 7/2011 | Sabirova et al. |

FOREIGN PATENT DOCUMENTS

| EP | 2471910 A2 | 7/2012 |
| JP | 3536050 B2 | 3/2004 |
| JP | 2005-295993 A | 10/2005 |
| JP | 2009-504146 A | 2/2009 |
| JP | 2011-024503 A | 2/2011 |
| KP | 2009-0026035 A | 3/2009 |
| WO | 2006/126796 A1 | 11/2006 |
| WO | 2008/062999 A1 | 5/2008 |
| WO | 2009/031762 A2 | 3/2009 |
| WO | 2009/091141 A2 | 7/2009 |
| WO | 2011/013352 A1 | 2/2011 |

OTHER PUBLICATIONS

International Preliminary Report on Patentability (English Translation)—Jun. 6, 2012 (date of completion).*
Taguchi, et al., "A microbial factory for lactate-based polyesters using a lactate-polymerizing enzyme", XP008143036, PNAS, Nov. 11, 2008, vol. 105, No. 45, p. 17323-17327.
Yang, et al., "Biosynthesis of Polylactic Acid and Its Copolymers Using Evolved Propionate CoA Transferase and PHA Synthase", XP-002583390, Biotechnology and Bioengineering, vol. 105, No. 1, Jan. 1, 2010, pp. 150-160.
Jung, et al., "Metabolic Engineering of *Escherichia coli* for the Production of Polylactic Acid and Its Copolymers", XP 055032360, Biotechnology and Bioengineering, vol. 105, No. 1, Jan. 1, 2010, pp. 161-171.
Jung, et al., "Spontaneous liberation of intracellular polyhydroxybutyrate granules in *Escherichia coli*", XP027793207, Research in Microbiology, vol. 156, No. 8, Sep. 1, 2005, pp. 865-873.
Sabirova, et al., "Mutation in a "tesB-Like" Hydroxyacyl-Coenzyme A-Specific Thioesterase Gene Causes Hyperproduction of Extracellular Polyhydroxyalkanoates by Alcanivorax borkumensis SK2", XP055090930, Journal of Bacteriology, vol. 188, No. 24, Sep. 22, 2006, pp. 8452-8459.
Cetin, et al., "Poly-beta-hydroxybutyrate accumulation and releasing by hydrogen producing bacteria, Rhodobacter sphaeroides O.U.001. A transmission electron microscopic study", XP002720116, African Journal of Biotechnology, vol. 5, No. 22, Nov. 2006, pp. 2069-2072.
Yang, et al., "Tailor-made type II Pseudomonas PHA synthases and their use for the biosynthesis of polylactic acid and its copolymer in recombinant *Escherichia coli*", XP055051491, Applied Microbiology and Biotechnology, vol. 90, No. 2, Apr. 1, 2011, pp. 603-614.
Seiichi Taguchi, et al., "A microbial factory for lactate-based polyesters using a lactate-polymerizing enzyme", Proc. Natl. Acad. Sci., 2008, pp. 17323-17327, vol. 105, No. 45.

* cited by examiner

*Primary Examiner* — Tekchand Saidha
(74) *Attorney, Agent, or Firm* — Sughrue Mion, PLLC

(57) ABSTRACT

Aliphatic polyester productivity is improved for production of aliphatic polyester using a recombinant microorganism. A recombinant microorganism prepared by introducing a gene encoding a protein having activity of converting lactic acid to lactic-acid CoA and a gene encoding a protein having activity of synthesizing polyhydroxyalkanoate using hydroxyacyl CoA as a substrate into a host microorganism is cultured and then aliphatic polyester is recovered from the medium.

2 Claims, 13 Drawing Sheets

SEQUENCE LISTING

<160> NUMBER OF SEQ ID NOS: 94

<210> SEQ ID NO 1
<211> LENGTH: 1554
<212> TYPE: DNA
<213> ORGANISM: Megasphaera elsdenii

```
<220> FEATURE:
<221> NAME/KEY: CDS
<222> LOCATION: (1)..(1554)

<400> SEQUENCE: 1 atg aga aaa gta gaa atc att aca gct gaa caa gca gct cag ctc gta      48
Met Arg Lys Val Glu Ile Ile Thr Ala Glu Gln Ala Ala Gln Leu Val
1               5                   10                  15 aaa gac aac gac acg att acg tct atc ggc ttt gtc agc agc gcc cat      96
Lys Asp Asn Asp Thr Ile Thr Ser Ile Gly Phe Val Ser Ser Ala His
            20                  25                  30 ccg gaa gca ctg acc aaa gct ttg gaa aaa cgg ttc ctg gac acg aac     144
Pro Glu Ala Leu Thr Lys Ala Leu Glu Lys Arg Phe Leu Asp Thr Asn
        35                  40                  45 acc ccg cag aac ttg acc tac atc tat gca ggc tct cag ggt aaa cgc     192
Thr Pro Gln Asn Leu Thr Tyr Ile Tyr Ala Gly Ser Gln Gly Lys Arg
50                  55                  60 gat ggc cgt gcc gct gaa cat ctg gca cac aca ggc ctt ttg aaa cgc     240
Asp Gly Arg Ala Ala Glu His Leu Ala His Thr Gly Leu Leu Lys Arg
65                  70                  75                  80 gcc atc atc ggt cac tgg cag act gta ccg gct atc ggt aaa ctg gct     288
Ala Ile Ile Gly His Trp Gln Thr Val Pro Ala Ile Gly Lys Leu Ala
                85                  90                  95 gtc gaa aac aag att gaa gct tac aac ttc tcg cag ggc acg ttg gtc     336
Val Glu Asn Lys Ile Glu Ala Tyr Asn Phe Ser Gln Gly Thr Leu Val
            100                 105                 110 cac tgg ttc cgc gcc ttg gca ggt cat aag ctc ggc gtc ttc acc gac     384
His Trp Phe Arg Ala Leu Ala Gly His Lys Leu Gly Val Phe Thr Asp
        115                 120                 125 atc ggt ctg gaa act ttc ctc gat ccc cgt cag ctc ggc ggc aag ctc     432
Ile Gly Leu Glu Thr Phe Leu Asp Pro Arg Gln Leu Gly Gly Lys Leu
130                 135                 140 aat gac gta acc aaa gaa gac ctc gtc aaa ctg atc gaa gtc gat ggt     480
Asn Asp Val Thr Lys Glu Asp Leu Val Lys Leu Ile Glu Val Asp Gly
145                 150                 155                 160 cat gaa cag ctt ttc tac ccg acc ttc ccg gtc aac gta gct ttc ctc     528
His Glu Gln Leu Phe Tyr Pro Thr Phe Pro Val Asn Val Ala Phe Leu
                165                 170                 175 cgc ggt acg tat gct gat gaa tcc ggc aat atc acc atg gac gaa gaa     576
Arg Gly Thr Tyr Ala Asp Glu Ser Gly Asn Ile Thr Met Asp Glu Glu
            180                 185                 190 atc ggg cct ttc gaa agc act tcc gta gcc cag gcc gtt cac aac tgt     624
Ile Gly Pro Phe Glu Ser Thr Ser Val Ala Gln Ala Val His Asn Cys
        195                 200                 205 ggc ggt aaa gtc gtc gtc cag gtc aaa gac gtc gtc gct cac ggc agc     672
Gly Gly Lys Val Val Val Gln Val Lys Asp Val Val Ala His Gly Ser
210                 215                 220 ctg gat ccg cgc atg gtc aaa atc cct ggc atc tat gtc gac tat gtt     720
Leu Asp Pro Arg Met Val Lys Ile Pro Gly Ile Tyr Val Asp Tyr Val
225                 230                 235                 240 gtc gta gct gct ccg gaa gac cat cag cag act tat gac tgc gaa tat     768
Val Val Ala Ala Pro Glu Asp His Gln Gln Thr Tyr Asp Cys Glu Tyr
                245                 250                 255 gat ccg tcc ctt agc ggc gaa cat cgt gct cct gaa ggc gct gct gac     816
Asp Pro Ser Leu Ser Gly Glu His Arg Ala Pro Glu Gly Ala Ala Asp
            260                 265                 270 gca gct ctc ccc atg agc gct aag aaa atc atc ggc cgc cgc ggt gct     864
Ala Ala Leu Pro Met Ser Ala Lys Lys Ile Ile Gly Arg Arg Gly Ala
        275                 280                 285
```

| | | |
|---|---|---|
| ttg gaa ttg acc gaa aac gct gtc gtc aac ctc ggc gtc ggc gct ccg<br>Leu Glu Leu Thr Glu Asn Ala Val Val Asn Leu Gly Val Gly Ala Pro<br>290                       295                           300 | 912 |
| gaa tac gtt gct tcc gtt gcc ggt gaa gaa ggt atc gct gat acc att<br>Glu Tyr Val Ala Ser Val Ala Gly Glu Glu Gly Ile Ala Asp Thr Ile<br>305                       310                       315                320 | 960 |
| acc ttg acc gtc gaa ggt ggc gct atc ggt ggt gta ccg cag ggc ggt<br>Thr Leu Thr Val Glu Gly Gly Ala Ile Gly Gly Val Pro Gln Gly Gly<br>                       325                       330                       335 | 1008 |
| gcc cgc ttc ggt tcg tcc cgt aat gct gat gcc atc atc gac cat act<br>Ala Arg Phe Gly Ser Ser Arg Asn Ala Asp Ala Ile Ile Asp His Thr<br>         340                       345                       350 | 1056 |
| tac cag ttc gac ttc tat gat ggc ggt ctg gac atc gct tac ctc<br>Tyr Gln Phe Asp Phe Tyr Asp Gly Gly Leu Asp Ile Ala Tyr Leu<br>             355                     360                    365 | 1104 |
| ggc ctg gct cag tgc gat ggt tcg ggc aac atc aac gtc agc aag ttc<br>Gly Leu Ala Gln Cys Asp Gly Ser Gly Asn Ile Asn Val Ser Lys Phe<br>     370                   375                       380 | 1152 |
| ggt act aac gtt gcc ggc tgt ggc ggt ttc ccc aac att tcc cag cag<br>Gly Thr Asn Val Ala Gly Cys Gly Gly Phe Pro Asn Ile Ser Gln Gln<br>385                       390                       395                400 | 1200 |
| aca ccg aat gtt tac ttc tgc ggc acc ttc acg gct ggc ggc ttg aaa<br>Thr Pro Asn Val Tyr Phe Cys Gly Thr Phe Thr Ala Gly Gly Leu Lys<br>                   405                       410                    415 | 1248 |
| atc gct gtc gaa gac ggc aaa gtc aag atc ctc cag gaa ggc aaa gcc<br>Ile Ala Val Glu Asp Gly Lys Val Lys Ile Leu Gln Glu Gly Lys Ala<br>         420                       425                       430 | 1296 |
| aag aag ttc atc aaa gct gtc gac cag atc act ttc aac ggt tct tat<br>Lys Lys Phe Ile Lys Ala Val Asp Gln Ile Thr Phe Asn Gly Ser Tyr<br>             435                       440                    445 | 1344 |
| gca gcc cgc aac ggc aaa cat gtt ctc tac atc acg gaa cgc tgc gta<br>Ala Ala Arg Asn Gly Lys His Val Leu Tyr Ile Thr Glu Arg Cys Val<br>450                       455                       460 | 1392 |
| ttt gaa ctg acc aaa gaa ggc ttg aaa ctc atc gaa gtc gca ccg ggc<br>Phe Glu Leu Thr Lys Glu Gly Leu Lys Leu Ile Glu Val Ala Pro Gly<br>465                       470                       475                480 | 1440 |
| atc gat att gaa aaa gat atc ctc gct cac atg gac ttc aag ccg atc<br>Ile Asp Ile Glu Lys Asp Ile Leu Ala His Met Asp Phe Lys Pro Ile<br>                   485                       490                    495 | 1488 |
| att gat aat ccg aaa ctc atg gat gcc cgc ctc ttc cag gac ggt ccc<br>Ile Asp Asn Pro Lys Leu Met Asp Ala Arg Leu Phe Gln Asp Gly Pro<br>             500                       505                    510 | 1536 |
| atg gga ctg aaa aaa taa<br>Met Gly Leu Lys Lys<br>             515 | 1554 |

<210> SEQ ID NO 2
<211> LENGTH: 517
<212> TYPE: PRT
<213> ORGANISM: Megasphaera elsdenii

<400> SEQUENCE: 2

Met Arg Lys Val Glu Ile Ile Thr Ala Glu Gln Ala Ala Gln Leu Val
1               5                   10                 15

Lys Asp Asn Asp Thr Ile Thr Ser Ile Gly Phe Val Ser Ser Ala His
               20                   25                   30

Pro Glu Ala Leu Thr Lys Ala Leu Glu Lys Arg Phe Leu Asp Thr Asn
                   35                   40                   45

Thr Pro Gln Asn Leu Thr Tyr Ile Tyr Ala Gly Ser Gln Gly Lys Arg
 50                    55                   60

```
Asp Gly Arg Ala Ala Glu His Leu Ala His Thr Gly Leu Leu Lys Arg
 65                  70                  75                  80

Ala Ile Ile Gly His Trp Gln Thr Val Pro Ala Ile Gly Lys Leu Ala
                 85                  90                  95

Val Glu Asn Lys Ile Glu Ala Tyr Asn Phe Ser Gln Gly Thr Leu Val
            100                 105                 110

His Trp Phe Arg Ala Leu Ala Gly His Lys Leu Gly Val Phe Thr Asp
        115                 120                 125

Ile Gly Leu Glu Thr Phe Leu Asp Pro Arg Gln Leu Gly Gly Lys Leu
    130                 135                 140

Asn Asp Val Thr Lys Glu Asp Leu Val Lys Leu Ile Glu Val Asp Gly
145                 150                 155                 160

His Glu Gln Leu Phe Tyr Pro Thr Phe Pro Val Asn Val Ala Phe Leu
                165                 170                 175

Arg Gly Thr Tyr Ala Asp Glu Ser Gly Asn Ile Thr Met Asp Glu Glu
            180                 185                 190

Ile Gly Pro Phe Glu Ser Thr Ser Val Ala Gln Ala Val His Asn Cys
        195                 200                 205

Gly Gly Lys Val Val Gln Val Lys Asp Val Ala His Gly Ser
    210                 215                 220

Leu Asp Pro Arg Met Val Lys Ile Pro Gly Ile Tyr Val Asp Tyr Val
225                 230                 235                 240

Val Val Ala Ala Pro Glu Asp His Gln Gln Thr Tyr Asp Cys Glu Tyr
                245                 250                 255

Asp Pro Ser Leu Ser Gly Glu His Arg Ala Pro Glu Gly Ala Ala Asp
            260                 265                 270

Ala Ala Leu Pro Met Ser Ala Lys Ile Ile Gly Arg Arg Gly Ala
        275                 280                 285

Leu Glu Leu Thr Glu Asn Ala Val Val Asn Leu Gly Val Gly Ala Pro
    290                 295                 300

Glu Tyr Val Ala Ser Val Ala Gly Glu Glu Gly Ile Ala Asp Thr Ile
305                 310                 315                 320

Thr Leu Thr Val Glu Gly Gly Ala Ile Gly Gly Val Pro Gln Gly Gly
                325                 330                 335

Ala Arg Phe Gly Ser Ser Arg Asn Ala Asp Ala Ile Ile Asp His Thr
            340                 345                 350

Tyr Gln Phe Asp Phe Tyr Asp Gly Gly Leu Asp Ile Ala Tyr Leu
        355                 360                 365

Gly Leu Ala Gln Cys Asp Gly Ser Gly Asn Ile Asn Val Ser Lys Phe
    370                 375                 380

Gly Thr Asn Val Ala Gly Cys Gly Gly Phe Pro Asn Ile Ser Gln Gln
385                 390                 395                 400

Thr Pro Asn Val Tyr Phe Cys Gly Thr Phe Thr Ala Gly Gly Leu Lys
                405                 410                 415

Ile Ala Val Glu Asp Gly Lys Val Lys Ile Leu Gln Glu Gly Lys Ala
            420                 425                 430

Lys Lys Phe Ile Lys Ala Val Asp Gln Ile Thr Phe Asn Gly Ser Tyr
        435                 440                 445

Ala Ala Arg Asn Gly Lys His Val Leu Tyr Ile Thr Glu Arg Cys Val
    450                 455                 460

Phe Glu Leu Thr Lys Glu Gly Leu Lys Leu Ile Glu Val Ala Pro Gly
465                 470                 475                 480
```

```
Ile Asp Ile Glu Lys Asp Ile Leu Ala His Met Asp Phe Lys Pro Ile
            485                 490                 495
Ile Asp Asn Pro Lys Leu Met Asp Ala Arg Leu Phe Gln Asp Gly Pro
        500                 505                 510
Met Gly Leu Lys Lys
        515

<210> SEQ ID NO 3
<211> LENGTH: 1563
<212> TYPE: DNA
<213> ORGANISM: Staphylococcus aureus
<220> FEATURE:
<221> NAME/KEY: CDS
<222> LOCATION: (1)..(1563)

<400> SEQUENCE: 3 ttg aaa caa atc aca tgg cac gac tta caa cat atc att aaa gat ggt       48
Leu Lys Gln Ile Thr Trp His Asp Leu Gln His Ile Ile Lys Asp Gly
1               5                   10                  15 gat gtg att ggt tta cca gca tta gct gta gcc aac tta ccc gcc gaa       96
Asp Val Ile Gly Leu Pro Ala Leu Ala Val Ala Asn Leu Pro Ala Glu
                20                  25                  30 gtt cta cgt gct gtg tta gcg caa cat gac aca tat cat acg ccc aaa      144
Val Leu Arg Ala Val Leu Ala Gln His Asp Thr Tyr His Thr Pro Lys
            35                  40                  45 gat tta acg ttt ata tta gcg aat gat atc cat agt tta ggt gcc gca      192
Asp Leu Thr Phe Ile Leu Ala Asn Asp Ile His Ser Leu Gly Ala Ala
        50                  55                  60 ccg gat tta gat gat ttt ata gaa cgt cgc atg att aaa cgt gtc att      240
Pro Asp Leu Asp Asp Phe Ile Glu Arg Arg Met Ile Lys Arg Val Ile
65                  70                  75                  80 atg agc att tta acg gct tct tcc aaa acg gca caa gca atg aaa aat      288
Met Ser Ile Leu Thr Ala Ser Ser Lys Thr Ala Gln Ala Met Lys Asn
                85                  90                  95 aat gac att gaa gct tat ttt tta cca caa ggt atc att gca act cat      336
Asn Asp Ile Glu Ala Tyr Phe Leu Pro Gln Gly Ile Ile Ala Thr His
                100                 105                 110 tat cgt cag agt aat caa tta tta cct gga gtt att act aaa atc gga      384
Tyr Arg Gln Ser Asn Gln Leu Leu Pro Gly Val Ile Thr Lys Ile Gly
            115                 120                 125 tta aac aca gct gtt gat cct aga tac ggt ggc ggt aaa gta aat aca      432
Leu Asn Thr Ala Val Asp Pro Arg Tyr Gly Gly Gly Lys Val Asn Thr
        130                 135                 140 cga aca act gat gat tta gtt tca tta gta acc atc aac gat gaa aca      480
Arg Thr Thr Asp Asp Leu Val Ser Leu Val Thr Ile Asn Asp Glu Thr
145                 150                 155                 160 tac tta cat tac aca ttc cct agc gtt gat gtg gca cta ctg aga gga      528
Tyr Leu His Tyr Thr Phe Pro Ser Val Asp Val Ala Leu Leu Arg Gly
                165                 170                 175 aca tac gca gat caa caa ggt aac att tat tta act caa gaa gcg tac      576
Thr Tyr Ala Asp Gln Gln Gly Asn Ile Tyr Leu Thr Gln Glu Ala Tyr
            180                 185                 190 ttg agc gag tgt tat cat gtc gca tta aac gcg aaa gcc aat cat ggg      624
Leu Ser Glu Cys Tyr His Val Ala Leu Asn Ala Lys Ala Asn His Gly
        195                 200                 205 aaa gtt att gta caa gtt aaa gct tta gtt gat gga tat caa cta aaa      672
Lys Val Ile Val Gln Val Lys Ala Leu Val Asp Gly Tyr Gln Leu Lys
    210                 215                 220 ccg aat gaa gtt gtt atc cca gga aat ctt gtc gat tat gta tac gtc      720
Pro Asn Glu Val Val Ile Pro Gly Asn Leu Val Asp Tyr Val Tyr Val
225                 230                 235                 240
```

```
aca gaa gat gaa aag aat cac cgc caa gta att cag agt cat tat tta      768
Thr Glu Asp Glu Lys Asn His Arg Gln Val Ile Gln Ser His Tyr Leu
            245                 250                 255 cca gcc ttg tct gga gaa gaa cga att gat gga ata cct gaa ccc gca      816
Pro Ala Leu Ser Gly Glu Glu Arg Ile Asp Gly Ile Pro Glu Pro Ala
        260                 265                 270 tta cct ttt aat agt cgc aaa ttg att ctc cga cgt gct gct cag ttt      864
Leu Pro Phe Asn Ser Arg Lys Leu Ile Leu Arg Arg Ala Ala Gln Phe
    275                 280                 285 tta act tat ggc gat aca att agc atc ggt tat ggc atc aat aat gaa      912
Leu Thr Tyr Gly Asp Thr Ile Ser Ile Gly Tyr Gly Ile Asn Asn Glu
290                 295                 300 ctc tct aat tta ttg cac gaa gaa tgt gtt gaa cat gat gtg caa ccg      960
Leu Ser Asn Leu Leu His Glu Glu Cys Val Glu His Asp Val Gln Pro
305                 310                 315                 320 att tta gat gtt ggc att ttc ggt gga ttc gtt ggg agt cgt gaa cat     1008
Ile Leu Asp Val Gly Ile Phe Gly Gly Phe Val Gly Ser Arg Glu His
                325                 330                 335 ttt ggt atg aat tac aat gca gat gtg cgc atg cct cat gat cga gca     1056
Phe Gly Met Asn Tyr Asn Ala Asp Val Arg Met Pro His Asp Arg Ala
            340                 345                 350 tgg gat ttt att tat aac aat ggt gta tca gtt gcc tat ctt agc ttt     1104
Trp Asp Phe Ile Tyr Asn Asn Gly Val Ser Val Ala Tyr Leu Ser Phe
        355                 360                 365 gct gag gtt gat caa tac ggc aat gtc aac gtg tct tac ttc aat gac     1152
Ala Glu Val Asp Gln Tyr Gly Asn Val Asn Val Ser Tyr Phe Asn Asp
    370                 375                 380 cga cta aat gga tgt ggt ggc ttt ata gac att acg caa tct gta aat     1200
Arg Leu Asn Gly Cys Gly Gly Phe Ile Asp Ile Thr Gln Ser Val Asn
385                 390                 395                 400 aaa att atc ttt tca ggt act ttt gta gct ggc agt cat gtc tca tgc     1248
Lys Ile Ile Phe Ser Gly Thr Phe Val Ala Gly Ser His Val Ser Cys
                405                 410                 415 cat aat caa cga tta aac att gaa act gaa gga caa aac cag aaa ttt     1296
His Asn Gln Arg Leu Asn Ile Glu Thr Glu Gly Gln Asn Gln Lys Phe
            420                 425                 430 gta tca gat gtg agc cat atc gac ttt aat gca caa tat tca caa tca     1344
Val Ser Asp Val Ser His Ile Asp Phe Asn Ala Gln Tyr Ser Gln Ser
        435                 440                 445 ctc gag caa gaa gtc tat ttt gtt act gag cgt gca gta ttc gaa ctc     1392
Leu Glu Gln Glu Val Tyr Phe Val Thr Glu Arg Ala Val Phe Glu Leu
    450                 455                 460 acc aat caa ggc ttg aaa cta att gaa att gca cca ggt ctt gat ttg     1440
Thr Asn Gln Gly Leu Lys Leu Ile Glu Ile Ala Pro Gly Leu Asp Leu
465                 470                 475                 480 cat aaa gat att ttg aat caa atg gct ttt aaa cca att att gct gat     1488
His Lys Asp Ile Leu Asn Gln Met Ala Phe Lys Pro Ile Ile Ala Asp
                485                 490                 495 cat tta aaa tta att gat acc agc att tac aaa gaa aaa tgg gga caa     1536
His Leu Lys Leu Ile Asp Thr Ser Ile Tyr Lys Glu Lys Trp Gly Gln
            500                 505                 510 ctt aaa caa tca att cat aaa gta tga                                 1563
Leu Lys Gln Ser Ile His Lys Val
        515                 520

<210> SEQ ID NO 4
<211> LENGTH: 520
<212> TYPE: PRT
<213> ORGANISM: Staphylococcus aureus
```

```
<400> SEQUENCE: 4

Leu Lys Gln Ile Thr Trp His Asp Leu Gln His Ile Ile Lys Asp Gly
  1               5                  10                  15

Asp Val Ile Gly Leu Pro Ala Leu Ala Val Ala Asn Leu Pro Ala Glu
             20                  25                  30

Val Leu Arg Ala Val Leu Ala Gln His Asp Thr Tyr His Thr Pro Lys
         35                  40                  45

Asp Leu Thr Phe Ile Leu Ala Asn Asp Ile His Ser Leu Gly Ala Ala
 50                  55                  60

Pro Asp Leu Asp Asp Phe Ile Glu Arg Arg Met Ile Lys Arg Val Ile
 65                  70                  75                  80

Met Ser Ile Leu Thr Ala Ser Ser Lys Thr Ala Gln Ala Met Lys Asn
                 85                  90                  95

Asn Asp Ile Glu Ala Tyr Phe Leu Pro Gln Gly Ile Ile Ala Thr His
            100                 105                 110

Tyr Arg Gln Ser Asn Gln Leu Leu Pro Gly Val Ile Thr Lys Ile Gly
        115                 120                 125

Leu Asn Thr Ala Val Asp Pro Arg Tyr Gly Gly Lys Val Asn Thr
130                 135                 140

Arg Thr Thr Asp Asp Leu Val Ser Leu Val Thr Ile Asn Asp Glu Thr
145                 150                 155                 160

Tyr Leu His Tyr Thr Phe Pro Ser Val Asp Val Ala Leu Leu Arg Gly
                165                 170                 175

Thr Tyr Ala Asp Gln Gln Gly Asn Ile Tyr Leu Thr Gln Glu Ala Tyr
            180                 185                 190

Leu Ser Glu Cys Tyr His Val Ala Leu Asn Ala Lys Ala Asn His Gly
        195                 200                 205

Lys Val Ile Val Gln Val Lys Ala Leu Val Asp Gly Tyr Gln Leu Lys
    210                 215                 220

Pro Asn Glu Val Val Ile Pro Gly Asn Leu Val Asp Tyr Val Tyr Val
225                 230                 235                 240

Thr Glu Asp Glu Lys Asn His Arg Gln Val Ile Gln Ser His Tyr Leu
                245                 250                 255

Pro Ala Leu Ser Gly Glu Glu Arg Ile Asp Gly Ile Pro Glu Pro Ala
            260                 265                 270

Leu Pro Phe Asn Ser Arg Lys Leu Ile Leu Arg Arg Ala Ala Gln Phe
        275                 280                 285

Leu Thr Tyr Gly Asp Thr Ile Ser Ile Gly Tyr Gly Ile Asn Asn Glu
    290                 295                 300

Leu Ser Asn Leu Leu His Glu Glu Cys Val Glu His Asp Val Gln Pro
305                 310                 315                 320

Ile Leu Asp Val Gly Ile Phe Gly Gly Phe Val Gly Ser Arg Glu His
                325                 330                 335

Phe Gly Met Asn Tyr Asn Ala Asp Val Arg Met Pro His Asp Arg Ala
            340                 345                 350

Trp Asp Phe Ile Tyr Asn Asn Gly Val Ser Val Ala Tyr Leu Ser Phe
        355                 360                 365

Ala Glu Val Asp Gln Tyr Gly Asn Val Asn Val Ser Tyr Phe Asn Asp
    370                 375                 380

Arg Leu Asn Gly Cys Gly Gly Phe Ile Asp Ile Thr Gln Ser Val Asn
385                 390                 395                 400

Lys Ile Ile Phe Ser Gly Thr Phe Val Ala Gly Ser His Val Ser Cys
                405                 410                 415
```

```
His Asn Gln Arg Leu Asn Ile Glu Thr Glu Gly Gln Asn Gln Lys Phe
            420                 425                 430

Val Ser Asp Val Ser His Ile Asp Phe Asn Ala Gln Tyr Ser Gln Ser
            435                 440                 445

Leu Glu Gln Glu Val Tyr Phe Val Thr Glu Arg Ala Val Phe Glu Leu
        450                 455                 460

Thr Asn Gln Gly Leu Lys Leu Ile Glu Ile Ala Pro Gly Leu Asp Leu
465                 470                 475                 480

His Lys Asp Ile Leu Asn Gln Met Ala Phe Lys Pro Ile Ile Ala Asp
                    485                 490                 495

His Leu Lys Leu Ile Asp Thr Ser Ile Tyr Lys Glu Lys Trp Gly Gln
            500                 505                 510

Leu Lys Gln Ser Ile His Lys Val
        515                 520

<210> SEQ ID NO 5
<211> LENGTH: 1134
<212> TYPE: DNA
<213> ORGANISM: Alcanivorax borkumensis SK2
<220> FEATURE:
<221> NAME/KEY: CDS
<222> LOCATION: (1)..(1134)

<400> SEQUENCE: 5
```

| | | | | | | | | | | | | | | | | |
|---|---|---|---|---|---|---|---|---|---|---|---|---|---|---|---|---|
| atg | tgg | atg | gct | aaa | tca | cga | tta | aaa | aaa | agt | ctg | cgt | gcc | gtt | ggc | 48 |
| Met | Trp | Met | Ala | Lys | Ser | Arg | Leu | Lys | Lys | Ser | Leu | Arg | Ala | Val | Gly | |
| 1 | | | | 5 | | | | | 10 | | | | | 15 | | |
| cac | att | gtt | gag | cgc | agg | cgc | cac | ccg | caa | cgc | ttt | atc | cac | gtg | gat | 96 |
| His | Ile | Val | Glu | Arg | Arg | Arg | His | Pro | Gln | Arg | Phe | Ile | His | Val | Asp | |
| | | | 20 | | | | | 25 | | | | | 30 | | | |
| aaa | tgc | ccg | tgg | gag | gaa | gtg | tat | cgt | gac | ggc | atc | atg | gcg | gta | cgc | 144 |
| Lys | Cys | Pro | Trp | Glu | Glu | Val | Tyr | Arg | Asp | Gly | Ile | Met | Ala | Val | Arg | |
| | | 35 | | | | | 40 | | | | | 45 | | | | |
| cat | tac | agc | cta | ccc | tct | acg | gct | acg | gct | aaa | atc | tcg | att | aac | gat | 192 |
| His | Tyr | Ser | Leu | Pro | Ser | Thr | Ala | Thr | Ala | Lys | Ile | Ser | Ile | Asn | Asp | |
| | 50 | | | | | 55 | | | | | 60 | | | | | |
| gat | ttc | ctg | cct | gtt | tcc | cct | gta | aaa | cac | cgc | atc | ccc | ctt | ttg | ttg | 240 |
| Asp | Phe | Leu | Pro | Val | Ser | Pro | Val | Lys | His | Arg | Ile | Pro | Leu | Leu | Leu | |
| 65 | | | | 70 | | | | | 75 | | | | | 80 | | |
| gtt | ccg | gcg | ctg | ggt | att | cat | tgc | tgg | acc | tac | gat | ttg | atg | cca | aac | 288 |
| Val | Pro | Ala | Leu | Gly | Ile | His | Cys | Trp | Thr | Tyr | Asp | Leu | Met | Pro | Asn | |
| | | | | 85 | | | | | 90 | | | | | 95 | | |
| cga | tcc | atg | gtc | cgt | tat | ctt | atg | gct | cat | ggt | tat | gag | gtc | tat | ctg | 336 |
| Arg | Ser | Met | Val | Arg | Tyr | Leu | Met | Ala | His | Gly | Tyr | Glu | Val | Tyr | Leu | |
| | | | 100 | | | | | 105 | | | | | 110 | | | |
| gtt | gac | tgg | gga | aag | cct | tca | gat | acc | gac | tgc | agc | cta | aat | ttg | gac | 384 |
| Val | Asp | Trp | Gly | Lys | Pro | Ser | Asp | Thr | Asp | Cys | Ser | Leu | Asn | Leu | Asp | |
| | | | 115 | | | | | 120 | | | | | 125 | | | |
| acc | tac | gtc | aat | cgc | tgg | ttg | ccc | tct | gca | gtt | gaa | aca | gtg | cga | aaa | 432 |
| Thr | Tyr | Val | Asn | Arg | Trp | Leu | Pro | Ser | Ala | Val | Glu | Thr | Val | Arg | Lys | |
| | | 130 | | | | | 135 | | | | | 140 | | | | |
| cat | gcg | cag | acc | gaa | acc | atc | aac | atg | atg | ggc | tac | tgc | atg | ggc | gga | 480 |
| His | Ala | Gln | Thr | Glu | Thr | Ile | Asn | Met | Met | Gly | Tyr | Cys | Met | Gly | Gly | |
| 145 | | | | 150 | | | | | 155 | | | | | 160 | | |
| ctg | ctg | tgc | cta | atg | tat | cta | ggc | ggc | cac | agt | gat | gcg | ccg | gtg | cgt | 528 |
| Leu | Leu | Cys | Leu | Met | Tyr | Leu | Gly | Gly | His | Ser | Asp | Ala | Pro | Val | Arg | |
| | | | | 165 | | | | | 170 | | | | | 175 | | |
| agc | ctg | att | acc | att | gcc | agc | ccc | gtg | aat | ttt | cac | aaa | agc | ggc | ctt | 576 |
| Ser | Leu | Ile | Thr | Ile | Ala | Ser | Pro | Val | Asn | Phe | His | Lys | Ser | Gly | Leu | |

```
                         180                 185                 190
ttc ggc aag gcc tta ggg ctg gcg gct atc cct gcc atg cag ctc cat        624
Phe Gly Lys Ala Leu Gly Leu Ala Ala Ile Pro Ala Met Gln Leu His
            195                 200                 205 gac cgg ttt aag att cgt ctt gaa ccg ctc agt gat aag cta ttc cat        672
Asp Arg Phe Lys Ile Arg Leu Glu Pro Leu Ser Asp Lys Leu Phe His
    210                 215                 220 atc cct gcc agc ctc ctg gca ctt gga ttc aag atg acc aac cct cca        720
Ile Pro Ala Ser Leu Leu Ala Leu Gly Phe Lys Met Thr Asn Pro Pro
225                 230                 235                 240 gga gtg gtg cag gcc tac atg gat ctg atc cgc aat atc ggt gac cga        768
Gly Val Val Gln Ala Tyr Met Asp Leu Ile Arg Asn Ile Gly Asp Arg
                245                 250                 255 gaa tac gtc acc gag tac atg acc atg ggg cag tgg ttt aac gac atg        816
Glu Tyr Val Thr Glu Tyr Met Thr Met Gly Gln Trp Phe Asn Asp Met
            260                 265                 270 gtc gat tat cct ggt gcg gtg gtg cgt gag gtt atc gag aaa atg ctt        864
Val Asp Tyr Pro Gly Ala Val Val Arg Glu Val Ile Glu Lys Met Leu
    275                 280                 285 ctt gcc aat agt ctg gcc aaa ggc aaa atc cac atc ggc ggc cgc agc        912
Leu Ala Asn Ser Leu Ala Lys Gly Lys Ile His Ile Gly Gly Arg Ser
290                 295                 300 gtg gat ttc tca tcc att cag cag gat ttg ctc gct ttt gca ggc att        960
Val Asp Phe Ser Ser Ile Gln Gln Asp Leu Leu Ala Phe Ala Gly Ile
305                 310                 315                 320 acc gac aac att gtc agt ctt cga gcc gca cgg gat atc atc caa ctt       1008
Thr Asp Asn Ile Val Ser Leu Arg Ala Ala Arg Asp Ile Ile Gln Leu
                325                 330                 335 gtc ggc agc aaa gaa aaa cgc ttc gag gaa gta cct ggc gga cac gca       1056
Val Gly Ser Lys Glu Lys Arg Phe Glu Glu Val Pro Gly Gly His Ala
            340                 345                 350 ggc gct ttt tgc ggt tcg aaa gca cct tcc aat gcc tgg cgc atc agc       1104
Gly Ala Phe Cys Gly Ser Lys Ala Pro Ser Asn Ala Trp Arg Ile Ser
    355                 360                 365 gct gac tgg ttg gcg gcg cgc tca gca tag                               1134
Ala Asp Trp Leu Ala Ala Arg Ser Ala
    370                 375

<210> SEQ ID NO 6
<211> LENGTH: 377
<212> TYPE: PRT
<213> ORGANISM: Alcanivorax borkumensis SK2

<400> SEQUENCE: 6

Met Trp Met Ala Lys Ser Arg Leu Lys Lys Ser Leu Arg Ala Val Gly
1               5                   10                  15

His Ile Val Glu Arg Arg His Pro Gln Arg Phe Ile His Val Asp
            20                  25                  30

Lys Cys Pro Trp Glu Glu Val Tyr Arg Asp Gly Ile Met Ala Val Arg
        35                  40                  45

His Tyr Ser Leu Pro Ser Thr Ala Thr Ala Lys Ile Ser Ile Asn Asp
    50                  55                  60

Asp Phe Leu Pro Val Ser Pro Val Lys His Arg Ile Pro Leu Leu Leu
65                  70                  75                  80

Val Pro Ala Leu Gly Ile His Cys Trp Thr Tyr Asp Leu Met Pro Asn
                85                  90                  95

Arg Ser Met Val Arg Tyr Leu Met Ala His Gly Tyr Glu Val Tyr Leu
            100                 105                 110
```

Val Asp Trp Gly Lys Pro Ser Asp Thr Asp Cys Ser Leu Asn Leu Asp
        115                 120                 125

Thr Tyr Val Asn Arg Trp Leu Pro Ser Ala Val Glu Thr Val Arg Lys
    130                 135                 140

His Ala Gln Thr Glu Thr Ile Asn Met Met Gly Tyr Cys Met Gly Gly
145                 150                 155                 160

Leu Leu Cys Leu Met Tyr Leu Gly Gly His Ser Asp Ala Pro Val Arg
                165                 170                 175

Ser Leu Ile Thr Ile Ala Ser Pro Val Asn Phe His Lys Ser Gly Leu
            180                 185                 190

Phe Gly Lys Ala Leu Gly Leu Ala Ala Ile Pro Ala Met Gln Leu His
        195                 200                 205

Asp Arg Phe Lys Ile Arg Leu Glu Pro Leu Ser Asp Lys Leu Phe His
    210                 215                 220

Ile Pro Ala Ser Leu Leu Ala Leu Gly Phe Lys Met Thr Asn Pro Pro
225                 230                 235                 240

Gly Val Val Gln Ala Tyr Met Asp Leu Ile Arg Asn Ile Gly Asp Arg
                245                 250                 255

Glu Tyr Val Thr Glu Tyr Met Thr Met Gly Gln Trp Phe Asn Asp Met
            260                 265                 270

Val Asp Tyr Pro Gly Ala Val Val Arg Glu Val Ile Glu Lys Met Leu
        275                 280                 285

Leu Ala Asn Ser Leu Ala Lys Gly Lys Ile His Ile Gly Gly Arg Ser
    290                 295                 300

Val Asp Phe Ser Ser Ile Gln Gln Asp Leu Leu Ala Phe Ala Gly Ile
305                 310                 315                 320

Thr Asp Asn Ile Val Ser Leu Arg Ala Ala Arg Asp Ile Ile Gln Leu
                325                 330                 335

Val Gly Ser Lys Glu Lys Arg Phe Glu Glu Val Pro Gly Gly His Ala
            340                 345                 350

Gly Ala Phe Cys Gly Ser Lys Ala Pro Ser Asn Ala Trp Arg Ile Ser
        355                 360                 365

Ala Asp Trp Leu Ala Ala Arg Ser Ala
    370                 375

<210> SEQ ID NO 7
<211> LENGTH: 1689
<212> TYPE: DNA
<213> ORGANISM: Hyphomonas neptunium
<220> FEATURE:
<221> NAME/KEY: CDS
<222> LOCATION: (1)..(1689)

<400> SEQUENCE: 7

```
atg acg tca ccg aaa gac gag att gcc cgc aat gcg gct gaa aac acc        48
Met Thr Ser Pro Lys Asp Glu Ile Ala Arg Asn Ala Ala Glu Asn Thr
1               5                   10                  15 gcc gcg ctg aac ccg ctg ctg ggc ggc ttc aac cgc cag gaa ctg ctc        96
Ala Ala Leu Asn Pro Leu Leu Gly Gly Phe Asn Arg Gln Glu Leu Leu
                20                  25                  30 ggc gcc gtg ggt ctg atg ctg cgc tcc acg atg acc aac ccg gtc acc       144
Gly Ala Val Gly Leu Met Leu Arg Ser Thr Met Thr Asn Pro Val Thr
            35                  40                  45 acc gcc agg acc gcc ggc aag atc acg gcc gaa aac acc cag atc ctg       192
Thr Ala Arg Thr Ala Gly Lys Ile Thr Ala Glu Asn Thr Gln Ile Leu
        50                  55                  60 ctg ggc aag tcc aag cgc gaa gcc gac aag aaa gac cgc cgc ttc aag       240
```

|  |  |  |  |  |  |  |  |  |  |  |  |  |  |  |  |
|---|---|---|---|---|---|---|---|---|---|---|---|---|---|---|---|
| Leu | Gly | Lys | Ser | Lys | Arg | Glu | Ala | Asp | Lys | Lys | Asp | Arg | Arg | Phe | Lys |
| 65 |  |  |  | 70 |  |  |  | 75 |  |  |  | 80 |  |  |  |

| gac | ccc | gcc | tgg | gag | cat | aat | ccc | ttc | tac | aag | cgc | ggc | atg | cag | acc | 288 |
|---|---|---|---|---|---|---|---|---|---|---|---|---|---|---|---|---|
| Asp | Pro | Ala | Trp | Glu | His | Asn | Pro | Phe | Tyr | Lys | Arg | Gly | Met | Gln | Thr |  |
|  |  |  |  | 85 |  |  |  |  | 90 |  |  |  |  | 95 |  |  |

| tat | ctg | gcc | acc | cag | gaa | cac | ctc | cac | gcc | tgg | gtc | aac | gag | atc | aag | 336 |
|---|---|---|---|---|---|---|---|---|---|---|---|---|---|---|---|---|
| Tyr | Leu | Ala | Thr | Gln | Glu | His | Leu | His | Ala | Trp | Val | Asn | Glu | Ile | Lys |  |
|  |  |  | 100 |  |  |  |  | 105 |  |  |  |  | 110 |  |  |  |

| atg | ggc | gag | ctg | gaa | cag | gcg | cgc | gcc | aaa | ttc | gtc | atg | ggc | atg | atc | 384 |
|---|---|---|---|---|---|---|---|---|---|---|---|---|---|---|---|---|
| Met | Gly | Glu | Leu | Glu | Gln | Ala | Arg | Ala | Lys | Phe | Val | Met | Gly | Met | Ile |  |
|  |  |  | 115 |  |  |  |  | 120 |  |  |  |  | 125 |  |  |  |

| acc | gat | gcc | ctc | gcg | ccc | aca | aac | tcc | ctc | gtg | ggc | aat | ccg | gcc | gcc | 432 |
|---|---|---|---|---|---|---|---|---|---|---|---|---|---|---|---|---|
| Thr | Asp | Ala | Leu | Ala | Pro | Thr | Asn | Ser | Leu | Val | Gly | Asn | Pro | Ala | Ala |  |
| 130 |  |  |  |  | 135 |  |  |  |  | 140 |  |  |  |  |  |  |

| acc | aag | cgc | gtc | gtg | gat | tcg | ggc | ggc | ctc | tcc | ctg | ctc | aag | ggc | atg | 480 |
|---|---|---|---|---|---|---|---|---|---|---|---|---|---|---|---|---|
| Thr | Lys | Arg | Val | Val | Asp | Ser | Gly | Gly | Leu | Ser | Leu | Leu | Lys | Gly | Met |  |
| 145 |  |  |  |  | 150 |  |  |  |  | 155 |  |  |  |  | 160 |  |

| aaa | aac | ctc | tac | gac | gac | ctc | acc | aag | aat | ggc | ggt | ctc | ccg | tcc | cag | 528 |
|---|---|---|---|---|---|---|---|---|---|---|---|---|---|---|---|---|
| Lys | Asn | Leu | Tyr | Asp | Asp | Leu | Thr | Lys | Asn | Gly | Gly | Leu | Pro | Ser | Gln |  |
|  |  |  |  | 165 |  |  |  |  | 170 |  |  |  |  | 175 |  |  |

| gtc | gat | aaa | cgt | ccc | ttc | aag | gtt | ggt | gaa | aat | ctc | gcc | gtt | tca | aaa | 576 |
|---|---|---|---|---|---|---|---|---|---|---|---|---|---|---|---|---|
| Val | Asp | Lys | Arg | Pro | Phe | Lys | Val | Gly | Glu | Asn | Leu | Ala | Val | Ser | Lys |  |
|  |  | 180 |  |  |  |  | 185 |  |  |  |  | 190 |  |  |  |  |

| ggg | cag | gtg | gtc | tgg | aaa | aac | gag | atg | ctg | gag | ctg | atc | cag | tat | gcc | 624 |
|---|---|---|---|---|---|---|---|---|---|---|---|---|---|---|---|---|
| Gly | Gln | Val | Val | Trp | Lys | Asn | Glu | Met | Leu | Glu | Leu | Ile | Gln | Tyr | Ala |  |
|  |  | 195 |  |  |  |  | 200 |  |  |  |  | 205 |  |  |  |  |

| ccg | ctc | acc | gag | aag | gtc | cac | aag | acc | ccg | atc | ctg | ata | att | ccc | cca | 672 |
|---|---|---|---|---|---|---|---|---|---|---|---|---|---|---|---|---|
| Pro | Leu | Thr | Glu | Lys | Val | His | Lys | Thr | Pro | Ile | Leu | Ile | Ile | Pro | Pro |  |
| 210 |  |  |  |  | 215 |  |  |  |  | 220 |  |  |  |  |  |  |

| cag | atc | aac | aaa | ttc | tac | gcc | atg | gac | ctc | acg | ccg | atg | acg | tcg | atg | 720 |
|---|---|---|---|---|---|---|---|---|---|---|---|---|---|---|---|---|
| Gln | Ile | Asn | Lys | Phe | Tyr | Ala | Met | Asp | Leu | Thr | Pro | Met | Thr | Ser | Met |  |
| 225 |  |  |  |  | 230 |  |  |  |  | 235 |  |  |  |  | 240 |  |

| gtc | cag | ttc | ctc | ctc | gcg | atg | gaa | cag | cag | acc | ttt | gtg | att | tcg | tgg | 768 |
|---|---|---|---|---|---|---|---|---|---|---|---|---|---|---|---|---|
| Val | Gln | Phe | Leu | Leu | Ala | Met | Glu | Gln | Gln | Thr | Phe | Val | Ile | Ser | Trp |  |
|  |  |  |  | 245 |  |  |  |  | 250 |  |  |  |  | 255 |  |  |

| cgc | aac | ccc | acc | aag | aag | cac | aaa | gac | tgg | ggg | atg | aac | gac | tat | atc | 816 |
|---|---|---|---|---|---|---|---|---|---|---|---|---|---|---|---|---|
| Arg | Asn | Pro | Thr | Lys | Lys | His | Lys | Asp | Trp | Gly | Met | Asn | Asp | Tyr | Ile |  |
|  |  |  | 260 |  |  |  |  | 265 |  |  |  |  | 270 |  |  |  |

| gac | agc | ctc | gtc | cag | gcc | agc | gaa | gtc | atc | cgc | aag | atc | acg | aag | tcg | 864 |
|---|---|---|---|---|---|---|---|---|---|---|---|---|---|---|---|---|
| Asp | Ser | Leu | Val | Gln | Ala | Ser | Glu | Val | Ile | Arg | Lys | Ile | Thr | Lys | Ser |  |
|  |  | 275 |  |  |  |  | 280 |  |  |  |  | 285 |  |  |  |  |

| cct | aag | atc | aac | gtc | tcc | ggc | gcc | tgc | tcg | ggc | ggc | atc | acc | acg | gcc | 912 |
|---|---|---|---|---|---|---|---|---|---|---|---|---|---|---|---|---|
| Pro | Lys | Ile | Asn | Val | Ser | Gly | Ala | Cys | Ser | Gly | Gly | Ile | Thr | Thr | Ala |  |
| 290 |  |  |  |  | 295 |  |  |  |  | 300 |  |  |  |  |  |  |

| acc | ttc | gcg | agc | ctt | ctt | gcc | gcc | gcc | gat | gac | aaa | cgc | atc | aac | tcg | 960 |
|---|---|---|---|---|---|---|---|---|---|---|---|---|---|---|---|---|
| Thr | Phe | Ala | Ser | Leu | Leu | Ala | Ala | Ala | Asp | Asp | Lys | Arg | Ile | Asn | Ser |  |
| 305 |  |  |  |  | 310 |  |  |  |  | 315 |  |  |  |  | 320 |  |

| ctc | acc | ttc | atg | gtc | tgc | gtg | ctc | aac | ccc | cag | cgc | gac | gac | agc | gac | 1008 |
|---|---|---|---|---|---|---|---|---|---|---|---|---|---|---|---|---|
| Leu | Thr | Phe | Met | Val | Cys | Val | Leu | Asn | Pro | Gln | Arg | Asp | Asp | Ser | Asp |  |
|  |  |  |  | 325 |  |  |  |  | 330 |  |  |  |  | 335 |  |  |

| att | ggc | cag | atc | gtg | tcg | gat | ggc | agc | ctc | gaa | atc | gcg | cgc | aag | tat | 1056 |
|---|---|---|---|---|---|---|---|---|---|---|---|---|---|---|---|---|
| Ile | Gly | Gln | Ile | Val | Ser | Asp | Gly | Ser | Leu | Glu | Ile | Ala | Arg | Lys | Tyr |  |
|  |  |  | 340 |  |  |  |  | 345 |  |  |  |  | 350 |  |  |  |

| tcc | aaa | tcc | cgc | ggc | atc | ctg | aag | ggc | gat | gac | ctt | gcc | cgc | atg | ttt | 1104 |
|---|---|---|---|---|---|---|---|---|---|---|---|---|---|---|---|---|
| Ser | Lys | Ser | Arg | Gly | Ile | Leu | Lys | Gly | Asp | Asp | Leu | Ala | Arg | Met | Phe |  |
|  |  | 355 |  |  |  |  | 360 |  |  |  |  | 365 |  |  |  |  |

| gcc | tgg | atg | cgc | ccg | aac | gac | ctc | att | tgg | aac | tat | gtc | gtc | aac | aac | 1152 |
|---|---|---|---|---|---|---|---|---|---|---|---|---|---|---|---|---|
| Ala | Trp | Met | Arg | Pro | Asn | Asp | Leu | Ile | Trp | Asn | Tyr | Val | Val | Asn | Asn |  |
| 370 |  |  |  |  | 375 |  |  |  |  | 380 |  |  |  |  |  |  |

```
tat ctc atg ggc gaa gat cct ccg ccc tat gac gtt ctg ttc tgg aac    1200
Tyr Leu Met Gly Glu Asp Pro Pro Pro Tyr Asp Val Leu Phe Trp Asn
385                 390                 395                 400 aac gac aca acc aac ctc ccg gcc cag ctg cat tca gat tat ctg gat    1248
Asn Asp Thr Thr Asn Leu Pro Ala Gln Leu His Ser Asp Tyr Leu Asp
            405                 410                 415 att gcc ctc agc caa cct ttc gat aat ccg ggt acg gtt gaa gtc tcc    1296
Ile Ala Leu Ser Gln Pro Phe Asp Asn Pro Gly Thr Val Glu Val Ser
        420                 425                 430 ggc cat atg gca gac ctc agc aag gtc acc gca gat gcc ttc gtc gtt    1344
Gly His Met Ala Asp Leu Ser Lys Val Thr Ala Asp Ala Phe Val Val
    435                 440                 445 gct ggc gtc aca gat cac atc acc ccc tgg aaa gcc tgc tac cgc aca    1392
Ala Gly Val Thr Asp His Ile Thr Pro Trp Lys Ala Cys Tyr Arg Thr
450                 455                 460 ccg tct ctg ctc ggc tcg aag aat gtc gaa ttc atc ctc tct tcc agc    1440
Pro Ser Leu Leu Gly Ser Lys Asn Val Glu Phe Ile Leu Ser Ser Ser
465                 470                 475                 480 ggt cac ctc caa tcc ctg atc aac ccg ccc ggt aat ccg aag gcg aag    1488
Gly His Leu Gln Ser Leu Ile Asn Pro Pro Gly Asn Pro Lys Ala Lys
            485                 490                 495 tat ttc cgg ggc aag gag atc aaa ccg acg gcg gat gaa tgg gcg ctg    1536
Tyr Phe Arg Gly Lys Glu Ile Lys Pro Thr Ala Asp Glu Trp Ala Leu
        500                 505                 510 gcc gct gaa gaa cag gcc ggc tcc tgg tgg ccg ctc tgg ggc caa tgg    1584
Ala Ala Glu Glu Gln Ala Gly Ser Trp Trp Pro Leu Trp Gly Gln Trp
    515                 520                 525 ctc aaa gaa cgc tcc ggc gcc ctg aaa gct gca cct aaa gtg ctt ggc    1632
Leu Lys Glu Arg Ser Gly Ala Leu Lys Ala Ala Pro Lys Val Leu Gly
530                 535                 540 aac gaa gcc ttc ccc ccc atc tat gca gcg cca ggc cgc tac gtc ttc    1680
Asn Glu Ala Phe Pro Pro Ile Tyr Ala Ala Pro Gly Arg Tyr Val Phe
545                 550                 555                 560 aac gac tag                                                        1689
Asn Asp

<210> SEQ ID NO 8
<211> LENGTH: 562
<212> TYPE: PRT
<213> ORGANISM: Hyphomonas neptunium

<400> SEQUENCE: 8

Met Thr Ser Pro Lys Asp Glu Ile Ala Arg Asn Ala Ala Glu Asn Thr
1               5                   10                  15

Ala Ala Leu Asn Pro Leu Leu Gly Gly Phe Asn Arg Gln Glu Leu Leu
            20                  25                  30

Gly Ala Val Gly Leu Met Leu Arg Ser Thr Met Thr Asn Pro Val Thr
        35                  40                  45

Thr Ala Arg Thr Ala Gly Lys Ile Thr Ala Glu Asn Thr Gln Ile Leu
    50                  55                  60

Leu Gly Lys Ser Lys Arg Glu Ala Asp Lys Asp Arg Arg Phe Lys
65                  70                  75                  80

Asp Pro Ala Trp Glu His Asn Pro Phe Tyr Lys Arg Gly Met Gln Thr
                85                  90                  95

Tyr Leu Ala Thr Gln Glu His Leu His Ala Trp Val Asn Glu Ile Lys
            100                 105                 110

Met Gly Glu Leu Glu Gln Ala Arg Ala Lys Phe Val Met Gly Met Ile
        115                 120                 125
```

```
Thr Asp Ala Leu Ala Pro Thr Asn Ser Leu Val Gly Asn Pro Ala Ala
130                 135                 140

Thr Lys Arg Val Val Asp Ser Gly Gly Leu Ser Leu Leu Lys Gly Met
145                 150                 155                 160

Lys Asn Leu Tyr Asp Asp Leu Thr Lys Asn Gly Gly Leu Pro Ser Gln
                165                 170                 175

Val Asp Lys Arg Pro Phe Lys Val Gly Glu Asn Leu Ala Val Ser Lys
                180                 185                 190

Gly Gln Val Val Trp Lys Asn Glu Met Leu Glu Leu Ile Gln Tyr Ala
                195                 200                 205

Pro Leu Thr Glu Lys Val His Lys Thr Pro Ile Leu Ile Ile Pro Pro
210                 215                 220

Gln Ile Asn Lys Phe Tyr Ala Met Asp Leu Thr Pro Met Thr Ser Met
225                 230                 235                 240

Val Gln Phe Leu Leu Ala Met Glu Gln Gln Thr Phe Val Ile Ser Trp
                245                 250                 255

Arg Asn Pro Thr Lys Lys His Lys Asp Trp Gly Met Asn Asp Tyr Ile
                260                 265                 270

Asp Ser Leu Val Gln Ala Ser Glu Val Ile Arg Lys Ile Thr Lys Ser
                275                 280                 285

Pro Lys Ile Asn Val Ser Gly Ala Cys Ser Gly Gly Ile Thr Thr Ala
                290                 295                 300

Thr Phe Ala Ser Leu Leu Ala Ala Asp Asp Lys Arg Ile Asn Ser
305                 310                 315                 320

Leu Thr Phe Met Val Cys Val Leu Asn Pro Gln Arg Asp Asp Ser Asp
                325                 330                 335

Ile Gly Gln Ile Val Ser Asp Gly Ser Leu Glu Ile Ala Arg Lys Tyr
                340                 345                 350

Ser Lys Ser Arg Gly Ile Leu Lys Gly Asp Asp Leu Ala Arg Met Phe
                355                 360                 365

Ala Trp Met Arg Pro Asn Asp Leu Ile Trp Asn Tyr Val Val Asn Asn
370                 375                 380

Tyr Leu Met Gly Glu Asp Pro Pro Tyr Asp Val Leu Phe Trp Asn
385                 390                 395                 400

Asn Asp Thr Thr Asn Leu Pro Ala Gln Leu His Ser Asp Tyr Leu Asp
                405                 410                 415

Ile Ala Leu Ser Gln Pro Phe Asp Asn Pro Gly Thr Val Glu Val Ser
                420                 425                 430

Gly His Met Ala Asp Leu Ser Lys Val Thr Ala Asp Ala Phe Val Val
                435                 440                 445

Ala Gly Val Thr Asp His Ile Thr Pro Trp Lys Ala Cys Tyr Arg Thr
450                 455                 460

Pro Ser Leu Leu Gly Ser Lys Asn Val Glu Phe Ile Leu Ser Ser Ser
465                 470                 475                 480

Gly His Leu Gln Ser Leu Ile Asn Pro Gly Asn Pro Lys Ala Lys
                485                 490                 495

Tyr Phe Arg Gly Lys Glu Ile Lys Pro Thr Ala Asp Glu Trp Ala Leu
                500                 505                 510

Ala Ala Glu Glu Gln Ala Gly Ser Trp Trp Pro Leu Trp Gly Gln Trp
                515                 520                 525

Leu Lys Glu Arg Ser Gly Ala Leu Lys Ala Ala Pro Lys Val Leu Gly
530                 535                 540

Asn Glu Ala Phe Pro Pro Ile Tyr Ala Ala Pro Gly Arg Tyr Val Phe
```

<210> SEQ ID NO 9
<211> LENGTH: 1722
<212> TYPE: DNA
<213> ORGANISM: Rhodobacter sphaeroides
<220> FEATURE:
<221> NAME/KEY: CDS
<222> LOCATION: (1)..(1722)

<400> SEQUENCE: 9

| | | | | | | | | | | | | | | | | |
|---|---|---|---|---|---|---|---|---|---|---|---|---|---|---|---|---|
| atg | tct | gac | atg | aag | tgg | aat | gcg | gaa | ggt | gcg | ccg | gcc | tat | ggg | caa | 48 |
| Met | Ser | Asp | Met | Lys | Trp | Asn | Ala | Glu | Gly | Ala | Pro | Ala | Tyr | Gly | Gln | |
| 1 | | | | 5 | | | | | 10 | | | | | 15 | | |
| gcg | ctg | gac | cgg | gcg | gca | cgc | gcc | gcc | atc | gca | ggc | atg | acg | cgg | ggt | 96 |
| Ala | Leu | Asp | Arg | Ala | Ala | Arg | Ala | Ala | Ile | Ala | Gly | Met | Thr | Arg | Gly | |
| | | | 20 | | | | | 25 | | | | | 30 | | | |
| ctg | gcg | ccc | tcg | gtg | ctg | gcg | acg | gct | gcg | ctc | gac | tgg | atg | atg | cat | 144 |
| Leu | Ala | Pro | Ser | Val | Leu | Ala | Thr | Ala | Ala | Leu | Asp | Trp | Met | Met | His | |
| | | 35 | | | | | 40 | | | | | 45 | | | | |
| ctg | gcc | gcg | gcc | ccc | gga | aaa | cag | gcg | gag | ctg | tgg | gag | aag | gcg | gca | 192 |
| Leu | Ala | Ala | Ala | Pro | Gly | Lys | Gln | Ala | Glu | Leu | Trp | Glu | Lys | Ala | Ala | |
| | 50 | | | | | 55 | | | | | 60 | | | | | |
| act | gcg | tcc | gcc | gcc | ttg | atg | caa | gcg | ggg | ctg | cag | ccg | cac | gag | gct | 240 |
| Thr | Ala | Ser | Ala | Ala | Leu | Met | Gln | Ala | Gly | Leu | Gln | Pro | His | Glu | Ala | |
| 65 | | | | | 70 | | | | | 75 | | | | | 80 | |
| ccg | gtc | agg | gac | cgc | cgc | tac | gct | tcg | gag | gcg | tgg | agc | cgc | cag | ccc | 288 |
| Pro | Val | Arg | Asp | Arg | Arg | Tyr | Ala | Ser | Glu | Ala | Trp | Ser | Arg | Gln | Pro | |
| | | | | 85 | | | | | 90 | | | | | 95 | | |
| ttc | gcc | gcg | ctg | cgc | gac | agc | ttc | ctt | ctg | acc | gag | gac | tgg | tgg | cag | 336 |
| Phe | Ala | Ala | Leu | Arg | Asp | Ser | Phe | Leu | Leu | Thr | Glu | Asp | Trp | Trp | Gln | |
| | | | 100 | | | | | 105 | | | | | 110 | | | |
| acg | gcc | acc | acc | ggc | ctg | cgc | ggg | atg | gac | cgg | gcg | cat | gag | gcg | gcg | 384 |
| Thr | Ala | Thr | Thr | Gly | Leu | Arg | Gly | Met | Asp | Arg | Ala | His | Glu | Ala | Ala | |
| | | 115 | | | | | 120 | | | | | 125 | | | | |
| ctg | agc | ttt | tcg | gtg | cgc | cag | atg | ctc | gac | gtc | tgg | tcg | ccc | tcg | aac | 432 |
| Leu | Ser | Phe | Ser | Val | Arg | Gln | Met | Leu | Asp | Val | Trp | Ser | Pro | Ser | Asn | |
| | 130 | | | | | 135 | | | | | 140 | | | | | |
| aac | ccg | ttc | ctc | aac | ccc | gag | gtg | ctg | gcc | cgc | acg | aca | gag | acg | cgg | 480 |
| Asn | Pro | Phe | Leu | Asn | Pro | Glu | Val | Leu | Ala | Arg | Thr | Thr | Glu | Thr | Arg | |
| 145 | | | | | 150 | | | | | 155 | | | | | 160 | |
| ggc | gcc | aac | ctc | atg | cag | ggc | gcg | atg | aat | ttc | gcg | ggc | gac | atg | gcc | 528 |
| Gly | Ala | Asn | Leu | Met | Gln | Gly | Ala | Met | Asn | Phe | Ala | Gly | Asp | Met | Ala | |
| | | | | 165 | | | | | 170 | | | | | 175 | | |
| cgc | ctc | gcg | acc | ggc | gtg | ccg | atg | gac | gaa | ggc | ggg | ttc | cgc | atc | ggc | 576 |
| Arg | Leu | Ala | Thr | Gly | Val | Pro | Met | Asp | Glu | Gly | Gly | Phe | Arg | Ile | Gly | |
| | | | 180 | | | | | 185 | | | | | 190 | | | |
| gag | acg | ctg | gcc | gcg | aca | ccg | ggc | aag | gtc | gtc | ctg | cgc | acg | cat | ctg | 624 |
| Glu | Thr | Leu | Ala | Ala | Thr | Pro | Gly | Lys | Val | Val | Leu | Arg | Thr | His | Leu | |
| | | 195 | | | | | 200 | | | | | 205 | | | | |
| atg | gag | ctg | atc | cag | tac | agc | ccc | acc | acc | agg | gag | gtg | cat | ccc | gag | 672 |
| Met | Glu | Leu | Ile | Gln | Tyr | Ser | Pro | Thr | Thr | Arg | Glu | Val | His | Pro | Glu | |
| | 210 | | | | | 215 | | | | | 220 | | | | | |
| ccg | gtg | cta | atc | gtg | ccg | gcc | tgg | atc | atg | aaa | tat | tac | atc | ctc | gac | 720 |
| Pro | Val | Leu | Ile | Val | Pro | Ala | Trp | Ile | Met | Lys | Tyr | Tyr | Ile | Leu | Asp | |
| 225 | | | | | 230 | | | | | 235 | | | | | 240 | |
| ctg | agc | gag | cag | aat | tcg | ctg | gtc | cgc | tgg | ctg | gtg | gcg | cag | ggc | ttc | 768 |
| Leu | Ser | Glu | Gln | Asn | Ser | Leu | Val | Arg | Trp | Leu | Val | Ala | Gln | Gly | Phe | |
| | | | | 245 | | | | | 250 | | | | | 255 | | |

|     |     |
| --- | --- |
| acc gtc ttc atg atc tcc tgg cgc aac ccc gag tcc gag gac cgc gat<br>Thr Val Phe Met Ile Ser Trp Arg Asn Pro Glu Ser Glu Asp Arg Asp<br>260                        265                        270 | 816 |
| ctg ggt ctg atc gac tat ctc gat cag ggg ccg cgc gcc gcg ctg aag<br>Leu Gly Leu Ile Asp Tyr Leu Asp Gln Gly Pro Arg Ala Ala Leu Lys<br>275                        280                        285 | 864 |
| gcg atc cag acg atc acc ggc gcg ccg aag gtc cat gcg gcg ggc tac<br>Ala Ile Gln Thr Ile Thr Gly Ala Pro Lys Val His Ala Ala Gly Tyr<br>290                        295                        300 | 912 |
| tgc ctc ggc ggc acg ctt ctg tcg atc atg gcc gcg cgc atg gcc cac<br>Cys Leu Gly Gly Thr Leu Leu Ser Ile Met Ala Ala Arg Met Ala His<br>305                        310                        315                        320 | 960 |
| gat cac gac gag cgg ctg gcc tcg atg acg ctg ttc gcg gcg cag gtc<br>Asp His Asp Glu Arg Leu Ala Ser Met Thr Leu Phe Ala Ala Gln Val<br>                    325                        330                        335 | 1008 |
| gat ttc tcg gaa gcg ggc gag ctc gcg ctc ttc atc tcg gag gcg cag<br>Asp Phe Ser Glu Ala Gly Glu Leu Ala Leu Phe Ile Ser Glu Ala Gln<br>340                        345                        350 | 1056 |
| gtg gcg ctg ctc gag gac atg atg tgg cat cag ggc tat ctc gac agc<br>Val Ala Leu Leu Glu Asp Met Met Trp His Gln Gly Tyr Leu Asp Ser<br>355                        360                        365 | 1104 |
| gat cag atg agc ggg gcc ttc acg ctt ctg cgg tcg aac gat ctg atc<br>Asp Gln Met Ser Gly Ala Phe Thr Leu Leu Arg Ser Asn Asp Leu Ile<br>370                        375                        380 | 1152 |
| tgg tcg cgg atg atc cat gaa tac atg atg ggc gag cgg ccg cat ccg<br>Trp Ser Arg Met Ile His Glu Tyr Met Met Gly Glu Arg Pro His Pro<br>385                        390                        395                        400 | 1200 |
| aac gac ctg atg acc tgg aac gcg gat tcg acc cgg atg ccc tac cgg<br>Asn Asp Leu Met Thr Trp Asn Ala Asp Ser Thr Arg Met Pro Tyr Arg<br>                    405                        410                        415 | 1248 |
| atg cat tcg gaa tat ctg cgc cat ctg ttc ctc gag aac cgc ttc gcc<br>Met His Ser Glu Tyr Leu Arg His Leu Phe Leu Glu Asn Arg Phe Ala<br>420                        425                        430 | 1296 |
| gag ggc aag ttc gag ctc gag ggc cat gcg ctg tcg ctg acc gag ctg<br>Glu Gly Lys Phe Glu Leu Glu Gly His Ala Leu Ser Leu Thr Glu Leu<br>                    435                        440                        445 | 1344 |
| cgg ctg ccg atc ctc gcg gtg ggc acc gag acg gac cat gtc gcg ccc<br>Arg Leu Pro Ile Leu Ala Val Gly Thr Glu Thr Asp His Val Ala Pro<br>450                        455                        460 | 1392 |
| tgg cgg tcg gtg ttc aag atc cag cgg ctg acc gag acc gag acg acc<br>Trp Arg Ser Val Phe Lys Ile Gln Arg Leu Thr Glu Thr Glu Thr Thr<br>465                        470                        475                        480 | 1440 |
| ttc gtg ctc acc tcg ggc ggg cac aat gcc ggc atc gtg tcc gag ccg<br>Phe Val Leu Thr Ser Gly Gly His Asn Ala Gly Ile Val Ser Glu Pro<br>                    485                        490                        495 | 1488 |
| ggg cat ccg cgg cgg cat ttc cgc atc gcc acc acc ggg cgc gac gat<br>Gly His Pro Arg Arg His Phe Arg Ile Ala Thr Thr Gly Arg Asp Asp<br>                    500                        505                        510 | 1536 |
| ccc tac cgc gac gcc gac gaa tgg ttc gcc gaa acg gcg ccg gtc gag<br>Pro Tyr Arg Asp Ala Asp Glu Trp Phe Ala Glu Thr Ala Pro Val Glu<br>                    515                        520                        525 | 1584 |
| ggg tcg tgg tgg ccc gcc tgg ggc gcc tgg ctc gcc gaa cgc tcc acg<br>Gly Ser Trp Trp Pro Ala Trp Gly Ala Trp Leu Ala Glu Arg Ser Thr<br>530                        535                        540 | 1632 |
| ccc aag ggc aag ctg ccc ccg atg ggc aac gcc cgg agc ggc tac cct<br>Pro Lys Gly Lys Leu Pro Pro Met Gly Asn Ala Arg Ser Gly Tyr Pro<br>545                        550                        555                        560 | 1680 |
| gcg ctc tgc gag gcg ccg ggc acc tac atc ctg caa cgc tga<br>Ala Leu Cys Glu Ala Pro Gly Thr Tyr Ile Leu Gln Arg<br>                    565                        570 | 1722 |

<210> SEQ ID NO 10
<211> LENGTH: 573
<212> TYPE: PRT
<213> ORGANISM: Rhodobacter sphaeroides

<400> SEQUENCE: 10

```
Met Ser Asp Met Lys Trp Asn Ala Glu Gly Ala Pro Ala Tyr Gly Gln
1               5                   10                  15

Ala Leu Asp Arg Ala Ala Arg Ala Ile Ala Gly Met Thr Arg Gly
                20                  25                  30

Leu Ala Pro Ser Val Leu Ala Thr Ala Ala Leu Asp Trp Met Met His
                35                  40                  45

Leu Ala Ala Ala Pro Gly Lys Gln Ala Glu Leu Trp Glu Lys Ala Ala
        50                  55                  60

Thr Ala Ser Ala Ala Leu Met Gln Ala Gly Leu Gln Pro His Glu Ala
65                  70                  75                  80

Pro Val Arg Asp Arg Arg Tyr Ala Ser Glu Ala Trp Ser Arg Gln Pro
                85                  90                  95

Phe Ala Ala Leu Arg Asp Ser Phe Leu Leu Thr Glu Asp Trp Trp Gln
            100                 105                 110

Thr Ala Thr Thr Gly Leu Arg Gly Met Asp Arg Ala His Glu Ala Ala
            115                 120                 125

Leu Ser Phe Ser Val Arg Gln Met Leu Asp Val Trp Ser Pro Ser Asn
        130                 135                 140

Asn Pro Phe Leu Asn Pro Glu Val Leu Ala Arg Thr Thr Glu Thr Arg
145                 150                 155                 160

Gly Ala Asn Leu Met Gln Gly Ala Met Asn Phe Ala Gly Asp Met Ala
                165                 170                 175

Arg Leu Ala Thr Gly Val Pro Met Asp Glu Gly Gly Phe Arg Ile Gly
            180                 185                 190

Glu Thr Leu Ala Ala Thr Pro Gly Lys Val Val Leu Arg Thr His Leu
            195                 200                 205

Met Glu Leu Ile Gln Tyr Ser Pro Thr Thr Arg Glu Val His Pro Glu
    210                 215                 220

Pro Val Leu Ile Val Pro Ala Trp Ile Met Lys Tyr Tyr Ile Leu Asp
225                 230                 235                 240

Leu Ser Glu Gln Asn Ser Leu Val Arg Trp Leu Val Ala Gln Gly Phe
                245                 250                 255

Thr Val Phe Met Ile Ser Trp Arg Asn Pro Glu Ser Glu Asp Arg Asp
            260                 265                 270

Leu Gly Leu Ile Asp Tyr Leu Asp Gln Gly Pro Arg Ala Ala Leu Lys
            275                 280                 285

Ala Ile Gln Thr Ile Thr Gly Ala Pro Lys Val His Ala Ala Gly Tyr
        290                 295                 300

Cys Leu Gly Gly Thr Leu Leu Ser Ile Met Ala Ala Arg Met Ala His
305                 310                 315                 320

Asp His Asp Glu Arg Leu Ala Ser Met Thr Leu Phe Ala Ala Gln Val
                325                 330                 335

Asp Phe Ser Glu Ala Gly Glu Leu Ala Leu Phe Ile Ser Glu Ala Gln
            340                 345                 350

Val Ala Leu Leu Glu Asp Met Met Trp His Gln Gly Tyr Leu Asp Ser
        355                 360                 365

Asp Gln Met Ser Gly Ala Phe Thr Leu Leu Arg Ser Asn Asp Leu Ile
```

```
                      370                 375                 380
Trp Ser Arg Met Ile His Glu Tyr Met Met Gly Glu Arg Pro His Pro
385                 390                 395                 400

Asn Asp Leu Met Thr Trp Asn Ala Asp Ser Thr Arg Met Pro Tyr Arg
                405                 410                 415

Met His Ser Glu Tyr Leu Arg His Leu Phe Leu Glu Asn Arg Phe Ala
            420                 425                 430

Glu Gly Lys Phe Glu Leu Glu Gly His Ala Leu Ser Leu Thr Glu Leu
        435                 440                 445

Arg Leu Pro Ile Leu Ala Val Gly Thr Glu Thr Asp His Val Ala Pro
    450                 455                 460

Trp Arg Ser Val Phe Lys Ile Gln Arg Leu Thr Glu Thr Glu Thr Thr
465                 470                 475                 480

Phe Val Leu Thr Ser Gly Gly His Asn Ala Gly Ile Val Ser Glu Pro
                485                 490                 495

Gly His Pro Arg Arg His Phe Arg Ile Ala Thr Thr Gly Arg Asp Asp
            500                 505                 510

Pro Tyr Arg Asp Ala Asp Glu Trp Phe Ala Glu Thr Ala Pro Val Glu
        515                 520                 525

Gly Ser Trp Trp Pro Ala Trp Gly Ala Trp Leu Ala Glu Arg Ser Thr
    530                 535                 540

Pro Lys Gly Lys Leu Pro Pro Met Gly Asn Ala Arg Ser Gly Tyr Pro
545                 550                 555                 560

Ala Leu Cys Glu Ala Pro Gly Thr Tyr Ile Leu Gln Arg
                565                 570

<210> SEQ ID NO 11
<211> LENGTH: 1806
<212> TYPE: DNA
<213> ORGANISM: Rhodobacter sphaeroides
<220> FEATURE:
<221> NAME/KEY: CDS
<222> LOCATION: (1)..(1806)

<400> SEQUENCE: 11 atg gca acc gaa gag cag tct ccg ggt tcc ggc cgt gac gct cag ttc        48
Met Ala Thr Glu Glu Gln Ser Pro Gly Ser Gly Arg Asp Ala Gln Phe
1               5                   10                  15 gag cgt ctg aac gcg aat ctc acc cgc atc gac gag ctg tcg aaa cgg        96
Glu Arg Leu Asn Ala Asn Leu Thr Arg Ile Asp Glu Leu Ser Lys Arg
                20                  25                  30 ctg acg gcc gct ctc acg aag cgc aaa ctg tcg gac ccc gcg ctg cac       144
Leu Thr Ala Ala Leu Thr Lys Arg Lys Leu Ser Asp Pro Ala Leu His
            35                  40                  45 ggg ccc tcg ggc gac gtc ttc ctg aag gcg atg acg gcc tac atg gcc       192
Gly Pro Ser Gly Asp Val Phe Leu Lys Ala Met Thr Ala Tyr Met Ala
        50                  55                  60 gag atg atg cag aac ccg gcc aag atc ctc gag cat cag atc agt ttc       240
Glu Met Met Gln Asn Pro Ala Lys Ile Leu Glu His Gln Ile Ser Phe
65                  70                  75                  80 tgg ggc aag agc ctg aaa cat tac gtc gag gct cag cac cag ctg gtg       288
Trp Gly Lys Ser Leu Lys His Tyr Val Glu Ala Gln His Gln Leu Val
                85                  90                  95 aag ggc gag ctg aag ccg ccg ccg gac gtg acg ccg aag gac cgc cgc       336
Lys Gly Glu Leu Lys Pro Pro Pro Asp Val Thr Pro Lys Asp Arg Arg
                100                 105                 110 ttc tcg aac ccg ctc tgg cag acg cat ccc ttc ttc aac tat ctc aag       384
Phe Ser Asn Pro Leu Trp Gln Thr His Pro Phe Phe Asn Tyr Leu Lys
```

-continued

|     |     |     | 115 |     |     |     |     | 120 |     |     |     |     | 125 |     |     |      |
|-----|-----|-----|-----|-----|-----|-----|-----|-----|-----|-----|-----|-----|-----|-----|-----|------|
| cag | cag | tat | ctg | atg | aac | gcc | gag | gcg | gtg | aat | cag | gcc | gtc | gag | gcg | 432  |
| Gln | Gln | Tyr | Leu | Met | Asn | Ala | Glu | Ala | Val | Asn | Gln | Ala | Val | Glu | Ala |      |
|     | 130 |     |     |     |     | 135 |     |     |     |     | 140 |     |     |     |     |      |

| ctg | gag | cat | atc | gag | ccg | tcc | gac | aag | aag | cgg | gtc | gaa | tat | ttc | tcg | 480 |
|-----|-----|-----|-----|-----|-----|-----|-----|-----|-----|-----|-----|-----|-----|-----|-----|-----|
| Leu | Glu | His | Ile | Glu | Pro | Ser | Asp | Lys | Lys | Arg | Val | Glu | Tyr | Phe | Ser |     |
| 145 |     |     |     |     | 150 |     |     |     |     | 155 |     |     |     |     | 160 |     |

| cgc | cag | atc | gtc | gat | ctt | ttc | tcg | ccc | acg | aac | ttc | ttc | ggc | acc | aat | 528 |
|-----|-----|-----|-----|-----|-----|-----|-----|-----|-----|-----|-----|-----|-----|-----|-----|-----|
| Arg | Gln | Ile | Val | Asp | Leu | Phe | Ser | Pro | Thr | Asn | Phe | Phe | Gly | Thr | Asn |     |
|     |     |     |     | 165 |     |     |     |     | 170 |     |     |     |     | 175 |     |     |

| ccc | gac | gcg | ctc | gaa | cgc | gcc | atc | gcc | acc | gac | ggc | gag | agc | ctg | gtg | 576 |
|-----|-----|-----|-----|-----|-----|-----|-----|-----|-----|-----|-----|-----|-----|-----|-----|-----|
| Pro | Asp | Ala | Leu | Glu | Arg | Ala | Ile | Ala | Thr | Asp | Gly | Glu | Ser | Leu | Val |     |
|     |     |     | 180 |     |     |     |     | 185 |     |     |     |     | 190 |     |     |     |

| cag | ggg | ctg | gag | aat | ctc | gtg | cgc | gac | atc | gag | gcc | aac | aac | ggc | gat | 624 |
|-----|-----|-----|-----|-----|-----|-----|-----|-----|-----|-----|-----|-----|-----|-----|-----|-----|
| Gln | Gly | Leu | Glu | Asn | Leu | Val | Arg | Asp | Ile | Glu | Ala | Asn | Asn | Gly | Asp |     |
|     |     |     | 195 |     |     |     |     | 200 |     |     |     |     | 205 |     |     |     |

| ctg | ctc | gtc | acg | ctg | gcc | gac | ccc | gag | gcc | ttt | cag | gtg | ggg | cag | aac | 672 |
|-----|-----|-----|-----|-----|-----|-----|-----|-----|-----|-----|-----|-----|-----|-----|-----|-----|
| Leu | Leu | Val | Thr | Leu | Ala | Asp | Pro | Glu | Ala | Phe | Gln | Val | Gly | Gln | Asn |     |
|     | 210 |     |     |     |     | 215 |     |     |     |     | 220 |     |     |     |     |     |

| ctc | gcc | acc | acc | gaa | ggg | tcg | gtc | gtc | tac | cgc | aac | cgc | atg | ttc | gag | 720 |
|-----|-----|-----|-----|-----|-----|-----|-----|-----|-----|-----|-----|-----|-----|-----|-----|-----|
| Leu | Ala | Thr | Thr | Glu | Gly | Ser | Val | Val | Tyr | Arg | Asn | Arg | Met | Phe | Glu |     |
| 225 |     |     |     |     | 230 |     |     |     |     | 235 |     |     |     |     | 240 |     |

| ctg | atc | cag | tac | aag | ccc | acg | acc | gag | acg | gtc | cac | gag | acg | ccg | ctg | 768 |
|-----|-----|-----|-----|-----|-----|-----|-----|-----|-----|-----|-----|-----|-----|-----|-----|-----|
| Leu | Ile | Gln | Tyr | Lys | Pro | Thr | Thr | Glu | Thr | Val | His | Glu | Thr | Pro | Leu |     |
|     |     |     |     | 245 |     |     |     |     | 250 |     |     |     |     | 255 |     |     |

| ctg | atc | ttt | ccg | ccc | tgg | atc | aac | aag | ttc | tac | atc | ctc | gac | ctc | aag | 816 |
|-----|-----|-----|-----|-----|-----|-----|-----|-----|-----|-----|-----|-----|-----|-----|-----|-----|
| Leu | Ile | Phe | Pro | Pro | Trp | Ile | Asn | Lys | Phe | Tyr | Ile | Leu | Asp | Leu | Lys |     |
|     |     |     | 260 |     |     |     |     | 265 |     |     |     |     | 270 |     |     |     |

| ccg | cag | aat | tcc | ctg | ctg | aag | tgg | ctg | gtg | gat | cag | ggc | ttc | acg | gtc | 864 |
|-----|-----|-----|-----|-----|-----|-----|-----|-----|-----|-----|-----|-----|-----|-----|-----|-----|
| Pro | Gln | Asn | Ser | Leu | Leu | Lys | Trp | Leu | Val | Asp | Gln | Gly | Phe | Thr | Val |     |
|     |     | 275 |     |     |     |     | 280 |     |     |     |     | 285 |     |     |     |     |

| ttc | gtc | gtc | tcg | tgg | gtg | aac | ccc | gac | aag | agc | tat | gcc | ggc | atc | ggc | 912 |
|-----|-----|-----|-----|-----|-----|-----|-----|-----|-----|-----|-----|-----|-----|-----|-----|-----|
| Phe | Val | Val | Ser | Trp | Val | Asn | Pro | Asp | Lys | Ser | Tyr | Ala | Gly | Ile | Gly |     |
|     | 290 |     |     |     |     | 295 |     |     |     |     | 300 |     |     |     |     |     |

| atg | gac | gac | tac | atc | cgc | gaa | ggc | tac | atg | cgc | gcc | atg | gcc | gag | gtg | 960 |
|-----|-----|-----|-----|-----|-----|-----|-----|-----|-----|-----|-----|-----|-----|-----|-----|-----|
| Met | Asp | Asp | Tyr | Ile | Arg | Glu | Gly | Tyr | Met | Arg | Ala | Met | Ala | Glu | Val |     |
| 305 |     |     |     |     | 310 |     |     |     |     | 315 |     |     |     |     | 320 |     |

| cgc | tcg | atc | acc | cgg | cag | aag | cag | atc | aac | gcg | gta | ggc | tat | tgc | atc | 1008 |
|-----|-----|-----|-----|-----|-----|-----|-----|-----|-----|-----|-----|-----|-----|-----|-----|------|
| Arg | Ser | Ile | Thr | Arg | Gln | Lys | Gln | Ile | Asn | Ala | Val | Gly | Tyr | Cys | Ile |      |
|     |     |     |     | 325 |     |     |     |     | 330 |     |     |     |     | 335 |     |      |

| gcg | ggc | acc | acg | ctc | acg | ctg | acg | ctg | gcg | cac | ctg | cag | aag | gcg | ggc | 1056 |
|-----|-----|-----|-----|-----|-----|-----|-----|-----|-----|-----|-----|-----|-----|-----|-----|------|
| Ala | Gly | Thr | Thr | Leu | Thr | Leu | Thr | Leu | Ala | His | Leu | Gln | Lys | Ala | Gly |      |
|     |     |     | 340 |     |     |     |     | 345 |     |     |     |     | 350 |     |     |      |

| gat | ccg | tcc | gta | cgc | tcg | gcc | acc | ttc | ttc | acc | acg | ctc | acc | gac | ttt | 1104 |
|-----|-----|-----|-----|-----|-----|-----|-----|-----|-----|-----|-----|-----|-----|-----|-----|------|
| Asp | Pro | Ser | Val | Arg | Ser | Ala | Thr | Phe | Phe | Thr | Thr | Leu | Thr | Asp | Phe |      |
|     |     | 355 |     |     |     |     | 360 |     |     |     |     | 365 |     |     |     |      |

| tcg | gac | ccg | ggt | gag | gtg | ggg | gtg | ttc | ctc | aac | gac | gat | ttc | gtc | gac | 1152 |
|-----|-----|-----|-----|-----|-----|-----|-----|-----|-----|-----|-----|-----|-----|-----|-----|------|
| Ser | Asp | Pro | Gly | Glu | Val | Gly | Val | Phe | Leu | Asn | Asp | Asp | Phe | Val | Asp |      |
| 370 |     |     |     |     | 375 |     |     |     |     | 380 |     |     |     |     |     |      |

| ggg | atc | gag | cgg | cag | gtg | gcg | gtg | gac | ggg | atc | ctc | gac | aag | acc | ttc | 1200 |
|-----|-----|-----|-----|-----|-----|-----|-----|-----|-----|-----|-----|-----|-----|-----|-----|------|
| Gly | Ile | Glu | Arg | Gln | Val | Ala | Val | Asp | Gly | Ile | Leu | Asp | Lys | Thr | Phe |      |
| 385 |     |     |     |     | 390 |     |     |     |     | 395 |     |     |     |     | 400 |      |

| atg | tcg | cgc | acc | ttc | agc | tat | ctg | cgg | tcg | aac | gac | ctg | atc | tat | cag | 1248 |
|-----|-----|-----|-----|-----|-----|-----|-----|-----|-----|-----|-----|-----|-----|-----|-----|------|
| Met | Ser | Arg | Thr | Phe | Ser | Tyr | Leu | Arg | Ser | Asn | Asp | Leu | Ile | Tyr | Gln |      |
|     |     |     |     | 405 |     |     |     |     | 410 |     |     |     |     | 415 |     |      |

| ccg | gcg | atc | aag | agc | tac | atg | atg | ggc | gag | gcg | ccg | ccg | gcc | ttc | gac | 1296 |
|-----|-----|-----|-----|-----|-----|-----|-----|-----|-----|-----|-----|-----|-----|-----|-----|------|
| Pro | Ala | Ile | Lys | Ser | Tyr | Met | Met | Gly | Glu | Ala | Pro | Pro | Ala | Phe | Asp |      |
|     |     | 420 |     |     |     |     | 425 |     |     |     |     | 430 |     |     |     |      |

| ctg | ctc | tac | tgg | aac | gga | gac | ggc | acc | aac | ctg | ccg | gcg | cag | atg | gcg | 1344 |

```
Leu Leu Tyr Trp Asn Gly Asp Gly Thr Asn Leu Pro Ala Gln Met Ala
            435                 440                 445 gtc gaa tac ctg cgt ggc ctg tgc cag cag gac cgg ctg gcg ggc ggc      1392
Val Glu Tyr Leu Arg Gly Leu Cys Gln Gln Asp Arg Leu Ala Gly Gly
    450                 455                 460 acc ttc ccg gtg ctg ggc tcg ccc gtg ggg ctg aag gat gtg acg ctt      1440
Thr Phe Pro Val Leu Gly Ser Pro Val Gly Leu Lys Asp Val Thr Leu
465                 470                 475                 480 ccc gtc tgc gcc atc gcc tgc gag acc gac cat atc gcg ccg tgg aaa      1488
Pro Val Cys Ala Ile Ala Cys Glu Thr Asp His Ile Ala Pro Trp Lys
                485                 490                 495 agc agc ttc aac ggc ttc cgt cag ttc ggc tcg acc gac aag acc ttc      1536
Ser Ser Phe Asn Gly Phe Arg Gln Phe Gly Ser Thr Asp Lys Thr Phe
            500                 505                 510 att ctc tct caa tcg ggc cat gtg gcg ggc atc gtg aac ccg ccc agc      1584
Ile Leu Ser Gln Ser Gly His Val Ala Gly Ile Val Asn Pro Pro Ser
        515                 520                 525 cgc aac aaa tac ggc cat tac acc aac gag ggc ccg gcc ggc acg ccg      1632
Arg Asn Lys Tyr Gly His Tyr Thr Asn Glu Gly Pro Ala Gly Thr Pro
    530                 535                 540 gag tcg ttc cgg gag ggg gcc gag ttc cac gcg ggc tcc tgg tgg ccg      1680
Glu Ser Phe Arg Glu Gly Ala Glu Phe His Ala Gly Ser Trp Trp Pro
545                 550                 555                 560 cgc tgg ggc gcc tgg ctc gcc gag cga tcg ggc aag cag gtc ccg gcg      1728
Arg Trp Gly Ala Trp Leu Ala Glu Arg Ser Gly Lys Gln Val Pro Ala
                565                 570                 575 cgc cag ccg ggc gat tcg aaa cat ccc gag ctc gcg ccg gcg ccc gga      1776
Arg Gln Pro Gly Asp Ser Lys His Pro Glu Leu Ala Pro Ala Pro Gly
            580                 585                 590 tcc tat gtg gcg gcg gtg ggc ggg gct tga                              1806
Ser Tyr Val Ala Ala Val Gly Gly Ala
        595                 600

<210> SEQ ID NO 12
<211> LENGTH: 601
<212> TYPE: PRT
<213> ORGANISM: Rhodobacter sphaeroides

<400> SEQUENCE: 12

Met Ala Thr Glu Glu Gln Ser Pro Gly Ser Gly Arg Asp Ala Gln Phe
1               5                   10                  15

Glu Arg Leu Asn Ala Asn Leu Thr Arg Ile Asp Glu Leu Ser Lys Arg
            20                  25                  30

Leu Thr Ala Ala Leu Thr Lys Arg Lys Leu Ser Asp Pro Ala Leu His
        35                  40                  45

Gly Pro Ser Gly Asp Val Phe Leu Lys Ala Met Thr Ala Tyr Met Ala
    50                  55                  60

Glu Met Met Gln Asn Pro Ala Lys Ile Leu Glu His Gln Ile Ser Phe
65                  70                  75                  80

Trp Gly Lys Ser Leu Lys His Tyr Val Glu Ala Gln His Gln Leu Val
            85                  90                  95

Lys Gly Glu Leu Lys Pro Pro Asp Val Thr Pro Lys Asp Arg Arg
        100                 105                 110

Phe Ser Asn Pro Leu Trp Gln Thr His Pro Phe Phe Asn Tyr Leu Lys
    115                 120                 125

Gln Gln Tyr Leu Met Asn Ala Glu Ala Val Asn Gln Ala Val Glu Ala
    130                 135                 140

Leu Glu His Ile Glu Pro Ser Asp Lys Lys Arg Val Glu Tyr Phe Ser
```

-continued

```
        145                 150                 155                 160
Arg Gln Ile Val Asp Leu Phe Ser Pro Thr Asn Phe Phe Gly Thr Asn
                        165                 170                 175
Pro Asp Ala Leu Glu Arg Ala Ile Ala Thr Asp Gly Glu Ser Leu Val
                        180                 185                 190
Gln Gly Leu Glu Asn Leu Val Arg Asp Ile Glu Ala Asn Asn Gly Asp
                        195                 200                 205
Leu Leu Val Thr Leu Ala Asp Pro Glu Ala Phe Gln Val Gly Gln Asn
        210                 215                 220
Leu Ala Thr Thr Glu Gly Ser Val Val Tyr Arg Asn Arg Met Phe Glu
225                 230                 235                 240
Leu Ile Gln Tyr Lys Pro Thr Thr Glu Thr Val His Glu Thr Pro Leu
                        245                 250                 255
Leu Ile Phe Pro Pro Trp Ile Asn Lys Phe Tyr Ile Leu Asp Leu Lys
                        260                 265                 270
Pro Gln Asn Ser Leu Leu Lys Trp Leu Val Asp Gln Gly Phe Thr Val
                        275                 280                 285
Phe Val Val Ser Trp Val Asn Pro Asp Lys Ser Tyr Ala Gly Ile Gly
        290                 295                 300
Met Asp Asp Tyr Ile Arg Glu Gly Tyr Met Arg Ala Met Ala Glu Val
305                 310                 315                 320
Arg Ser Ile Thr Arg Gln Lys Gln Ile Asn Ala Val Gly Tyr Cys Ile
                        325                 330                 335
Ala Gly Thr Thr Leu Thr Leu Thr Leu Ala His Leu Gln Lys Ala Gly
                        340                 345                 350
Asp Pro Ser Val Arg Ser Ala Thr Phe Phe Thr Thr Leu Thr Asp Phe
                        355                 360                 365
Ser Asp Pro Gly Glu Val Gly Val Phe Leu Asn Asp Asp Phe Val Asp
        370                 375                 380
Gly Ile Glu Arg Gln Val Ala Val Asp Gly Ile Leu Asp Lys Thr Phe
385                 390                 395                 400
Met Ser Arg Thr Phe Ser Tyr Leu Arg Ser Asn Asp Leu Ile Tyr Gln
                        405                 410                 415
Pro Ala Ile Lys Ser Tyr Met Met Gly Glu Ala Pro Pro Ala Phe Asp
                        420                 425                 430
Leu Leu Tyr Trp Asn Gly Asp Gly Thr Asn Leu Pro Ala Gln Met Ala
                        435                 440                 445
Val Glu Tyr Leu Arg Gly Leu Cys Gln Gln Asp Arg Leu Ala Gly Gly
        450                 455                 460
Thr Phe Pro Val Leu Gly Ser Pro Val Gly Leu Lys Asp Val Thr Leu
465                 470                 475                 480
Pro Val Cys Ala Ile Ala Cys Glu Thr Asp His Ile Ala Pro Trp Lys
                        485                 490                 495
Ser Ser Phe Asn Gly Phe Arg Gln Phe Gly Ser Thr Asp Lys Thr Phe
                        500                 505                 510
Ile Leu Ser Gln Ser Gly His Val Ala Gly Ile Val Asn Pro Pro Ser
                        515                 520                 525
Arg Asn Lys Tyr Gly His Tyr Thr Asn Glu Gly Pro Ala Gly Thr Pro
        530                 535                 540
Glu Ser Phe Arg Glu Gly Ala Glu Phe His Ala Gly Ser Trp Trp Pro
545                 550                 555                 560
Arg Trp Gly Ala Trp Leu Ala Glu Arg Ser Gly Lys Gln Val Pro Ala
                        565                 570                 575
```

-continued

```
        Arg Gln Pro Gly Asp Ser Lys His Pro Glu Leu Ala Pro Ala Pro Gly
                    580                 585                 590

Ser Tyr Val Ala Ala Val Gly Gly Ala
                    595                 600

<210> SEQ ID NO 13
<211> LENGTH: 1911
<212> TYPE: DNA
<213> ORGANISM: Rhizobium etli
<220> FEATURE:
<221> NAME/KEY: CDS
<222> LOCATION: (1)..(1911)

<400> SEQUENCE: 13 atg tac aac aaa cgg ata aaa aga gtg ctg ccg ccg gag gaa atg gtg        48
Met Tyr Asn Lys Arg Ile Lys Arg Val Leu Pro Pro Glu Glu Met Val
1               5                   10                  15 acc gac agc aag cag gag agt ggc ggc cag aaa aat ggc gac aag acc       96
Thr Asp Ser Lys Gln Glu Ser Gly Gly Gln Lys Asn Gly Asp Lys Thr
            20                  25                  30 ggt ttc gac gcg acc gat ctc aaa ccc tat ctg ttg aag gat ccc gag       144
Gly Phe Asp Ala Thr Asp Leu Lys Pro Tyr Leu Leu Lys Asp Pro Glu
        35                  40                  45 acc atg gcg atg aat ttc gcc cgg gcg ctc gaa aat ctc ggc cag gcc       192
Thr Met Ala Met Asn Phe Ala Arg Ala Leu Glu Asn Leu Gly Gln Ala
    50                  55                  60 gcc tcg gcc tgg ctt gcg ccg cgc gaa cgc ggc gag atc acc gaa acg       240
Ala Ser Ala Trp Leu Ala Pro Arg Glu Arg Gly Glu Ile Thr Glu Thr
65                  70                  75                  80 gcc atc gat ccg atg acc gac atg gtc aag acg ctt tcc aag atc agc       288
Ala Ile Asp Pro Met Thr Asp Met Val Lys Thr Leu Ser Lys Ile Ser
                85                  90                  95 gaa tac tgg att tcc gat ccc cgc cgc acc ttc gag gcg cag act cag       336
Glu Tyr Trp Ile Ser Asp Pro Arg Arg Thr Phe Glu Ala Gln Thr Gln
            100                 105                 110 ctg atg tcg tcc ttc ttc ggc atc tgg atg cgc tcg atg cag cgc atg       384
Leu Met Ser Ser Phe Phe Gly Ile Trp Met Arg Ser Met Gln Arg Met
        115                 120                 125 cag ggc acg cgt ggg atg cag ggc gag ccc ctg ccg ccc gag ccc gac       432
Gln Gly Thr Arg Gly Met Gln Gly Glu Pro Leu Pro Pro Glu Pro Asp
    130                 135                 140 acc cgc aag gac aag cgc ttt tcg gat gag gat tgg cag aaa aat ccg       480
Thr Arg Lys Asp Lys Arg Phe Ser Asp Glu Asp Trp Gln Lys Asn Pro
145                 150                 155                 160 ttc ttc gat ttc ctc cgc cag gtc tat ttc gtc acg agt gac tgg gtg       528
Phe Phe Asp Phe Leu Arg Gln Val Tyr Phe Val Thr Ser Asp Trp Val
                165                 170                 175 gac aag ctg gtg tcg gag acc gac ggc ctc gac gag cac acc aag cac       576
Asp Lys Leu Val Ser Glu Thr Asp Gly Leu Asp Glu His Thr Lys His
            180                 185                 190 aag gcg gga ttc tac gtg aag cag atc acg gca gcc ctt tcg ccg agc       624
Lys Ala Gly Phe Tyr Val Lys Gln Ile Thr Ala Ala Leu Ser Pro Ser
        195                 200                 205 aac ttc atc gct acc aac cca cag ctt tat cgc gag acc atc gcg agc       672
Asn Phe Ile Ala Thr Asn Pro Gln Leu Tyr Arg Glu Thr Ile Ala Ser
    210                 215                 220 aac ggc gaa aac ctg gtg cgc ggc atg aaa atg ctc gcc gag gac att       720
Asn Gly Glu Asn Leu Val Arg Gly Met Lys Met Leu Ala Glu Asp Ile
225                 230                 235                 240 gct gcc gga aag ggc gag ctt cgc ctt cgc cag acc gac atg acg aaa       768
```

```
          Ala Ala Gly Lys Gly Glu Leu Arg Leu Arg Gln Thr Asp Met Thr Lys
                      245                 250                 255 ttc gcc gtc ggg cgc gac atg gcg ttg acg ccg ggc aag gtg atc gcc          816
Phe Ala Val Gly Arg Asp Met Ala Leu Thr Pro Gly Lys Val Ile Ala
            260                 265                 270 cag aac gat atc tgc cag atc atc cag tac gaa gcc tcg acc gag acg          864
Gln Asn Asp Ile Cys Gln Ile Ile Gln Tyr Glu Ala Ser Thr Glu Thr
                275                 280                 285 gtg ctg aaa cgg cca ttg ctg atc tgc ccg ccc tgg atc aac aag ttc          912
Val Leu Lys Arg Pro Leu Leu Ile Cys Pro Pro Trp Ile Asn Lys Phe
        290                 295                 300 tac att ctc gac ctc aac ccg cag aaa tcc ttc atc aaa tgg tgc gtc          960
Tyr Ile Leu Asp Leu Asn Pro Gln Lys Ser Phe Ile Lys Trp Cys Val
305                 310                 315                 320 gac cag ggg cag acg gtc ttc gtc att tcc tgg gtc aac ccg gat ggg         1008
Asp Gln Gly Gln Thr Val Phe Val Ile Ser Trp Val Asn Pro Asp Gly
                    325                 330                 335 cgc cac gcc gag aag gac tgg gcc gcc tat gcc cga gag ggc atc gat         1056
Arg His Ala Glu Lys Asp Trp Ala Ala Tyr Ala Arg Glu Gly Ile Asp
                340                 345                 350 ttc gcg ctg gag acg atc gaa aag gcg acc ggg gag aag gag gtc aac         1104
Phe Ala Leu Glu Thr Ile Glu Lys Ala Thr Gly Glu Lys Glu Val Asn
            355                 360                 365 gcc gtc ggc tac tgt gtc ggc ggc acg ttg ctc gcg gca acg ctg gcg         1152
Ala Val Gly Tyr Cys Val Gly Gly Thr Leu Leu Ala Ala Thr Leu Ala
        370                 375                 380 ctg cac gca aag gag aag aac aag cgg atc aag acc gcc acg ctc ttc         1200
Leu His Ala Lys Glu Lys Asn Lys Arg Ile Lys Thr Ala Thr Leu Phe
385                 390                 395                 400 acc act cag gtc gat ttc acc cat gcg ggc gac ctc aag gtc ttc gtc         1248
Thr Thr Gln Val Asp Phe Thr His Ala Gly Asp Leu Lys Val Phe Val
                    405                 410                 415 gac gag gag caa ctg gcc gcg ctc gaa gag cat atg cag gcg gcc ggc         1296
Asp Glu Glu Gln Leu Ala Ala Leu Glu Glu His Met Gln Ala Ala Gly
                420                 425                 430 tat ctc gac ggt tcg aag atg tcg atg gct ttc aac atg ctg cgt gcg         1344
Tyr Leu Asp Gly Ser Lys Met Ser Met Ala Phe Asn Met Leu Arg Ala
            435                 440                 445 tcc gag ctg atc tgg cct tat ttc gtc aac agc tac ctc aag ggc cag         1392
Ser Glu Leu Ile Trp Pro Tyr Phe Val Asn Ser Tyr Leu Lys Gly Gln
        450                 455                 460 gag ccc ctg ccc ttc gac cta ttg ttc tgg aac gcc gat tcg acc cgc         1440
Glu Pro Leu Pro Phe Asp Leu Leu Phe Trp Asn Ala Asp Ser Thr Arg
465                 470                 475                 480 atg gcg gcg gca aac cat gcc ttc tac ctt cgc aat tgc tat ctt cgc         1488
Met Ala Ala Ala Asn His Ala Phe Tyr Leu Arg Asn Cys Tyr Leu Arg
                    485                 490                 495 aac gcg ctg acg cag aac gag atg att ctc gac ggc aag cgc ata tct         1536
Asn Ala Leu Thr Gln Asn Glu Met Ile Leu Asp Gly Lys Arg Ile Ser
                500                 505                 510 ctg aaa gac gtg aag atc ccg atc tat aat ctc gcc acg cgc gag gat         1584
Leu Lys Asp Val Lys Ile Pro Ile Tyr Asn Leu Ala Thr Arg Glu Asp
            515                 520                 525 cac atc gcc ccc gcc aag tcg gtt ttc ctc ggc agc cgg ttc ttc ggc         1632
His Ile Ala Pro Ala Lys Ser Val Phe Leu Gly Ser Arg Phe Phe Gly
        530                 535                 540 ggc aag gtg gaa ttt gtt gtc acc ggc tcg gga cat atc gcc ggc gtc         1680
Gly Lys Val Glu Phe Val Val Thr Gly Ser Gly His Ile Ala Gly Val
545                 550                 555                 560
```

-continued

```
gtc aac ccg ccc gac aag agg aaa tat caa ttc tgg acg ggc ggc ccg      1728
Val Asn Pro Pro Asp Lys Arg Lys Tyr Gln Phe Trp Thr Gly Gly Pro
                565                 570                 575 gcc aag ggc gaa tac gag acc tgg ctc gag cag gcg agc gag acg ccc      1776
Ala Lys Gly Glu Tyr Glu Thr Trp Leu Glu Gln Ala Ser Glu Thr Pro
            580                 585                 590 gga tca tgg tgg cca cat tgg caa gcc tgg ata gag acg cat gac ggc      1824
Gly Ser Trp Trp Pro His Trp Gln Ala Trp Ile Glu Thr His Asp Gly
        595                 600                 605 aga cgc gtt gca gcg cgc aag ccc ggc ggt gat gcg ctg aac gcg atc      1872
Arg Arg Val Ala Ala Arg Lys Pro Gly Gly Asp Ala Leu Asn Ala Ile
    610                 615                 620 gaa gaa gca ccg gga agt tat gtg atg gaa cgc acc tga                  1911
Glu Glu Ala Pro Gly Ser Tyr Val Met Glu Arg Thr
625                 630                 635

<210> SEQ ID NO 14
<211> LENGTH: 636
<212> TYPE: PRT
<213> ORGANISM: Rhizobium etli

<400> SEQUENCE: 14

Met Tyr Asn Lys Arg Ile Lys Arg Val Leu Pro Pro Glu Glu Met Val
1               5                   10                  15

Thr Asp Ser Lys Gln Glu Ser Gly Gly Gln Lys Asn Gly Asp Lys Thr
            20                  25                  30

Gly Phe Asp Ala Thr Asp Leu Lys Pro Tyr Leu Leu Lys Asp Pro Glu
        35                  40                  45

Thr Met Ala Met Asn Phe Ala Arg Ala Leu Glu Asn Leu Gly Gln Ala
    50                  55                  60

Ala Ser Ala Trp Leu Ala Pro Arg Glu Arg Gly Glu Ile Thr Glu Thr
65                  70                  75                  80

Ala Ile Asp Pro Met Thr Asp Met Val Lys Thr Leu Ser Lys Ile Ser
                85                  90                  95

Glu Tyr Trp Ile Ser Asp Pro Arg Arg Thr Phe Glu Ala Gln Thr Gln
            100                 105                 110

Leu Met Ser Ser Phe Phe Gly Ile Trp Met Arg Ser Met Gln Arg Met
        115                 120                 125

Gln Gly Thr Arg Gly Met Gln Gly Glu Pro Leu Pro Pro Glu Pro Asp
    130                 135                 140

Thr Arg Lys Asp Lys Arg Phe Ser Asp Glu Asp Trp Gln Lys Asn Pro
145                 150                 155                 160

Phe Phe Asp Phe Leu Arg Gln Val Tyr Phe Val Thr Ser Asp Trp Val
                165                 170                 175

Asp Lys Leu Val Ser Glu Thr Asp Gly Leu Asp Glu His Thr Lys His
            180                 185                 190

Lys Ala Gly Phe Tyr Val Lys Gln Ile Thr Ala Ala Leu Ser Pro Ser
        195                 200                 205

Asn Phe Ile Ala Thr Asn Pro Gln Leu Tyr Arg Glu Thr Ile Ala Ser
    210                 215                 220

Asn Gly Glu Asn Leu Val Arg Gly Met Lys Met Leu Ala Glu Asp Ile
225                 230                 235                 240

Ala Ala Gly Lys Gly Glu Leu Arg Leu Arg Gln Thr Asp Met Thr Lys
                245                 250                 255

Phe Ala Val Gly Arg Asp Met Ala Leu Thr Pro Gly Lys Val Ile Ala
            260                 265                 270
```

```
Gln Asn Asp Ile Cys Gln Ile Ile Gln Tyr Glu Ala Ser Thr Glu Thr
            275                 280                 285

Val Leu Lys Arg Pro Leu Leu Ile Cys Pro Pro Trp Ile Asn Lys Phe
290                 295                 300

Tyr Ile Leu Asp Leu Asn Pro Gln Lys Ser Phe Ile Lys Trp Cys Val
305                 310                 315                 320

Asp Gln Gly Gln Thr Val Phe Val Ile Ser Val Asn Pro Asp Gly
                325                 330                 335

Arg His Ala Glu Lys Asp Trp Ala Ala Tyr Ala Arg Glu Gly Ile Asp
            340                 345                 350

Phe Ala Leu Glu Thr Ile Glu Lys Ala Thr Gly Glu Lys Glu Val Asn
            355                 360                 365

Ala Val Gly Tyr Cys Val Gly Gly Thr Leu Leu Ala Ala Thr Leu Ala
            370                 375                 380

Leu His Ala Lys Glu Lys Asn Lys Arg Ile Lys Thr Ala Thr Leu Phe
385                 390                 395                 400

Thr Thr Gln Val Asp Phe Thr His Ala Gly Asp Leu Lys Val Phe Val
                405                 410                 415

Asp Glu Glu Gln Leu Ala Ala Leu Glu Glu His Met Gln Ala Ala Gly
                420                 425                 430

Tyr Leu Asp Gly Ser Lys Met Ser Met Ala Phe Asn Met Leu Arg Ala
            435                 440                 445

Ser Glu Leu Ile Trp Pro Tyr Phe Val Asn Ser Tyr Leu Lys Gly Gln
450                 455                 460

Glu Pro Leu Pro Phe Asp Leu Leu Phe Trp Asn Ala Asp Ser Thr Arg
465                 470                 475                 480

Met Ala Ala Ala Asn His Ala Phe Tyr Leu Arg Asn Cys Tyr Leu Arg
                485                 490                 495

Asn Ala Leu Thr Gln Asn Glu Met Ile Leu Asp Gly Lys Arg Ile Ser
            500                 505                 510

Leu Lys Asp Val Lys Ile Pro Ile Tyr Asn Leu Ala Thr Arg Glu Asp
            515                 520                 525

His Ile Ala Pro Ala Lys Ser Val Phe Leu Gly Ser Arg Phe Phe Gly
530                 535                 540

Gly Lys Val Glu Phe Val Val Thr Gly Ser Gly His Ile Ala Gly Val
545                 550                 555                 560

Val Asn Pro Pro Asp Lys Arg Lys Tyr Gln Phe Trp Thr Gly Gly Pro
                565                 570                 575

Ala Lys Gly Glu Tyr Glu Thr Trp Leu Glu Gln Ala Ser Glu Thr Pro
            580                 585                 590

Gly Ser Trp Trp Pro His Trp Gln Ala Trp Ile Glu Thr His Asp Gly
            595                 600                 605

Arg Arg Val Ala Ala Arg Lys Pro Gly Gly Asp Ala Leu Asn Ala Ile
610                 615                 620

Glu Glu Ala Pro Gly Ser Tyr Val Met Glu Arg Thr
625                 630                 635

<210> SEQ ID NO 15
<211> LENGTH: 1683
<212> TYPE: DNA
<213> ORGANISM: Pseudomonas sp. 61-3
<220> FEATURE:
<221> NAME/KEY: CDS
<222> LOCATION: (1)..(1683)

<400> SEQUENCE: 15
```

|  |  |
|---|---|
| atg aga gag aaa cca acg ccg ggc ttg ctg ccc aca ccc gcg acg ttc<br>Met Arg Glu Lys Pro Thr Pro Gly Leu Leu Pro Thr Pro Ala Thr Phe<br>1                        5                            10                         15 | 48 |
| atc aac gct cag agt gcg att acc ggt ctg cgc ggc cgg gat ctg ttc<br>Ile Asn Ala Gln Ser Ala Ile Thr Gly Leu Arg Gly Arg Asp Leu Phe<br>                      20                            25                            30 | 96 |
| tcg acc ctg cgc agc gtg gcc gcc cac ggc ctg cgt cac ccg gtg cgc<br>Ser Thr Leu Arg Ser Val Ala Ala His Gly Leu Arg His Pro Val Arg<br>        35                            40                            45 | 144 |
| agc gcc cgt cat gtt ctg gca ctg ggc ggc cag ttg ggc cgc gtg ctg<br>Ser Ala Arg His Val Leu Ala Leu Gly Gly Gln Leu Gly Arg Val Leu<br>        50                            55                            60 | 192 |
| ctg ggc gaa acg ctg cac acg ccg aac ccg aaa gac aat cgc ttt gcg<br>Leu Gly Glu Thr Leu His Thr Pro Asn Pro Lys Asp Asn Arg Phe Ala<br>65                      70                            75                            80 | 240 |
| gac ccg acc tgg aga ctg aat ccg ttt tac cgg cgc agc ctg cag gcc<br>Asp Pro Thr Trp Arg Leu Asn Pro Phe Tyr Arg Arg Ser Leu Gln Ala<br>                            85                            90                            95 | 288 |
| tat ctg agc tgg cag aaa cag gtc aaa agc tgg atc gat gaa agc ggc<br>Tyr Leu Ser Trp Gln Lys Gln Val Lys Ser Trp Ile Asp Glu Ser Gly<br>                      100                          105                          110 | 336 |
| atg agt gac gat gac cgc gcc cgc gcg cat ttc gtc ttc gca ctg ctc<br>Met Ser Asp Asp Asp Arg Ala Arg Ala His Phe Val Phe Ala Leu Leu<br>            115                          120                          125 | 384 |
| aat gac gcc gtg tcc ccc tcc aat acc ctg ctc aac ccg cta gcg atc<br>Asn Asp Ala Val Ser Pro Ser Asn Thr Leu Leu Asn Pro Leu Ala Ile<br>        130                          135                          140 | 432 |
| aag gag ctg ttc aac tcc ggt ggc aac agc ctg gtc cgc ggt ctc agc<br>Lys Glu Leu Phe Asn Ser Gly Gly Asn Ser Leu Val Arg Gly Leu Ser<br>145                    150                          155                          160 | 480 |
| cat tta ttc gac gac ctg atg cac aac aac ggg ctg ccc agt cag gtc<br>His Leu Phe Asp Asp Leu Met His Asn Asn Gly Leu Pro Ser Gln Val<br>                165                        170                          175 | 528 |
| acc aaa cac gcc ttc gag att ggc aag acc gtg gca acc acc gcc ggg<br>Thr Lys His Ala Phe Glu Ile Gly Lys Thr Val Ala Thr Thr Ala Gly<br>            180                          185                          190 | 576 |
| tcc gtg gtg ttt cgc aac gag ctg ctc gag ctg atg cag tac aag ccg<br>Ser Val Val Phe Arg Asn Glu Leu Leu Glu Leu Met Gln Tyr Lys Pro<br>                195                        200                          205 | 624 |
| atg agc gaa aaa cag tac gcc aag ccg ttg ctg atc gtc ccg ccg cag<br>Met Ser Glu Lys Gln Tyr Ala Lys Pro Leu Leu Ile Val Pro Pro Gln<br>        210                          215                          220 | 672 |
| att aac aag tac tac att ttc gac ctc agc ccg ggt aac agc ttc gtc<br>Ile Asn Lys Tyr Tyr Ile Phe Asp Leu Ser Pro Gly Asn Ser Phe Val<br>225                    230                          235                          240 | 720 |
| cag tac gca ttg aag aat ggt ctg cag gtg ttc gtg gtc agc tgg cgt<br>Gln Tyr Ala Leu Lys Asn Gly Leu Gln Val Phe Val Val Ser Trp Arg<br>                        245                          250                          255 | 768 |
| aac ccg gat gtt cgc cac cgc gaa tgg ggc ctg tcc agt tac gtt gag<br>Asn Pro Asp Val Arg His Arg Glu Trp Gly Leu Ser Ser Tyr Val Glu<br>                260                        265                          270 | 816 |
| gca ctg gaa gaa gca ctg aat gtt tgc cgc gct atc acc ggc gcg cgc<br>Ala Leu Glu Glu Ala Leu Asn Val Cys Arg Ala Ile Thr Gly Ala Arg<br>            275                          280                          285 | 864 |
| gac gtc aat ctg atg ggc gcc tgt gct ggc ggc ctg acc atc gcg gct<br>Asp Val Asn Leu Met Gly Ala Cys Ala Gly Gly Leu Thr Ile Ala Ala<br>        290                          295                          300 | 912 |
| ctg caa ggt cat ctg caa gcc aag cgg caa ctg cgg cgg gtc tcc agc<br>Leu Gln Gly His Leu Gln Ala Lys Arg Gln Leu Arg Arg Val Ser Ser | 960 |

```
gcc agc tac ctg gtc agc ctg ctg gat agc cag ata gac agc ccg gcg    1008
Ala Ser Tyr Leu Val Ser Leu Leu Asp Ser Gln Ile Asp Ser Pro Ala
            325                 330                 335 acg ttg ttc gcc gat gag cag acg ctg gaa gcc gcc aag cgc cat tcc    1056
Thr Leu Phe Ala Asp Glu Gln Thr Leu Glu Ala Ala Lys Arg His Ser
        340                 345                 350 tat caa cga ggt gtg ctc gag ggg cgc gac atg gcg aaa atc ttc gcc    1104
Tyr Gln Arg Gly Val Leu Glu Gly Arg Asp Met Ala Lys Ile Phe Ala
    355                 360                 365 tgg atg cgc ccc aat gac ctg atc tgg aac tac tgg gtc aac aac tac    1152
Trp Met Arg Pro Asn Asp Leu Ile Trp Asn Tyr Trp Val Asn Asn Tyr
370                 375                 380 ctg ctg ggc aaa gaa ccg ccg gcc ttc gac att ctg tat tgg aac agt    1200
Leu Leu Gly Lys Glu Pro Pro Ala Phe Asp Ile Leu Tyr Trp Asn Ser
385                 390                 395                 400 gac aac acg cgc ctg cca gcg gca ttc cat ggc gac ctg ctg gac ttc    1248
Asp Asn Thr Arg Leu Pro Ala Ala Phe His Gly Asp Leu Leu Asp Phe
                405                 410                 415 ttc aag cac aat ccg ctg act cac ccc ggc ggg ctg gag gtc tgt ggc    1296
Phe Lys His Asn Pro Leu Thr His Pro Gly Gly Leu Glu Val Cys Gly
            420                 425                 430 acg cct atc gat ttg cag aag gtc aac gta gac agc ttc agc gtg gcc    1344
Thr Pro Ile Asp Leu Gln Lys Val Asn Val Asp Ser Phe Ser Val Ala
        435                 440                 445 ggc atc aac gac cac atc act ccg tgg gac gcg gtg tac cgc tcg acc    1392
Gly Ile Asn Asp His Ile Thr Pro Trp Asp Ala Val Tyr Arg Ser Thr
    450                 455                 460 ctg ctg ctg ggt ggc gac cgg cgc ttc gta ctg tcc aac agc ggg cat    1440
Leu Leu Leu Gly Gly Asp Arg Arg Phe Val Leu Ser Asn Ser Gly His
465                 470                 475                 480 atc cag agc atc ctc aac ccg ccg agc aac ccc aag tcc aac tac atc    1488
Ile Gln Ser Ile Leu Asn Pro Pro Ser Asn Pro Lys Ser Asn Tyr Ile
                485                 490                 495 gag aac ccc aag ctc agt ggc gat cca cgc gcc tgg tat tac gac ggc    1536
Glu Asn Pro Lys Leu Ser Gly Asp Pro Arg Ala Trp Tyr Tyr Asp Gly
            500                 505                 510 acc cat gtc gaa ggt agc tgg tgg cca cgt tgg ctg agc tgg att cag    1584
Thr His Val Glu Gly Ser Trp Trp Pro Arg Trp Leu Ser Trp Ile Gln
        515                 520                 525 gag cgc tcc ggt acc caa cgc gaa acc ctg atg gcc ctt ggt aac cag    1632
Glu Arg Ser Gly Thr Gln Arg Glu Thr Leu Met Ala Leu Gly Asn Gln
    530                 535                 540 aac tat cca ccg atg gag gcg gcg cca ggt acc tac gtg cgc gtg cgc    1680
Asn Tyr Pro Pro Met Glu Ala Ala Pro Gly Thr Tyr Val Arg Val Arg
545                 550                 555                 560 tga                                                                1683
```

<210> SEQ ID NO 16
<211> LENGTH: 560
<212> TYPE: PRT
<213> ORGANISM: Pseudomonas sp. 61-3

<400> SEQUENCE: 16

```
Met Arg Glu Lys Pro Thr Pro Gly Leu Leu Pro Thr Pro Ala Thr Phe
1               5                   10                  15

Ile Asn Ala Gln Ser Ala Ile Thr Gly Leu Arg Gly Arg Asp Leu Phe
            20                  25                  30

Ser Thr Leu Arg Ser Val Ala Ala His Gly Leu Arg His Pro Val Arg
```

```
                35                  40                  45
Ser Ala Arg His Val Leu Ala Leu Gly Gly Gln Leu Gly Arg Val Leu
 50                  55                  60
Leu Gly Glu Thr Leu His Thr Pro Asn Pro Lys Asp Asn Arg Phe Ala
 65                  70                  75                  80
Asp Pro Thr Trp Arg Leu Asn Pro Phe Tyr Arg Arg Ser Leu Gln Ala
                 85                  90                  95
Tyr Leu Ser Trp Gln Lys Gln Val Lys Ser Trp Ile Asp Glu Ser Gly
                100                 105                 110
Met Ser Asp Asp Arg Ala Arg Ala His Phe Val Phe Ala Leu Leu
            115                 120                 125
Asn Asp Ala Val Ser Pro Ser Asn Thr Leu Leu Asn Pro Leu Ala Ile
130                 135                 140
Lys Glu Leu Phe Asn Ser Gly Asn Ser Leu Val Arg Gly Leu Ser
145                 150                 155                 160
His Leu Phe Asp Asp Leu Met His Asn Asn Gly Leu Pro Ser Gln Val
                165                 170                 175
Thr Lys His Ala Phe Glu Ile Gly Lys Thr Val Ala Thr Ala Gly
            180                 185                 190
Ser Val Val Phe Arg Asn Glu Leu Glu Leu Met Gln Tyr Lys Pro
            195                 200                 205
Met Ser Glu Lys Gln Tyr Ala Lys Pro Leu Leu Ile Val Pro Pro Gln
210                 215                 220
Ile Asn Lys Tyr Tyr Ile Phe Asp Leu Ser Pro Gly Asn Ser Phe Val
225                 230                 235                 240
Gln Tyr Ala Leu Lys Asn Gly Leu Gln Val Phe Val Ser Trp Arg
                245                 250                 255
Asn Pro Asp Val Arg His Arg Glu Trp Gly Leu Ser Ser Tyr Val Glu
                260                 265                 270
Ala Leu Glu Glu Ala Leu Asn Val Cys Arg Ala Ile Thr Gly Ala Arg
            275                 280                 285
Asp Val Asn Leu Met Gly Ala Cys Ala Gly Gly Leu Thr Ile Ala Ala
            290                 295                 300
Leu Gln Gly His Leu Gln Ala Lys Arg Gln Leu Arg Arg Val Ser Ser
305                 310                 315                 320
Ala Ser Tyr Leu Val Ser Leu Leu Asp Ser Gln Ile Asp Ser Pro Ala
                325                 330                 335
Thr Leu Phe Ala Asp Glu Gln Thr Leu Glu Ala Ala Lys Arg His Ser
                340                 345                 350
Tyr Gln Arg Gly Val Leu Glu Gly Arg Asp Met Ala Lys Ile Phe Ala
            355                 360                 365
Trp Met Arg Pro Asn Asp Leu Ile Trp Asn Tyr Val Asn Asn Tyr
            370                 375                 380
Leu Leu Gly Lys Glu Pro Pro Ala Phe Asp Ile Leu Tyr Trp Asn Ser
385                 390                 395                 400
Asp Asn Thr Arg Leu Pro Ala Ala Phe His Gly Asp Leu Leu Asp Phe
                405                 410                 415
Phe Lys His Asn Pro Leu Thr His Pro Gly Gly Leu Glu Val Cys Gly
                420                 425                 430
Thr Pro Ile Asp Leu Gln Lys Val Asn Val Asp Ser Phe Ser Val Ala
            435                 440                 445
Gly Ile Asn Asp His Ile Thr Pro Trp Asp Ala Val Tyr Arg Ser Thr
            450                 455                 460
```

```
Leu Leu Leu Gly Gly Asp Arg Arg Phe Val Leu Ser Asn Ser Gly His
465                 470                 475                 480

Ile Gln Ser Ile Leu Asn Pro Pro Ser Asn Pro Lys Ser Asn Tyr Ile
            485                 490                 495

Glu Asn Pro Lys Leu Ser Gly Asp Pro Arg Ala Trp Tyr Tyr Asp Gly
        500                 505                 510

Thr His Val Glu Gly Ser Trp Trp Pro Arg Trp Leu Ser Trp Ile Gln
            515                 520                 525

Glu Arg Ser Gly Thr Gln Arg Glu Thr Leu Met Ala Leu Gly Asn Gln
        530                 535                 540

Asn Tyr Pro Pro Met Glu Ala Pro Gly Thr Tyr Val Arg Val Arg
545                 550                 555                 560

<210> SEQ ID NO 17
<211> LENGTH: 1428
<212> TYPE: DNA
<213> ORGANISM: Haloarcula marismortui
<220> FEATURE:
<221> NAME/KEY: CDS
<222> LOCATION: (1)..(1428)

<400> SEQUENCE: 17
```

| | | | | | | | | | | | | | | | | |
|---|---|---|---|---|---|---|---|---|---|---|---|---|---|---|---|---|
| atg | tcc | agc | aac | ccc | ttc | aat | ccg | ttc | gag | gcc | gcg | ctc | aac | tgg | cag | 48 |
| Met | Ser | Ser | Asn | Pro | Phe | Asn | Pro | Phe | Glu | Ala | Ala | Leu | Asn | Trp | Gln | |
| 1 | | | | 5 | | | | | 10 | | | | | 15 | | |
| cga | aag | acg | ctg | gag | aac | atg | acc | gac | gcc | gct | gag | acc | agt | cag | gtc | 96 |
| Arg | Lys | Thr | Leu | Glu | Asn | Met | Thr | Asp | Ala | Ala | Glu | Thr | Ser | Gln | Val | |
| | | | 20 | | | | | 25 | | | | | 30 | | | |
| gcc | gat | gag | cga | ctg | gag | ctg | atg | gag | tcc | gtc | gac | gtc | ggc | cag | acg | 144 |
| Ala | Asp | Glu | Arg | Leu | Glu | Leu | Met | Glu | Ser | Val | Asp | Val | Gly | Gln | Thr | |
| | | | | 35 | | | | | 40 | | | | | 45 | | |
| ccc | agt | aac | gtc | gtc | tac | gag | gag | aac | aag | ctc | gaa | ctc | ctc | cac | tac | 192 |
| Pro | Ser | Asn | Val | Val | Tyr | Glu | Glu | Asn | Lys | Leu | Glu | Leu | Leu | His | Tyr | |
| | | 50 | | | | | 55 | | | | | 60 | | | | |
| gac | gcc | gaa | gcc | gct | ggc | att | gag | gtg | ccg | gac | gag | gag | aag | gaa | gac | 240 |
| Asp | Ala | Glu | Ala | Ala | Gly | Ile | Glu | Val | Pro | Asp | Glu | Glu | Lys | Glu | Asp | |
| 65 | | | | | 70 | | | | | 75 | | | | | 80 | |
| gtt | ccg | ata | ctc | atc | gtt | tac | gcg | ctc | atc | aac | cga | ccg | tac | atc | ctt | 288 |
| Val | Pro | Ile | Leu | Ile | Val | Tyr | Ala | Leu | Ile | Asn | Arg | Pro | Tyr | Ile | Leu | |
| | | | | 85 | | | | | 90 | | | | | 95 | | |
| gat | ctg | cag | gag | gag | cgg | tca | gtc | gtc | cga | cgc | ctg | ctt | gag | gcg | ggc | 336 |
| Asp | Leu | Gln | Glu | Glu | Arg | Ser | Val | Val | Arg | Arg | Leu | Leu | Glu | Ala | Gly | |
| | | | 100 | | | | | 105 | | | | | 110 | | | |
| cat | gac | gtg | tat | ctc | atc | gac | tgg | aac | gag | ccg | tcg | cgg | ctt | gac | cag | 384 |
| His | Asp | Val | Tyr | Leu | Ile | Asp | Trp | Asn | Glu | Pro | Ser | Arg | Leu | Asp | Gln | |
| | | | | 115 | | | | | 120 | | | | | 125 | | |
| cac | ctc | act | ctc | gat | gac | tac | gtt | aac | cgc | tac | atg | gac | aac | tgc | gtc | 432 |
| His | Leu | Thr | Leu | Asp | Asp | Tyr | Val | Asn | Arg | Tyr | Met | Asp | Asn | Cys | Val | |
| | | 130 | | | | | 135 | | | | | 140 | | | | |
| gac | gtg | gtc | cgc | gac | cgc | tcc | ggg | cag | gac | gcg | atc | aac | atc | ctc | ggc | 480 |
| Asp | Val | Val | Arg | Asp | Arg | Ser | Gly | Gln | Asp | Ala | Ile | Asn | Ile | Leu | Gly | |
| 145 | | | | | 150 | | | | | 155 | | | | | 160 | |
| tac | tgt | atg | ggc | ggc | acg | atg | tcg | gtg | atg | tac | acc | gca | ctc | cac | aag | 528 |
| Tyr | Cys | Met | Gly | Gly | Thr | Met | Ser | Val | Met | Tyr | Thr | Ala | Leu | His | Lys | |
| | | | | 165 | | | | | 170 | | | | | 175 | | |
| gag | aag | gtc | aac | acc | ctg | ggc | ctg | atg | gcc | gcc | gga | ctg | tgc | ttc | gac | 576 |
| Glu | Lys | Val | Asn | Thr | Leu | Gly | Leu | Met | Ala | Ala | Gly | Leu | Cys | Phe | Asp | |
| | | | 180 | | | | | 185 | | | | | 190 | | | |
| cac | act | ggc | ggc | gtc | ctc | gaa | gag | tgg | ggc | tcc | gag | gag | tac | tac | tcc | 624 |

```
                                                                         672
ccg cag gat gtc gtc gac acg ttc ggc aac gtc ccc gcg gat atg ctc
Pro Gln Asp Val Val Asp Thr Phe Gly Asn Val Pro Ala Asp Met Leu
210                 215                 220

720
gac atc ggc ttc gcg ctg atg gac ccc gtc gaa aac tac gtc acg aag
Asp Ile Gly Phe Ala Leu Met Asp Pro Val Glu Asn Tyr Val Thr Lys
225                 230                 235                 240

768
tac atc cgg ttc gcg gag aac atg gag aac gag ggc ttc gtc gag aac
Tyr Ile Arg Phe Ala Glu Asn Met Glu Asn Glu Gly Phe Val Glu Asn
            245                 250                 255

816
ttc ggc cgc atg gag cag tgg ctc ggt gac ggc atc gac gtg gcc ggc
Phe Gly Arg Met Glu Gln Trp Leu Gly Asp Gly Ile Asp Val Ala Gly
        260                 265                 270

864
gag gcc tac gtc cag ttc ctc gaa gac gtg tac cag gac aac aag ctc
Glu Ala Tyr Val Gln Phe Leu Glu Asp Val Tyr Gln Asp Asn Lys Leu
    275                 280                 285

912
tac aag aac gaa ctg gaa ctc gac ggc aag cac gtc gac ctg gac aac
Tyr Lys Asn Glu Leu Glu Leu Asp Gly Lys His Val Asp Leu Asp Asn
290                 295                 300

960
atc gac atg cct gtc ctc cag ctc atg ggt gag tac gac cac ctc atc
Ile Asp Met Pro Val Leu Gln Leu Met Gly Glu Tyr Asp His Leu Ile
305                 310                 315                 320

1008
ccg ccg gag gcc tcc aag ccg ttc aac gat gtc atc gcc agc gac gac
Pro Pro Glu Ala Ser Lys Pro Phe Asn Asp Val Ile Ala Ser Asp Asp
            325                 330                 335

1056
acg cga acc atc gag ttc tcg acg ggc cac atc ggt ctc tcc gtc tcg
Thr Arg Thr Ile Glu Phe Ser Thr Gly His Ile Gly Leu Ser Val Ser
        340                 345                 350

1104
tcg tcg acc cac gct gac ctc tgg ccc gag gtc gcc gag tgg tac tcc
Ser Ser Thr His Ala Asp Leu Trp Pro Glu Val Ala Glu Trp Tyr Ser
    355                 360                 365

1152
gag cgc agc acg ggg agc gag gaa gtc gat atc gag gtc gag tcc ccc
Glu Arg Ser Thr Gly Ser Glu Glu Val Asp Ile Glu Val Glu Ser Pro
370                 375                 380

1200
gaa gcg gcc gaa gac gac gcg gta gac cag tcg gaa ctc acc gac atc
Glu Ala Ala Glu Asp Asp Ala Val Asp Gln Ser Glu Leu Thr Asp Ile
385                 390                 395                 400

1248
gac gtt gac gcg acc gac gat gtc gat gcc gac gct acc gaa gac gat
Asp Val Asp Ala Thr Asp Asp Val Asp Ala Asp Ala Thr Glu Asp Asp
            405                 410                 415

1296
gcg acc gac gaa ccc gct gac gtg gat agc gtc tcc ggt atc ggc ccg
Ala Thr Asp Glu Pro Ala Asp Val Asp Ser Val Ser Gly Ile Gly Pro
        420                 425                 430

1344
acc tac gcc gaa cgg ctg cac gac gcc ggc att cac agc gtc gcg gac
Thr Tyr Ala Glu Arg Leu His Asp Ala Gly Ile His Ser Val Ala Asp
    435                 440                 445

1392
ctg gcc gag tac gac gcg gcc gac ctg gcc gac atc gcc gaa acc acc
Leu Ala Glu Tyr Asp Ala Ala Asp Leu Ala Asp Ile Ala Glu Thr Thr
450                 455                 460

1428
gaa tcc cga gca cag gac tgg ctc gat caa ctg taa
Glu Ser Arg Ala Gln Asp Trp Leu Asp Gln Leu
465                 470                 475
```

His Thr Gly Gly Val Leu Glu Glu Trp Gly Ser Glu Tyr Tyr Ser
    195                 200                 205

<210> SEQ ID NO 18
<211> LENGTH: 475
<212> TYPE: PRT
<213> ORGANISM: Haloarcula marismortui

<400> SEQUENCE: 18

```
Met Ser Ser Asn Pro Phe Asn Pro Phe Glu Ala Ala Leu Asn Trp Gln
1               5                   10                  15
Arg Lys Thr Leu Glu Asn Met Thr Asp Ala Ala Glu Thr Ser Gln Val
            20                  25                  30
Ala Asp Glu Arg Leu Glu Leu Met Glu Ser Val Asp Val Gly Gln Thr
        35                  40                  45
Pro Ser Asn Val Val Tyr Glu Glu Asn Lys Leu Glu Leu Leu His Tyr
    50                  55                  60
Asp Ala Glu Ala Ala Gly Ile Glu Val Pro Glu Glu Lys Glu Asp
65                      70                  75                  80
Val Pro Ile Leu Ile Val Tyr Ala Leu Ile Asn Arg Pro Tyr Ile Leu
                85                  90                  95
Asp Leu Gln Glu Glu Arg Ser Val Val Arg Arg Leu Leu Glu Ala Gly
            100                 105                 110
His Asp Val Tyr Leu Ile Asp Trp Asn Glu Pro Ser Arg Leu Asp Gln
        115                 120                 125
His Leu Thr Leu Asp Asp Tyr Val Asn Arg Tyr Met Asp Asn Cys Val
    130                 135                 140
Asp Val Val Arg Asp Arg Ser Gly Gln Asp Ala Ile Asn Ile Leu Gly
145                 150                 155                 160
Tyr Cys Met Gly Gly Thr Met Ser Val Met Tyr Thr Ala Leu His Lys
                165                 170                 175
Glu Lys Val Asn Thr Leu Gly Leu Met Ala Ala Gly Leu Cys Phe Asp
            180                 185                 190
His Thr Gly Gly Val Leu Glu Glu Trp Gly Ser Glu Glu Tyr Tyr Ser
        195                 200                 205
Pro Gln Asp Val Val Asp Thr Phe Gly Asn Val Pro Ala Asp Met Leu
    210                 215                 220
Asp Ile Gly Phe Ala Leu Met Asp Pro Val Glu Asn Tyr Val Thr Lys
225                 230                 235                 240
Tyr Ile Arg Phe Ala Glu Asn Met Glu Asn Glu Gly Phe Val Glu Asn
                245                 250                 255
Phe Gly Arg Met Glu Gln Trp Leu Gly Asp Gly Ile Asp Val Ala Gly
            260                 265                 270
Glu Ala Tyr Val Gln Phe Leu Glu Asp Val Tyr Gln Asp Asn Lys Leu
        275                 280                 285
Tyr Lys Asn Glu Leu Glu Leu Asp Gly Lys His Val Asp Leu Asp Asn
    290                 295                 300
Ile Asp Met Pro Val Leu Gln Leu Met Gly Glu Tyr Asp His Leu Ile
305                 310                 315                 320
Pro Pro Glu Ala Ser Lys Pro Phe Asn Asp Val Ile Ala Ser Asp
                325                 330                 335
Thr Arg Thr Ile Glu Phe Ser Thr Gly His Ile Gly Leu Ser Val Ser
            340                 345                 350
Ser Ser Thr His Ala Asp Leu Trp Pro Glu Val Ala Glu Trp Tyr Ser
        355                 360                 365
Glu Arg Ser Thr Gly Ser Glu Glu Val Asp Ile Glu Val Glu Ser Pro
    370                 375                 380
Glu Ala Ala Glu Asp Ala Val Asp Gln Ser Glu Leu Thr Asp Ile
385                 390                 395                 400
Asp Val Asp Ala Thr Asp Asp Val Asp Ala Asp Ala Thr Glu Asp Asp
                405                 410                 415
Ala Thr Asp Glu Pro Ala Asp Val Asp Ser Val Ser Gly Ile Gly Pro
```

```
                     420                 425                 430
Thr Tyr Ala Glu Arg Leu His Asp Ala Gly Ile His Ser Val Ala Asp
        435                 440                 445

Leu Ala Glu Tyr Asp Ala Ala Asp Leu Ala Asp Ile Ala Glu Thr Thr
    450                 455                 460

Glu Ser Arg Ala Gln Asp Trp Leu Asp Gln Leu
465                 470                 475

<210> SEQ ID NO 19
<211> LENGTH: 23
<212> TYPE: DNA
<213> ORGANISM: Artificial
<220> FEATURE:
<223> OTHER INFORMATION: Synthetic DNA

<400> SEQUENCE: 19
atgagaaaag tagaaatcat tac                                              23

<210> SEQ ID NO 20
<211> LENGTH: 30
<212> TYPE: DNA
<213> ORGANISM: Artificial
<220> FEATURE:
<223> OTHER INFORMATION: Synthetic DNA

<400> SEQUENCE: 20
ttattttttc agtcccatgg gaccgtcctg                                       30

<210> SEQ ID NO 21
<211> LENGTH: 20
<212> TYPE: DNA
<213> ORGANISM: Artificial
<220> FEATURE:
<223> OTHER INFORMATION: Synthetic DNA

<400> SEQUENCE: 21
tcagcgttgc aggatgtagg                                                  20

<210> SEQ ID NO 22
<211> LENGTH: 23
<212> TYPE: DNA
<213> ORGANISM: Artificial
<220> FEATURE:
<223> OTHER INFORMATION: Synthetic DNA

<400> SEQUENCE: 22
tccatgtctg acatgaagtg gaa                                              23

<210> SEQ ID NO 23
<211> LENGTH: 20
<212> TYPE: DNA
<213> ORGANISM: Artificial
<220> FEATURE:
<223> OTHER INFORMATION: Synthetic DNA

<400> SEQUENCE: 23
tgcgccgcag aaaatcaacc                                                  20

<210> SEQ ID NO 24
<211> LENGTH: 25
<212> TYPE: DNA
<213> ORGANISM: Artificial
<220> FEATURE:
<223> OTHER INFORMATION: Synthetic DNA
```

<400> SEQUENCE: 24
acaagtcaat atggcaaccg aagag                                    25

<210> SEQ ID NO 25
<211> LENGTH: 28
<212> TYPE: DNA
<213> ORGANISM: Artificial
<220> FEATURE:
<223> OTHER INFORMATION: Synthetic DNA

<400> SEQUENCE: 25
aggagatata catatggagg cgttcgcc                                 28

<210> SEQ ID NO 26
<211> LENGTH: 28
<212> TYPE: DNA
<213> ORGANISM: Artificial
<220> FEATURE:
<223> OTHER INFORMATION: Synthetic DNA

<400> SEQUENCE: 26
agatccaact caggacttct cgcgtacg                                 28

<210> SEQ ID NO 27
<211> LENGTH: 20
<212> TYPE: DNA
<213> ORGANISM: Artificial
<220> FEATURE:
<223> OTHER INFORMATION: Synthetic DNA

<400> SEQUENCE: 27
tttctcgttc ggtcacgatg                                          20

<210> SEQ ID NO 28
<211> LENGTH: 22
<212> TYPE: DNA
<213> ORGANISM: Artificial
<220> FEATURE:
<223> OTHER INFORMATION: Synthetic DNA

<400> SEQUENCE: 28
tcgctgtttc ttaggatgtc tc                                       22

<210> SEQ ID NO 29
<211> LENGTH: 20
<212> TYPE: DNA
<213> ORGANISM: Artificial
<220> FEATURE:
<223> OTHER INFORMATION: Synthetic DNA

<400> SEQUENCE: 29
ccgggctcga tgtttacgac                                          20

<210> SEQ ID NO 30
<211> LENGTH: 21
<212> TYPE: DNA
<213> ORGANISM: Artificial
<220> FEATURE:
<223> OTHER INFORMATION: Synthetic DNA

<400> SEQUENCE: 30
gacaagtgag tcgcccctat g                                        21

<210> SEQ ID NO 31
<211> LENGTH: 20

```
<212> TYPE: DNA
<213> ORGANISM: Artificial
<220> FEATURE:
<223> OTHER INFORMATION: Synthetic DNA

<400> SEQUENCE: 31
ttacgctagg gtagaggaag                                              20

<210> SEQ ID NO 32
<211> LENGTH: 20
<212> TYPE: DNA
<213> ORGANISM: Artificial
<220> FEATURE:
<223> OTHER INFORMATION: Synthetic DNA

<400> SEQUENCE: 32
atggaatcga atgagcagaa                                              20

<210> SEQ ID NO 33
<211> LENGTH: 20
<212> TYPE: DNA
<213> ORGANISM: Artificial
<220> FEATURE:
<223> OTHER INFORMATION: Synthetic DNA

<400> SEQUENCE: 33
gacaacgatt tgcacgtttc                                              20

<210> SEQ ID NO 34
<211> LENGTH: 20
<212> TYPE: DNA
<213> ORGANISM: Artificial
<220> FEATURE:
<223> OTHER INFORMATION: Synthetic DNA

<400> SEQUENCE: 34
acgattgcta cttccatgtc                                              20

<210> SEQ ID NO 35
<211> LENGTH: 20
<212> TYPE: DNA
<213> ORGANISM: Artificial
<220> FEATURE:
<223> OTHER INFORMATION: Synthetic DNA

<400> SEQUENCE: 35
atggcttgac gaaggagtgt                                              20

<210> SEQ ID NO 36
<211> LENGTH: 23
<212> TYPE: DNA
<213> ORGANISM: Artificial
<220> FEATURE:
<223> OTHER INFORMATION: Synthetic DNA

<400> SEQUENCE: 36
gggttttcat ccagtcttct tgg                                          23

<210> SEQ ID NO 37
<211> LENGTH: 27
<212> TYPE: DNA
<213> ORGANISM: Artificial
<220> FEATURE:
<223> OTHER INFORMATION: Synthetic DNA

<400> SEQUENCE: 37
```

```
atgagcaata atgcaaacga ccccaca                                              27

<210> SEQ ID NO 38
<211> LENGTH: 29
<212> TYPE: DNA
<213> ORGANISM: Artificial
<220> FEATURE:
<223> OTHER INFORMATION: Synthetic DNA

<400> SEQUENCE: 38
ggaatcctgc tgtccagtta ttcgttcag                                            29

<210> SEQ ID NO 39
<211> LENGTH: 22
<212> TYPE: DNA
<213> ORGANISM: Artificial
<220> FEATURE:
<223> OTHER INFORMATION: Synthetic DNA

<400> SEQUENCE: 39
gccgccgagg tactattatg ag                                                   22

<210> SEQ ID NO 40
<211> LENGTH: 20
<212> TYPE: DNA
<213> ORGANISM: Artificial
<220> FEATURE:
<223> OTHER INFORMATION: Synthetic DNA

<400> SEQUENCE: 40 aaagggcgc cgaattacag                                                       20

<210> SEQ ID NO 41
<211> LENGTH: 20
<212> TYPE: DNA
<213> ORGANISM: Artificial
<220> FEATURE:
<223> OTHER INFORMATION: Synthetic DNA

<400> SEQUENCE: 41
cgtaagtacg acagtcggtt                                                      20

<210> SEQ ID NO 42
<211> LENGTH: 20
<212> TYPE: DNA
<213> ORGANISM: Artificial
<220> FEATURE:
<223> OTHER INFORMATION: Synthetic DNA

<400> SEQUENCE: 42
gtcatgttct ccagcgtctt                                                      20

<210> SEQ ID NO 43
<211> LENGTH: 29
<212> TYPE: DNA
<213> ORGANISM: Artificial
<220> FEATURE:
<223> OTHER INFORMATION: Synthetic DNA

<400> SEQUENCE: 43
atggaatcga caaataaaac ctggacaga                                            29

<210> SEQ ID NO 44
<211> LENGTH: 27
<212> TYPE: DNA
<213> ORGANISM: Artificial
```

```
<220> FEATURE:
<223> OTHER INFORMATION: Synthetic DNA

<400> SEQUENCE: 44
aaaattttca ctgtcgttcc gatagcc                                              27

<210> SEQ ID NO 45
<211> LENGTH: 20
<212> TYPE: DNA
<213> ORGANISM: Artificial
<220> FEATURE:
<223> OTHER INFORMATION: Synthetic DNA

<400> SEQUENCE: 45
catttccagg agtcgttgtg                                                      20

<210> SEQ ID NO 46
<211> LENGTH: 20
<212> TYPE: DNA
<213> ORGANISM: Artificial
<220> FEATURE:
<223> OTHER INFORMATION: Synthetic DNA

<400> SEQUENCE: 46
ttgtgcgtaa atccattccc                                                      20

<210> SEQ ID NO 47
<211> LENGTH: 39
<212> TYPE: DNA
<213> ORGANISM: Artificial
<220> FEATURE:
<223> OTHER INFORMATION: Synthetic DNA

<400> SEQUENCE: 47
accagaaaat aaaaaatgat aaagaaggaa atcgaccaa                                 39

<210> SEQ ID NO 48
<211> LENGTH: 19
<212> TYPE: DNA
<213> ORGANISM: Artificial
<220> FEATURE:
<223> OTHER INFORMATION: Synthetic DNA

<400> SEQUENCE: 48
ttaattagaa cgctcttca                                                       19

<210> SEQ ID NO 49
<211> LENGTH: 21
<212> TYPE: DNA
<213> ORGANISM: Artificial
<220> FEATURE:
<223> OTHER INFORMATION: Synthetic DNA

<400> SEQUENCE: 49
ttgaattgtt tcaaaaacga a                                                    21

<210> SEQ ID NO 50
<211> LENGTH: 39
<212> TYPE: DNA
<213> ORGANISM: Artificial
<220> FEATURE:
<223> OTHER INFORMATION: Synthetic DNA

<400> SEQUENCE: 50
ttggtcgatt tccttcttta tcattttta ttttctggt                                  39
```

<210> SEQ ID NO 51
<211> LENGTH: 20
<212> TYPE: DNA
<213> ORGANISM: Artificial
<220> FEATURE:
<223> OTHER INFORMATION: Synthetic DNA

<400> SEQUENCE: 51
aatgttccac aggtacagtc                                              20

<210> SEQ ID NO 52
<211> LENGTH: 20
<212> TYPE: DNA
<213> ORGANISM: Artificial
<220> FEATURE:
<223> OTHER INFORMATION: Synthetic DNA

<400> SEQUENCE: 52
ccagcctaag gtttaacagg                                              20

<210> SEQ ID NO 53
<211> LENGTH: 20
<212> TYPE: DNA
<213> ORGANISM: Artificial
<220> FEATURE:
<223> OTHER INFORMATION: Synthetic DNA

<400> SEQUENCE: 53
cacttgaagg acggatcgct                                              20

<210> SEQ ID NO 54
<211> LENGTH: 20
<212> TYPE: DNA
<213> ORGANISM: Artificial
<220> FEATURE:
<223> OTHER INFORMATION: Synthetic DNA

<400> SEQUENCE: 54
tcgcttaccc cttctgcaac                                              20

<210> SEQ ID NO 55
<211> LENGTH: 21
<212> TYPE: DNA
<213> ORGANISM: Artificial
<220> FEATURE:
<223> OTHER INFORMATION: Synthetic DNA

<400> SEQUENCE: 55
ggcaggatca gcagatggtt c                                            21

<210> SEQ ID NO 56
<211> LENGTH: 20
<212> TYPE: DNA
<213> ORGANISM: Artificial
<220> FEATURE:
<223> OTHER INFORMATION: Synthetic DNA

<400> SEQUENCE: 56
gatgggcacg atcaaaccct                                              20

<210> SEQ ID NO 57
<211> LENGTH: 64
<212> TYPE: DNA
<213> ORGANISM: Artificial
<220> FEATURE:
<223> OTHER INFORMATION: Synthetic DNA

<400> SEQUENCE: 57
ccggttcgaa tctagaaata attttgttta actttaagaa ggagatatac atatgtctga    60
catg                                                                64

<210> SEQ ID NO 58
<211> LENGTH: 41
<212> TYPE: DNA
<213> ORGANISM: Artificial
<220> FEATURE:
<223> OTHER INFORMATION: Synthetic DNA

<400> SEQUENCE: 58
gaaccaggcg gaacctgcag agatccaact cagcgttgca g                        41

<210> SEQ ID NO 59
<211> LENGTH: 64
<212> TYPE: DNA
<213> ORGANISM: Artificial
<220> FEATURE:
<223> OTHER INFORMATION: Synthetic DNA

<400> SEQUENCE: 59
ccggttcgaa tctagaaata attttgttta actttaagaa ggagatatac atatggcaac    60
cgaa                                                                64

<210> SEQ ID NO 60
<211> LENGTH: 41
<212> TYPE: DNA
<213> ORGANISM: Artificial
<220> FEATURE:
<223> OTHER INFORMATION: Synthetic DNA

<400> SEQUENCE: 60
gaaccaggcg gaacctgcag agatccaact caagccccgc c                        41

<210> SEQ ID NO 61
<211> LENGTH: 57
<212> TYPE: DNA
<213> ORGANISM: Artificial
<220> FEATURE:
<223> OTHER INFORMATION: Synthetic DNA

<400> SEQUENCE: 61
tcgaatctag aaataatttt gtttaacttt aagaaggaga tatacatatg gaggcgt       57

<210> SEQ ID NO 62
<211> LENGTH: 32
<212> TYPE: DNA
<213> ORGANISM: Artificial
<220> FEATURE:
<223> OTHER INFORMATION: Synthetic DNA

<400> SEQUENCE: 62
ggaacctgca gagatccaac tcaggacttc tc                                  32

<210> SEQ ID NO 63
<211> LENGTH: 57
<212> TYPE: DNA
<213> ORGANISM: Artificial
<220> FEATURE:
<223> OTHER INFORMATION: Synthetic DNA

<400> SEQUENCE: 63
tcgaatctag aaataatttt gtttaacttt aagaaggaga tatacatatg tacaaca        57

<210> SEQ ID NO 64
<211> LENGTH: 31
<212> TYPE: DNA
<213> ORGANISM: Artificial
<220> FEATURE:
<223> OTHER INFORMATION: Synthetic DNA

<400> SEQUENCE: 64
ggaacctgca gagatccaac tcaggtgcgt t                                    31

<210> SEQ ID NO 65
<211> LENGTH: 64
<212> TYPE: DNA
<213> ORGANISM: Artificial
<220> FEATURE:
<223> OTHER INFORMATION: Synthetic DNA

<400> SEQUENCE: 65
ccggttcgaa tctagaaata attttgttta actttaagaa ggagatatac atatgtttac     60
gaca                                                                  64

<210> SEQ ID NO 66
<211> LENGTH: 41
<212> TYPE: DNA
<213> ORGANISM: Artificial
<220> FEATURE:
<223> OTHER INFORMATION: Synthetic DNA

<400> SEQUENCE: 66
gaaccaggcg gaacctgcag agatccaact cagatcctaa c                         41

<210> SEQ ID NO 67
<211> LENGTH: 64
<212> TYPE: DNA
<213> ORGANISM: Artificial
<220> FEATURE:
<223> OTHER INFORMATION: Synthetic DNA

<400> SEQUENCE: 67
ccggttcgaa tctagaaata attttgttta actttaagaa ggagatatac atatggccaa     60
tcag                                                                  64

<210> SEQ ID NO 68
<211> LENGTH: 37
<212> TYPE: DNA
<213> ORGANISM: Artificial
<220> FEATURE:
<223> OTHER INFORMATION: Synthetic DNA

<400> SEQUENCE: 68
caggcggaac ctgcagagat ccaactcacg taatcgc                              37

<210> SEQ ID NO 69
<211> LENGTH: 64
<212> TYPE: DNA
<213> ORGANISM: Artificial
<220> FEATURE:
<223> OTHER INFORMATION: Synthetic DNA

<400> SEQUENCE: 69
ccggttcgaa tctagaaata attttgttta actttaagaa ggagatatac atatggaatc     60
gaat                                                                  64

```
<210> SEQ ID NO 70
<211> LENGTH: 41
<212> TYPE: DNA
<213> ORGANISM: Artificial
<220> FEATURE:
<223> OTHER INFORMATION: Synthetic DNA

<400> SEQUENCE: 70
gaaccaggcg gaacctgcag agatccaacc taaatacgct t          41

<210> SEQ ID NO 71
<211> LENGTH: 64
<212> TYPE: DNA
<213> ORGANISM: Artificial
<220> FEATURE:
<223> OTHER INFORMATION: Synthetic DNA

<400> SEQUENCE: 71
ccggttcgaa tctagaaata attttgttta actttaagaa ggagatatac atatgcagca    60
gttc                                                                 64

<210> SEQ ID NO 72
<211> LENGTH: 41
<212> TYPE: DNA
<213> ORGANISM: Artificial
<220> FEATURE:
<223> OTHER INFORMATION: Synthetic DNA

<400> SEQUENCE: 72
gaaccaggcg gaacctgcag agatccaact cattgcaggc t          41

<210> SEQ ID NO 73
<211> LENGTH: 64
<212> TYPE: DNA
<213> ORGANISM: Artificial
<220> FEATURE:
<223> OTHER INFORMATION: Synthetic DNA

<400> SEQUENCE: 73
ccggttcgaa tctagaaata attttgttta actttaagaa ggagatatac atatgagaga    60
gaaa                                                                 64

<210> SEQ ID NO 74
<211> LENGTH: 41
<212> TYPE: DNA
<213> ORGANISM: Artificial
<220> FEATURE:
<223> OTHER INFORMATION: Synthetic DNA

<400> SEQUENCE: 74
gaaccaggcg gaacctgcag agatccaact cagcgcacgc g          41

<210> SEQ ID NO 75
<211> LENGTH: 57
<212> TYPE: DNA
<213> ORGANISM: Artificial
<220> FEATURE:
<223> OTHER INFORMATION: Synthetic DNA

<400> SEQUENCE: 75
tcgaatctag aaataatttt gtttaacttt aagaaggaga tatacatatg acgtcac       57

<210> SEQ ID NO 76
```

```
<211> LENGTH: 29
<212> TYPE: DNA
<213> ORGANISM: Artificial
<220> FEATURE:
<223> OTHER INFORMATION: Synthetic DNA

<400> SEQUENCE: 76
ggaacctgca gagatccaac ctagtcgtt                                  29

<210> SEQ ID NO 77
<211> LENGTH: 64
<212> TYPE: DNA
<213> ORGANISM: Artificial
<220> FEATURE:
<223> OTHER INFORMATION: Synthetic DNA

<400> SEQUENCE: 77
ccggttcgaa tctagaaata attttgttta actttaagaa ggagatatac atatgagcaa   60
taat                                                              64

<210> SEQ ID NO 78
<211> LENGTH: 41
<212> TYPE: DNA
<213> ORGANISM: Artificial
<220> FEATURE:
<223> OTHER INFORMATION: Synthetic DNA

<400> SEQUENCE: 78
gaaccaggcg gaacctgcag agatccaacc tatttgatca a                     41

<210> SEQ ID NO 79
<211> LENGTH: 64
<212> TYPE: DNA
<213> ORGANISM: Artificial
<220> FEATURE:
<223> OTHER INFORMATION: Synthetic DNA

<400> SEQUENCE: 79
ccggttcgaa tctagaaata attttgttta actttaagaa ggagatatac atatgagtaa   60
taca                                                              64

<210> SEQ ID NO 80
<211> LENGTH: 41
<212> TYPE: DNA
<213> ORGANISM: Artificial
<220> FEATURE:
<223> OTHER INFORMATION: Synthetic DNA

<400> SEQUENCE: 80
gaaccaggcg gaacctgcag agatccaact tacagttgat c                     41

<210> SEQ ID NO 81
<211> LENGTH: 64
<212> TYPE: DNA
<213> ORGANISM: Artificial
<220> FEATURE:
<223> OTHER INFORMATION: Synthetic DNA

<400> SEQUENCE: 81
ccggttcgaa tctagaaata attttgttta actttaagaa ggagatatac atatggaatc   60
gaca                                                              64

<210> SEQ ID NO 82
<211> LENGTH: 41
```

<212> TYPE: DNA
<213> ORGANISM: Artificial
<220> FEATURE:
<223> OTHER INFORMATION: Synthetic DNA

<400> SEQUENCE: 82
gaaccaggcg gaacctgcag agatccaact cactgtcgtt c        41

<210> SEQ ID NO 83
<211> LENGTH: 65
<212> TYPE: DNA
<213> ORGANISM: Artificial
<220> FEATURE:
<223> OTHER INFORMATION: Synthetic DNA

<400> SEQUENCE: 83
ccggttcgaa tctagaaata attttgttta actttaagaa ggagatatac atatgtggat    60
ggcta                                                               65

<210> SEQ ID NO 84
<211> LENGTH: 41
<212> TYPE: DNA
<213> ORGANISM: Artificial
<220> FEATURE:
<223> OTHER INFORMATION: Synthetic DNA

<400> SEQUENCE: 84
gaaccaggcg gaacctgcag agatccaacc tatgctgagc g        41

<210> SEQ ID NO 85
<211> LENGTH: 64
<212> TYPE: DNA
<213> ORGANISM: Artificial
<220> FEATURE:
<223> OTHER INFORMATION: Synthetic DNA

<400> SEQUENCE: 85
ccggttcgaa tctagaaata attttgttta actttaagaa ggagatatac atatgaattg    60
tttc                                                                64

<210> SEQ ID NO 86
<211> LENGTH: 41
<212> TYPE: DNA
<213> ORGANISM: Artificial
<220> FEATURE:
<223> OTHER INFORMATION: Synthetic DNA

<400> SEQUENCE: 86
gaaccaggcg gaacctgcag agatccaact taattagaac g        41

<210> SEQ ID NO 87
<211> LENGTH: 64
<212> TYPE: DNA
<213> ORGANISM: Artificial
<220> FEATURE:
<223> OTHER INFORMATION: Synthetic DNA

<400> SEQUENCE: 87
ccggttcgaa tctagaaata attttgttta actttaagaa ggagatatac atatgctctc    60
caat                                                                64

<210> SEQ ID NO 88
<211> LENGTH: 41
<212> TYPE: DNA

```
<213> ORGANISM: Artificial
<220> FEATURE:
<223> OTHER INFORMATION: Synthetic DNA

<400> SEQUENCE: 88
gaaccaggcg gaacctgcag agatccaact taatctgaac g                 41

<210> SEQ ID NO 89
<211> LENGTH: 65
<212> TYPE: DNA
<213> ORGANISM: Artificial
<220> FEATURE:
<223> OTHER INFORMATION: Synthetic DNA

<400> SEQUENCE: 89
ccggttcgaa tctagaaata attttgttta actttaagaa ggagatatac atatggcgga   60
ggcgg                                                              65

<210> SEQ ID NO 90
<211> LENGTH: 41
<212> TYPE: DNA
<213> ORGANISM: Artificial
<220> FEATURE:
<223> OTHER INFORMATION: Synthetic DNA

<400> SEQUENCE: 90
gaaccaggcg gaacctgcag agatccaacc taagtgcctg c                 41

<210> SEQ ID NO 91
<211> LENGTH: 64
<212> TYPE: DNA
<213> ORGANISM: Artificial
<220> FEATURE:
<223> OTHER INFORMATION: Synthetic DNA

<400> SEQUENCE: 91
ccggttcgaa tctagaaata attttgttta actttaagaa ggagatatac atttgatgga   60
actg                                                              64

<210> SEQ ID NO 92
<211> LENGTH: 41
<212> TYPE: DNA
<213> ORGANISM: Artificial
<220> FEATURE:
<223> OTHER INFORMATION: Synthetic DNA

<400> SEQUENCE: 92
gaaccaggcg gaacctgcag agatccaact catcggcgcg c                 41

<210> SEQ ID NO 93
<211> LENGTH: 64
<212> TYPE: DNA
<213> ORGANISM: Artificial
<220> FEATURE:
<223> OTHER INFORMATION: Synthetic DNA

<400> SEQUENCE: 93
ccggttcgaa tctagaaata attttgttta actttaagaa ggagatatac atatggcgac   60
cggc                                                              64

<210> SEQ ID NO 94
<211> LENGTH: 41
<212> TYPE: DNA
<213> ORGANISM: Artificial
```

```
<220> FEATURE:
<223> OTHER INFORMATION: Synthetic DNA

<400> SEQUENCE: 94
gaaccaggcg gaacctgcag agatccaact catgccttgg c                    41
```

RECOMBINANT MICROORGANISM AND METHOD FOR PRODUCING ALIPHATIC POLYESTER USING THE SAME

CROSS REFERENCE TO RELATED APPLICATIONS

This application is a National Stage of International Application No. PCT/JP2011/057077 filed Mar. 24, 2011, claiming priority based on Japanese Patent Application No. 2010-069688 filed Mar. 25, 2010, the contents of all of which are incorporated herein by reference in their entirety.

TECHNICAL FIELD

The present invention relates to a recombinant microorganism to which desired functions are imparted by introducing a predetermined gene into a host microorganism and a method for producing aliphatic polyester using the same.

BACKGROUND ART

Aliphatic polyester is attracting attention as biodegradable plastic that can be easily degraded in nature or "green" plastic that can be synthesized from recyclable carbon resources such as sugar or vegetable oil. Currently, as aliphatic polyester, polyester having a lactic acid backbone, such as polylactic acid, is practically used.

As a technology for producing aliphatic polyester such as polylactic acid using a recombinant microorganism, for example, the technology disclosed in Patent Document 1 (WO 2006/126796) is known. Patent Document 1 discloses recombinant *Escherichia coli* prepared by introducing a gene encoding an enzyme that converts lactic acid to lactic-acid CoA and a gene encoding an enzyme that synthesizes polyhydroxyalkanoate using lactic-acid CoA as a substrate into host *Escherichia coli*. According to the technology disclosed in Patent Document 1, a *Clostridium propionicum*-derived pct gene is used as a gene encoding an enzyme that converts lactic acid to lactic-acid CoA. Furthermore, according to this technology, a *Pseudomonas* sp. 61-3 strain-derived phaC2 gene is used as a gene encoding an enzyme that synthesizes polyhydroxyalkanoate using lactic-acid CoA as a substrate.

However, Patent Document 1 has problems in that the productivity of aliphatic polyester such as polylactic acid cannot be said to be sufficient, and various examinations for improvement of the productivity are insufficient. For example, Patent Document 2 (WO 2008/062999) discloses an attempt to enhance the capacity of synthesizing a lactic acid homopolymer or a polylactic acid copolymer using lactic-acid CoA as a substrate through introduction of a specific mutation into a phaC1 gene from the *Pseudomonas* sp. 6-19 strain.

The above technology for producing aliphatic polyester such as polylactic acid using a recombinant microorganism involves accumulating aliphatic polyester within the microorganism. Hence, target aliphatic polyester is recovered by disrupting the microorganism.

PRIOR ART DOCUMENTS

Patent Documents

Patent Document 1 WO 2006/126796
Patent Document 2 WO 2008/062999

SUMMARY OF THE INVENTION

Problem to be Solved by the Invention

However, conventionally, such technology for producing aliphatic polyester such as polylactic acid using a recombinant microorganism has been problematic in that productivity is low since aliphatic polyester is accumulated within the microorganism, and complicated steps are required in order to disrupt the microorganism and then recovering aliphatic polyester. Hence, an object of the present invention is to provide a recombinant microorganism having good aliphatic polyester productivity and to provide a method for producing aliphatic polyester using the recombinant microorganism.

Means for Solving the Problem

As a result of intensive studies to achieve the above object, the present inventors have discovered that, in a recombinant microorganism prepared by introducing a propionyl CoA transferase gene and a polyhydroxyalkanoate synthase gene from a predetermined microorganism, aliphatic polyester such as polylactic acid is produced extracellularly, and thus they have completed the present invention.

Specifically, the present invention encompasses the following (1) to (11).
(1) A method for producing aliphatic polyester, comprising culturing a recombinant microorganism prepared by introducing a gene encoding a protein that has activity of converting lactic acid to lactic-acid CoA and a gene encoding a protein that has activity of synthesizing polyhydroxyalkanoate using hydroxyacyl CoA as a substrate into a host microorganism, and then recovering aliphatic polyester from medium.
(2) The method for producing aliphatic polyester according to (1), wherein the aliphatic polyester comprises oligomers that are mainly a dimer, a trimer, a tetramer, and a pentamer.
(3) The method for producing aliphatic polyester according to (1), wherein the aliphatic polyester has the lactic acid backbone.
(4) The method for producing aliphatic polyester according to (1), wherein the aliphatic polyester is polylactic acid.
(5) The method for producing aliphatic polyester according to (1), wherein the medium is a minimal medium.
(6) The method for producing aliphatic polyester according to (1), wherein the recombinant microorganism is cultured for 48 hours or more and then the aliphatic polyester is recovered.
(7) The method for producing aliphatic polyester according to (1), wherein the gene encoding a protein that has activity of synthesizing polyhydroxyalkanoate using the hydroxyacyl CoA as a substrate is at least one gene selected from an *Alcanivorax borkumensis*-derived gene, a *Hyphomonas neptunium*-derived gene, a *Rhodobacter sphaeroides*-derived gene, a *Rhizobium etli*-derived gene, a *Pseudomonas* sp.-derived gene, and a *Haloarcula marismortui*-derived gene.
(8) The method for producing aliphatic polyester according to (1), wherein the gene encoding the protein that has activity of synthesizing polyhydroxyalkanoate using hydroxyacyl CoA as a substrate is the following gene (a), (b), or (c):
(a) a gene encoding a protein that comprises the amino acid sequence shown in SEQ ID NO: 6, 8, 10, 12, 14, 16, or 18;
(b) a gene encoding a protein that comprises an amino acid sequence having a substitution, a deletion, or an addition of 1 or a plurality of amino acids with respect to the amino acid sequence shown in SEQ ID NO: 6, 8, 10, 12, 14, 16, or 18, and has the above activity; or (c) a gene hybridizing under stringent conditions to a polynucleotide that has a nucleotide sequence complementary to the nucleotide sequence shown in SEQ ID NO: 5, 7, 9, 11, 13, 15, or 17, and encoding a protein that has the above activity;
(9) A recombinant microorganism, which is prepared by introducing:
a gene encoding a protein having activity of converting lactic acid to lactic-acid CoA; and
one or more genes encoding a protein(s) having activity of synthesizing polyhydroxyalkanoate using hydroxyacyl CoA as a substrate, which is selected from an *Alcanivorax borkumensis*-derived gene, a *Hyphomonas neptunium*-derived gene, a *Rhodobacter sphaeroides*-derived gene, a *Rhizobium etli*-derived gene, a *Pseudomonas* sp.-derived gene, and a *Haloarcula marismortui*-derived gene that are a gene encoding a protein and, into a host microorganism.
(10) The recombinant microorganism according to (9), wherein the gene that encodes a protein having activity of synthesizing polyhydroxyalkanoate using hydroxyacyl CoA as a substrate is the following gene (a), (b), or (c):
(a) a gene encoding a protein that comprises the amino acid sequence shown in SEQ ID NO: 6, 8, 10, 12, 14, 16, or 18;
(b) a gene encoding a protein that comprises an amino acid sequence having a substitution, a deletion, or an addition of 1 or a plurality of amino acids with respect to the amino acid sequence shown in SEQ ID NO: 6, 8, 10, 12, 14, 16, or 18, and has the above activity; or
(c) a gene hybridizing under stringent conditions to a polynucleotide that has a nucleotide sequence complementary to the nucleotide sequence shown in SEQ ID NO: 5, 7, 9, 11, 13, 15, or 17 and encoding a protein having the above activity.
(11) The recombinant microorganism according to (9), wherein the host microorganism is *Escherichia coli*.

This description includes part or all of the contents as disclosed in the description and/or drawings of Japanese Patent Application No. 2010-069688, which is a priority document of the present application.

Effects of the Invention

According to the present invention, a recombinant microorganism capable of producing aliphatic polyester extracellularly can be provided. Specifically, the recombinant microorganism according to the present invention has higher aliphatic polyester productivity than conventional recombinant microorganisms. Also, through the use of the recombinant microorganism according to the present invention, a method for producing aliphatic polyester with high productivity can be provided.

EMBODIMENTS FOR CARRYING OUT THE INVENTION

Figure 1:
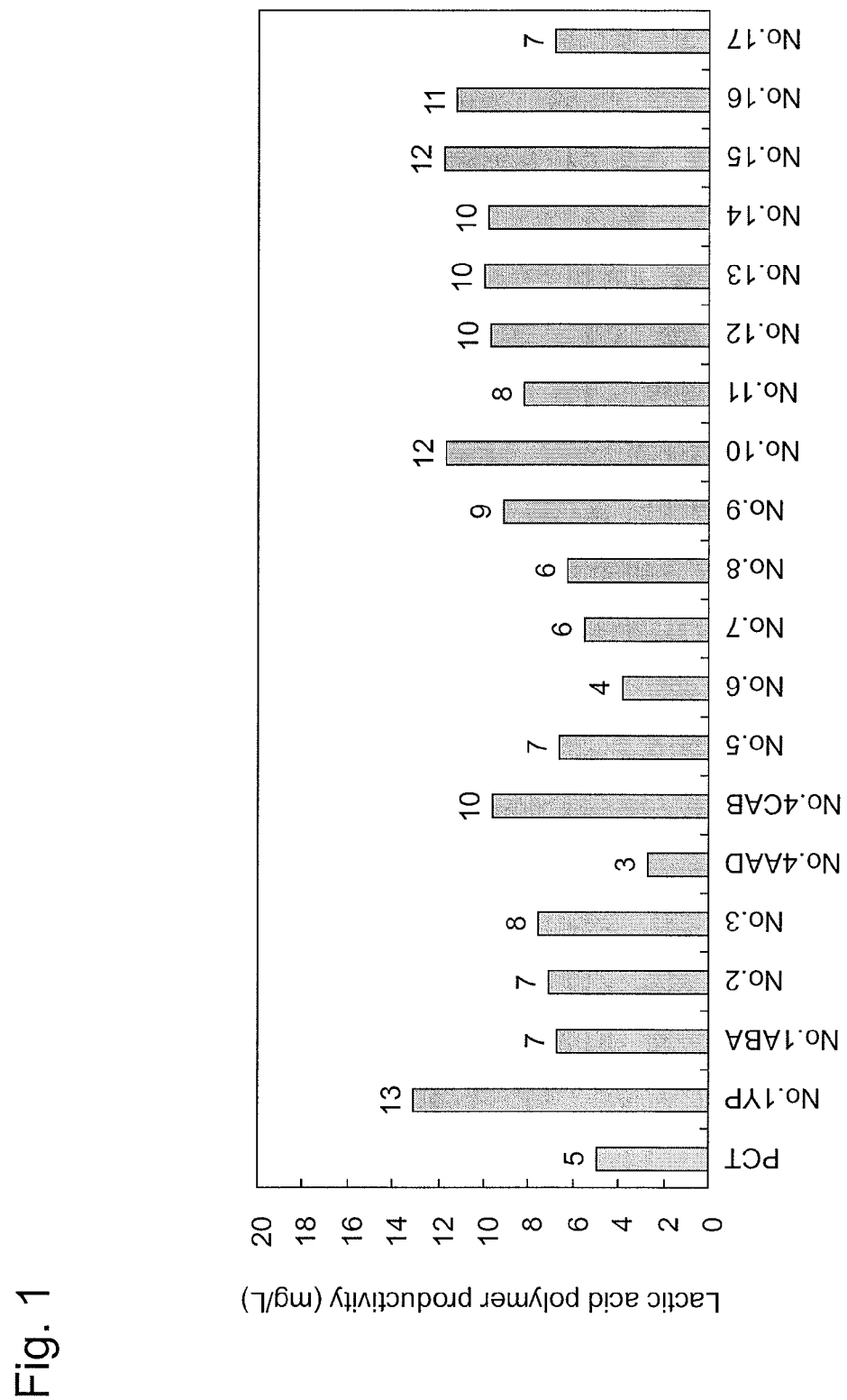
FIG. 1 is a characteristic diagram showing the results of measuring by GC-MS the lactic acid polymer production in each type of recombinant *Escherichia coli*.
Figure 2:
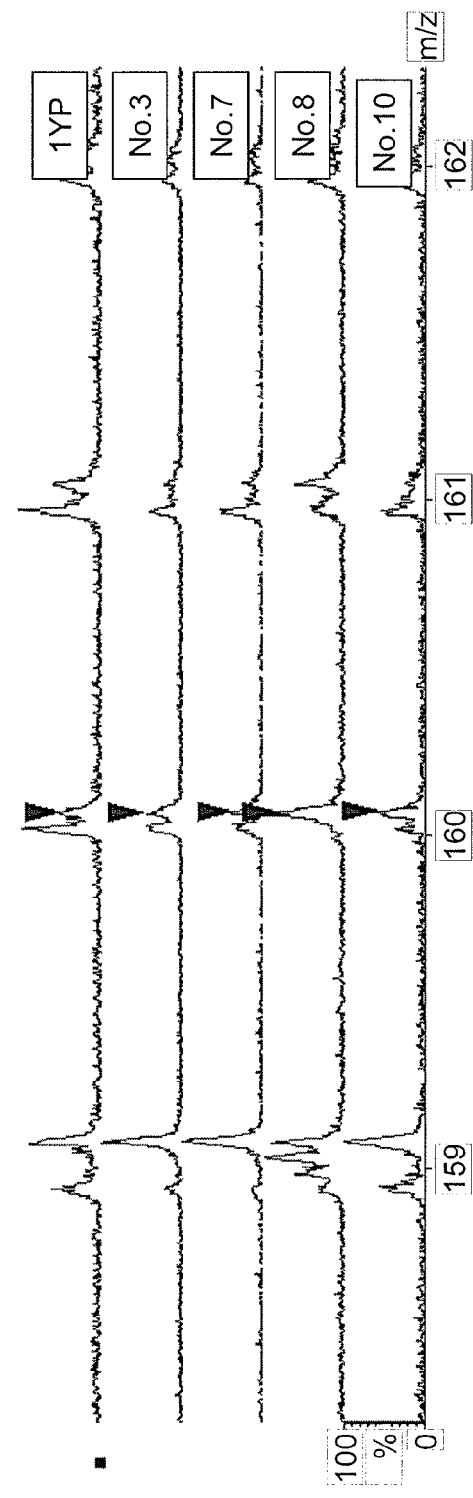
FIG. 2 is a characteristic diagram showing the results of measuring a lactic acid dimer in medium for recombinant *Escherichia coli* in which a *Hyphomonas neptunium*-derived PHA synthase gene (No. 8), a *Rhodobacter sphaeroides*-derived PHA synthase gene (No. 1), a *Rhizobium etli*-derived PHA synthase gene (No. 3), a *Pseudomonas* sp.-derived PHA synthase gene (No. 7), or a *Haloarcula marismortui*-derived PHA synthase gene (No. 10) was introduced.
Figure 3:
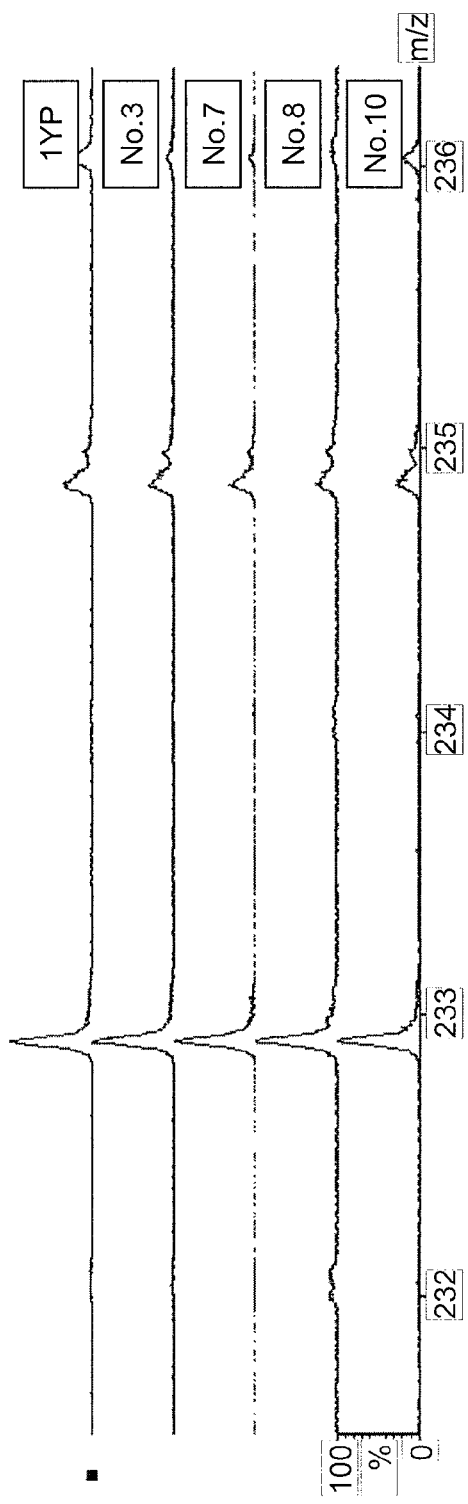
FIG. 3 is a characteristic diagram showing the results of measuring a lactic acid trimer in medium for recombinant *Escherichia coli* in which the *Hyphomonas neptunium*-derived PHA synthase gene (No. 8), the *Rhodobacter sphaeroides*-derived PHA synthase gene (No. 1), the *Rhizobium etli*-derived PHA synthase gene (No. 3), the *Pseudomonas* sp.-derived PHA synthase gene (No. 7), or the *Haloarcula marismortui*-derived PHA synthase gene (No. 10) was introduced.
Figure 4:
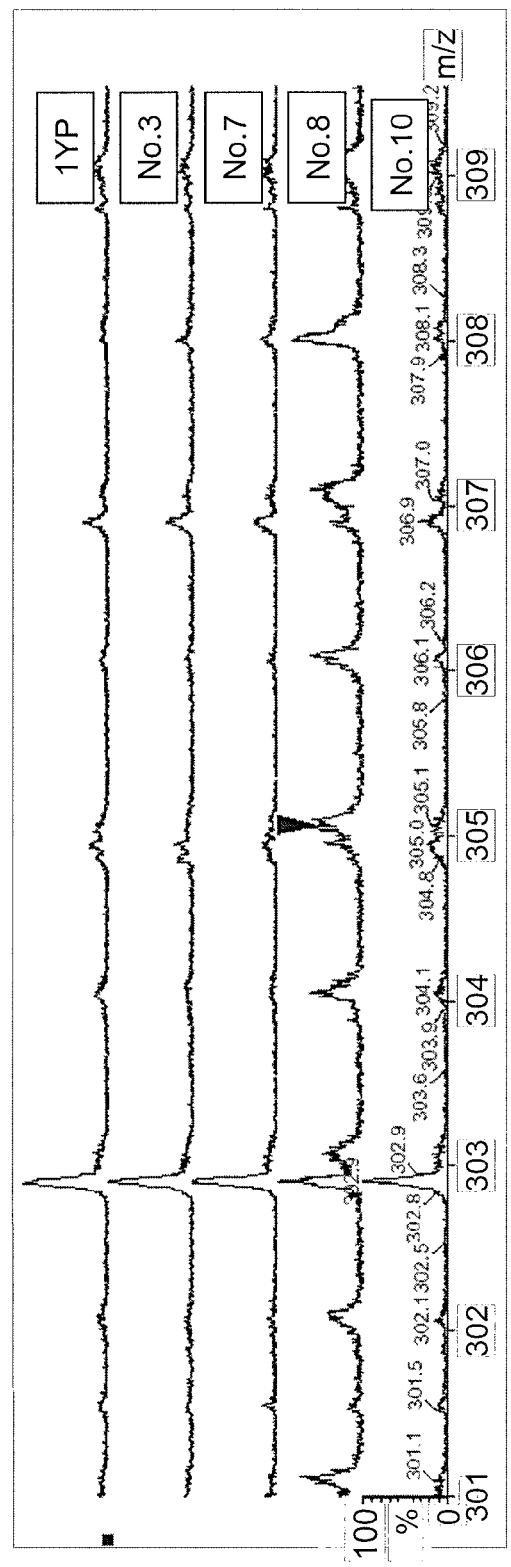
FIG. 4 is a characteristic diagram showing the results of measuring a lactic acid tetramer in medium for recombinant *Escherichia coli* in which the *Hyphomonas neptunium*-derived PHA synthase gene (No. 8), the *Rhodobacter sphaeroides*-derived PHA synthase gene (No. 1), the *Rhizobium etli*-derived PHA synthase gene (No. 3), the *Pseudomonas* sp.-derived PHA synthase gene (No. 7), or the *Haloarcula marismortui*-derived PHA synthase gene (No. 10) was introduced.
Figure 5:
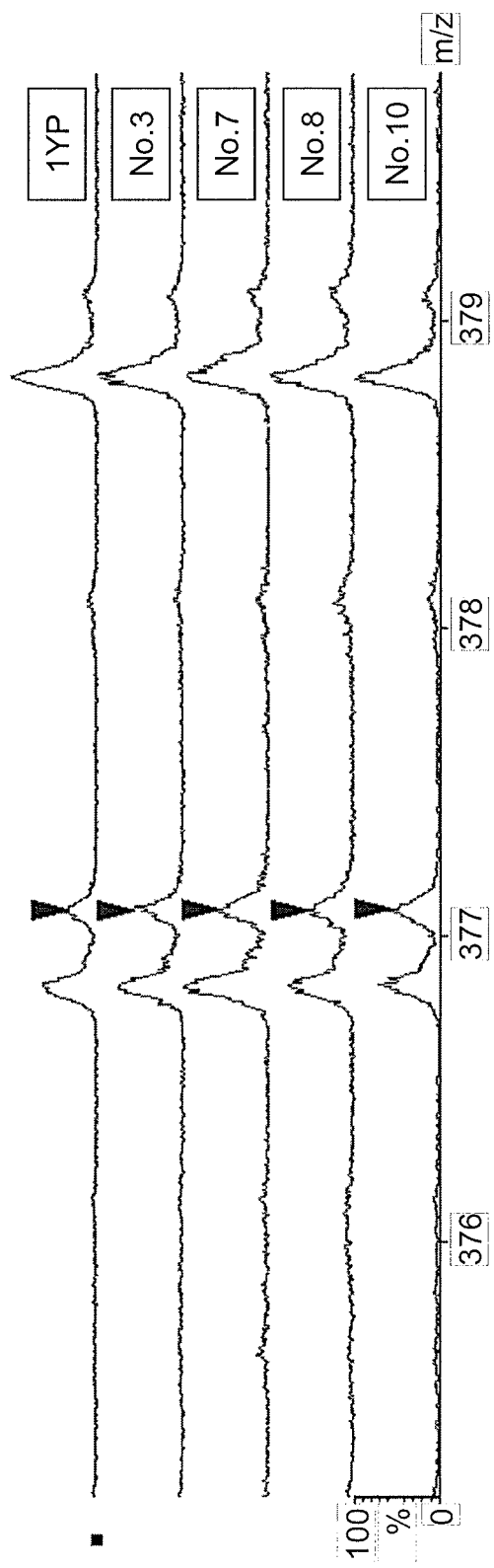
FIG. 5 is a characteristic diagram showing the results of measuring a lactic acid pentamer in medium for recombinant *Escherichia coli* in which the *Hyphomonas neptunium*-derived PHA synthase gene (No. 8), the *Rhodobacter sphaeroides*-derived PHA synthase gene (No. 1), the *Rhizobium etli*-derived PHA synthase gene (No. 3), the *Pseudomonas* sp.-derived PHA synthase gene (No. 7), or the *Haloarcula marismortui*-derived PHA synthase gene (No. 10) was introduced.
Figure 6:
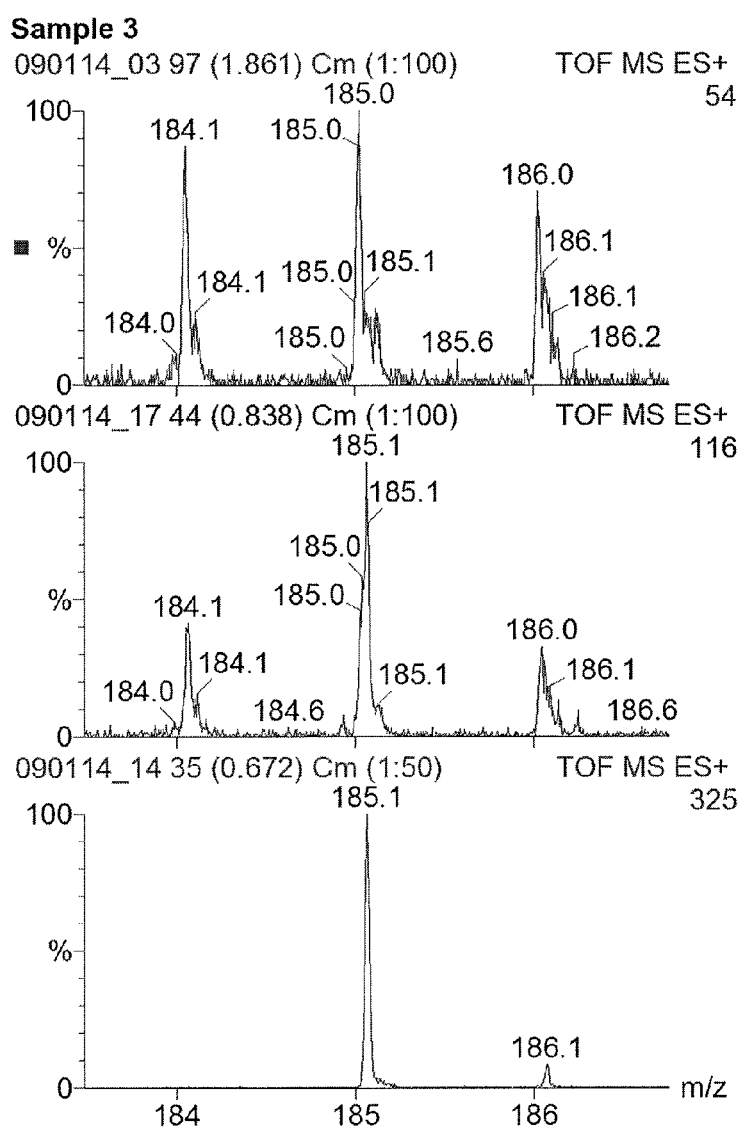
FIG. 6 is a characteristic diagram showing the results of measuring a lactic acid dimer in medium for recombinant *Escherichia coli* in which an *Alcanivorax borkumensis*-derived PHA synthase gene (No. 12) was introduced.
Figure 7:
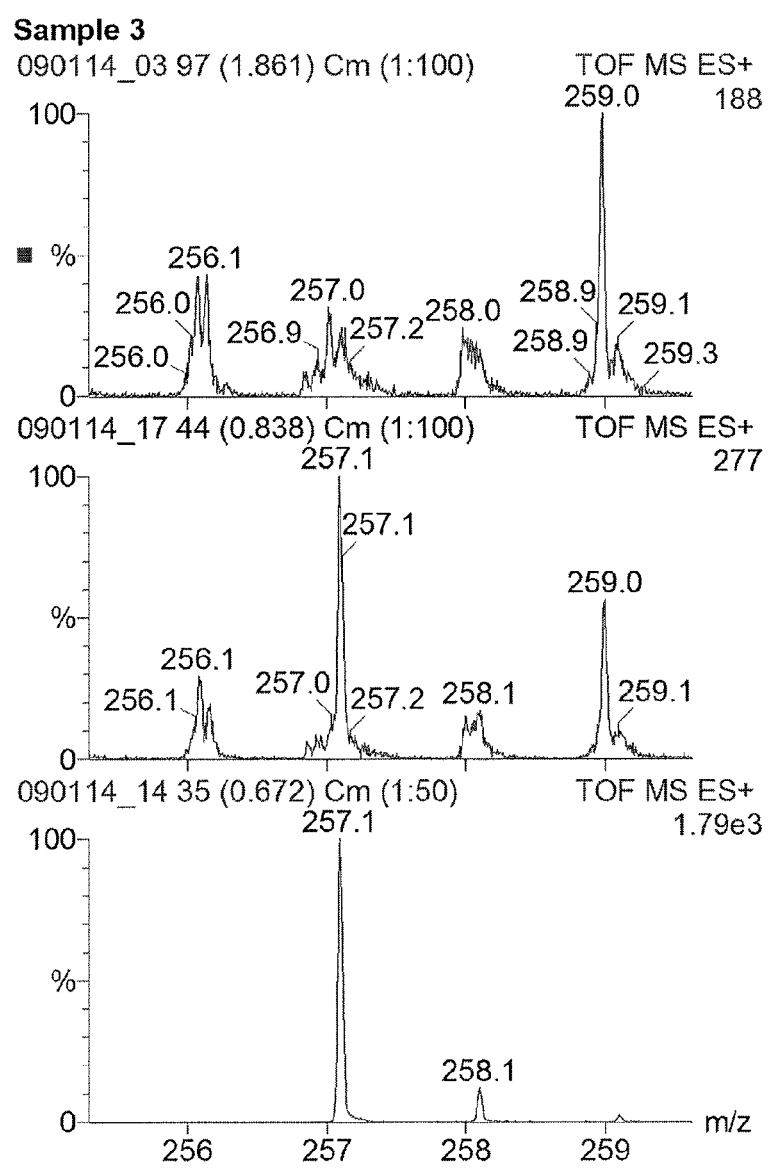
FIG. 7 is a characteristic diagram showing the results of measuring a lactic acid trimer in medium for recombinant *Escherichia coli* in which the *Alcanivorax borkumensis*-derived PHA synthase gene (No. 12) was introduced.
Figure 8:
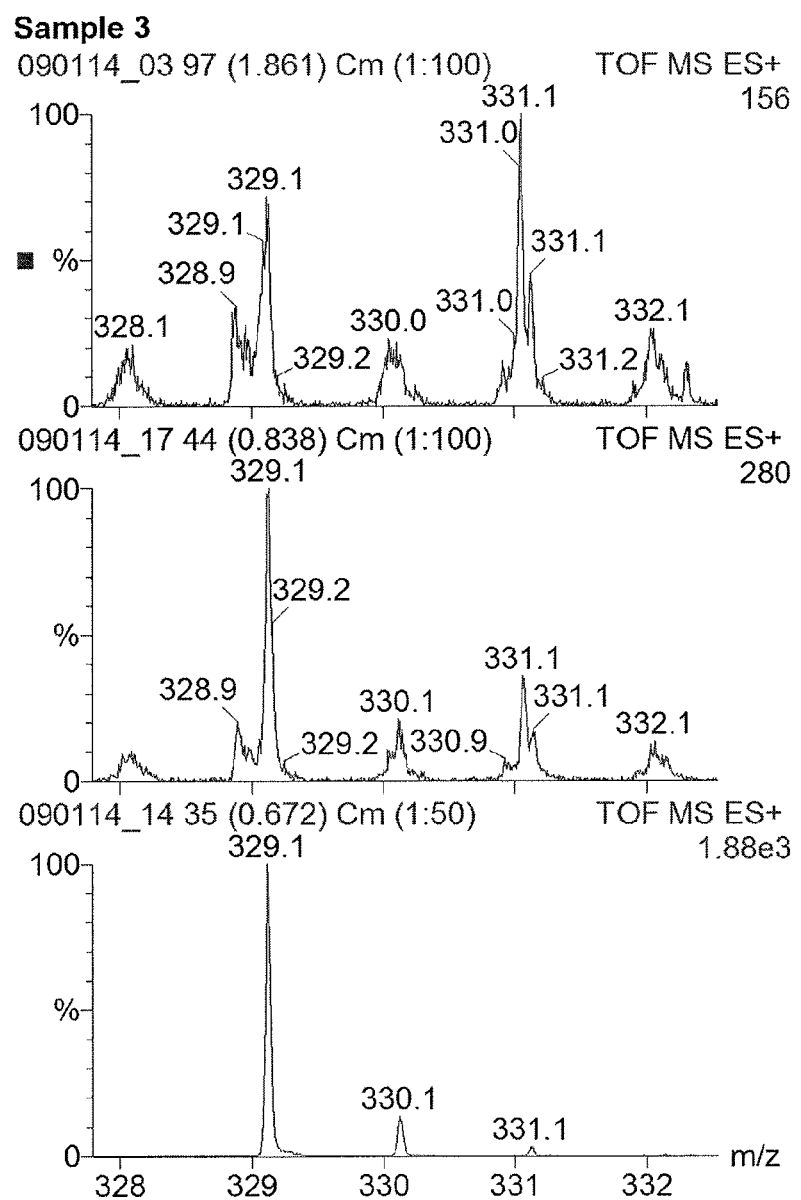
FIG. 8 is a characteristic diagram showing the results of measuring a lactic acid tetramer in medium for recombinant *Escherichia coli* in which the *Alcanivorax borkumensis*-derived PHA synthase gene (No. 12) was introduced.
Figure 9:
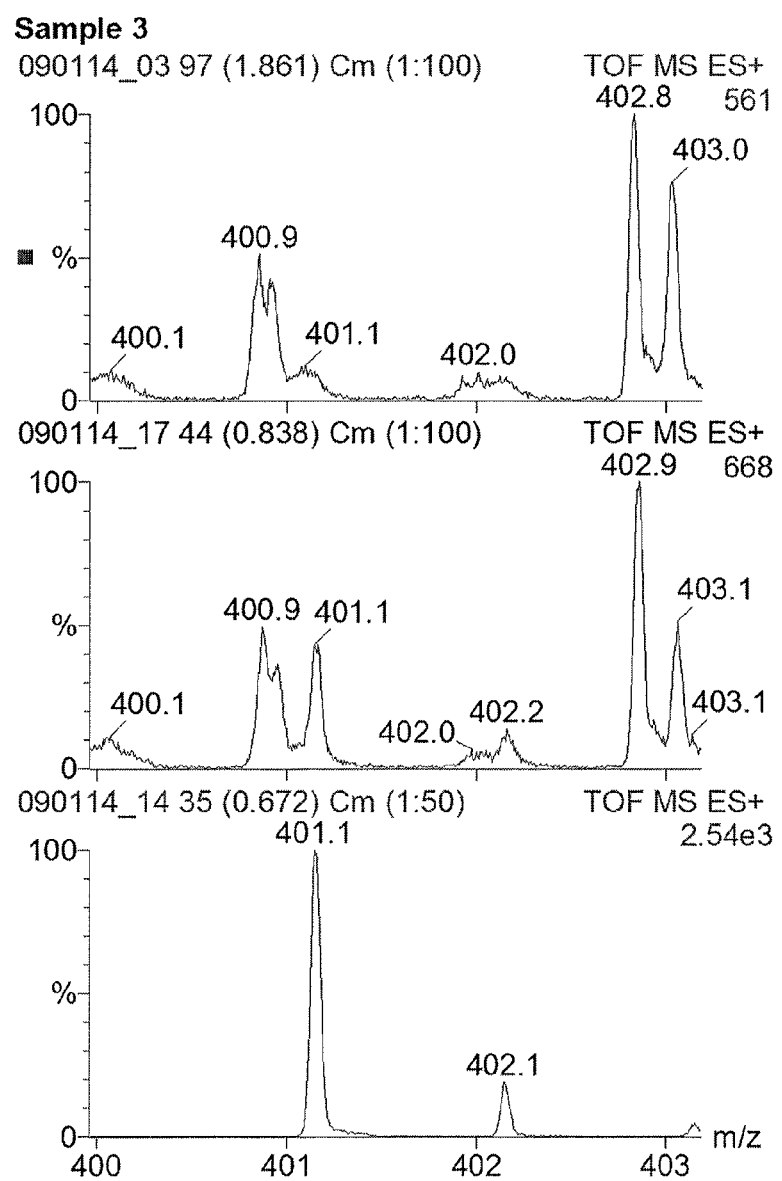
FIG. 9 is a characteristic diagram showing the results of measuring a lactic acid pentamer in medium for recombinant *Escherichia coli* in which the *Alcanivorax borkumensis*-derived PHA synthase gene (No. 12) was introduced.
Figure 10:
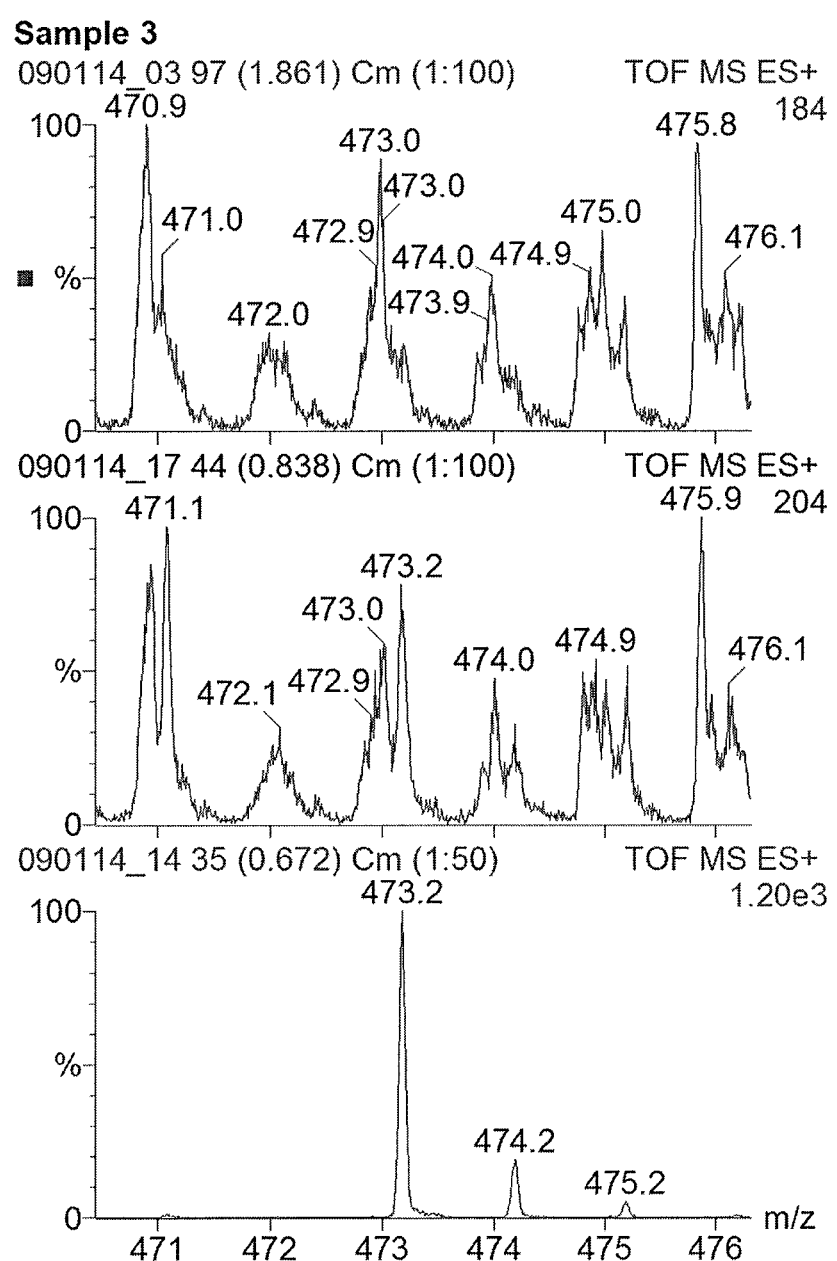
FIG. 10 is a characteristic diagram showing the results of measuring a lactic acid hexamer in medium for recombinant *Escherichia coli* in which the *Alcanivorax borkumensis*-derived PHA synthase gene (No. 12) was introduced.
Figure 11:
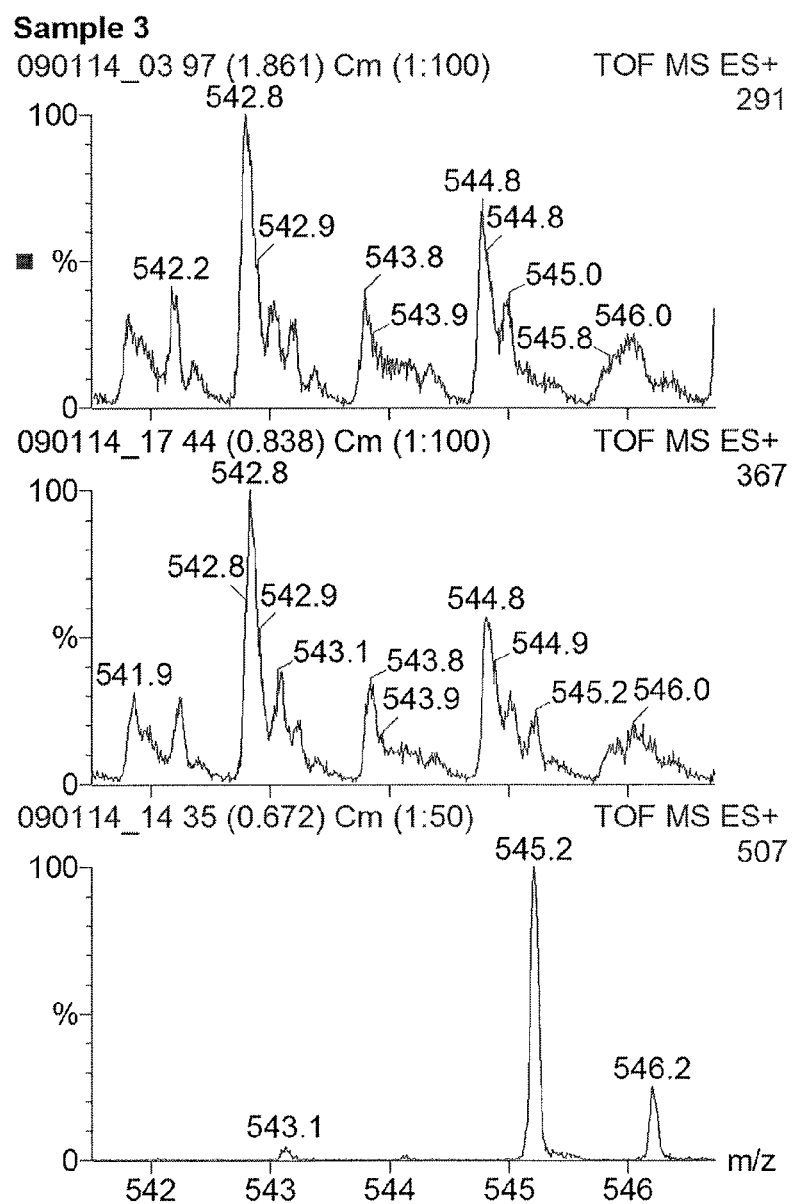
FIG. 11 is a characteristic diagram showing the results of measuring a lactic acid heptamer in medium for recombinant *Escherichia coli* in which the *Alcanivorax borkumensis*-derived PHA synthase gene (No. 12) was introduced.

Hereinafter, the recombinant microorganism and the method for producing aliphatic polyester using the same according to the present invention are as described in detail.

The recombinant microorganism according to the present invention is prepared by introducing a propionyl CoA transferase gene (pct gene) and a predetermined polyhydroxyalkanoate synthase gene into a host microorganism, and it produces aliphatic polyester outside the host microorganism. In addition, the term "aliphatic polyester" as used herein refers to not only polymers (macromolecular substances) each having a molecular weight of several thousands to several tens of thousands, but also oligomers each having 2 to 5 monomeric units (that is, dimer to pentamer).

Propionyl CoA Transferase Gene

In the present invention, a propionyl CoA transferase gene (hereinafter, referred to as "pct gene") is not particularly limited and any gene can be used herein, as long as it encodes a protein having activity of converting lactic acid to lactic-acid CoA. Specifically, as a pct gene, any gene that encodes a protein having propionyl CoA transferase activity can be used. The term "propionyl CoA transferase activity" refers to activity of catalyzing a reaction by which CoA is transferred to propionic acid. Specifically, activity of catalyzing a reaction by which CoA is transferred from an appropriate CoA substrate to propionic acid is referred to as propionyl CoA transferase activity. The propionyl CoA transferase can transfer CoA not only to propionic acid, but also to lactic acid from a CoA substrate.

Table 1 shows representative examples of origins (names of microorganisms) of pct genes reported to date and document information disclosing the information of nucleotide sequences encoded by the genes.

TABLE 1

| Names of microorganisms | Document information |
| --- | --- |
| Clostridium propionicum | Eur. J. Biochem., 2002, Vol. 269, pp. 372-380 |
| Megasphaera elsdenii | United States patent 7,186,541 |
| Staphylococcus aureus | Eur. J. Biochem., 2002, Vol. 269, pp. 372-380 |
| Escherichia coll | Eur. J. Biochem., 2002, Vol. 269, pp. 372-380 |

In the present invention, any pct gene that has been reported to date can be used in addition to those listed in Table 1 above. Also, any protein comprising an amino acid sequence that has a deletion, a substitution, or an addition of 1 or several amino acids with respect to a known amino acid sequence of a pct protein can be used, as long as it has propionyl CoA transferase activity. In addition, the term "several" used in relation to the amino acid sequence of a pct protein refers to 1 to 50, preferably 1 to 25, and more preferably 10 or less amino acids. Catalytic activity exhibited by propionyl CoA transferase can be measured according to a method described by A. E. Hofineister et al., (Eur. J. Biochem., Vol. 206, pp. 547-552), for example.

Examples of the pct gene include a *Megasphaera elsdenii*-derived gene and a *Staphylococcus aureus*-derived gene. The nucleotide sequence of the coding region in the *Megasphaera elsdenii*-derived pct gene is shown in SEQ ID NO: 1, and the amino acid sequence of the protein encoded by the pct gene is shown in SEQ ID NO: 2. Also, the nucleotide sequence of the coding region in the *Staphylococcus aureus*-derived pct gene is shown in SEQ ID NO: 3, and the amino acid sequence of the protein encoded by the pct gene is shown in SEQ ID NO: 4. The protein comprising the amino acid sequence shown in SEQ ID NO: 2 or 4 has propionyl CoA transferase activity, and particularly activity of synthesizing lactic-acid CoA using lactic acid as a substrate.

Also, in the present invention, examples of the pct gene is not limited to the gene having the nucleotide sequence encoding the amino acid sequence shown in SEQ ID NO: 2 or 4, and may be a pct gene encoding a protein that comprises an amino acid sequence having a deletion, a substitution, or an addition of 1 or a plurality of amino acid sequences with respect to the relevant amino acid sequence, and has activity of converting lactic acid to lactic-acid CoA. Here, the term "a plurality of amino acids" refers to, for example, 1 to 20, preferably 1 to 10, more preferably 1 to 7, further preferably 1 to 5, and particularly preferably 1 to 3 amino acids.

Furthermore, in the present invention, the pct gene may be a pct gene encoding a protein that comprises an amino acid sequence having, for example, 70% or more, preferably 80% or more, more preferably 90% or more, and most preferably 95% or more sequence similarity with respect to the amino acid sequence shown in SEQ ID NO: 2 or 4, and has activity of converting lactic acid to lactic-acid CoA. Here, the value of sequence similarity refers to a value that is found using a computer program for blast algorithm implementation, database storing gene sequence information, and default setting.

Furthermore, in the present invention, the pct gene may also be a pct gene that comprises a polynucleotide hybridizing under stringent conditions to at least a portion of a gene having the nucleotide sequence shown in SEQ ID NO: 1 or 3, and, encodes a protein having activity of converting lactic acid to lactic-acid CoA. Here the term "stringent conditions" refers to conditions wherein namely a specific hybrid is formed, but no non-specific hybrid is formed. Examples thereof include hybridization at 45° C. with 6×SSC (sodium chloride/sodium citrate), followed by washing at 50° C. to 65° C. with 0.2 to 1×SSC and 0.1% SDS. Alternatively, examples of such conditions further include conditions of hybridization at 65° C. to 70° C. with 1×SSC, followed by washing at 65° C. to 70° C. with 0.3×SSC. Hybridization can be performed by a conventionally known method such as a method described in J. Sambrook et al. Molecular Cloning, A Laboratory Manual, 2nd Ed., Cold Spring Harbor Laboratory (1989).

In addition, deletion, substitution, or addition of an amino acid(s) can be performed by modifying a nucleotide sequence encoding the above transcription factor by a technique known in the art. Mutation can be introduced into a nucleotide sequence by a known technique such as a Kunkel method or a Gapped duplex method or a method according thereto. For example, mutation is introduced using a mutagenesis kit (e.g., Mutant-K and Mutant-G (both are trade names, TAKARA Bio)) or the like using site-directed mutagenesis, or a LA PCR in vitro Mutagenesis Series Kit (trade name, TAKARA Bio). Furthermore, a mutagenesis method may be a method using a chemical agent for mutation represented by EMS (ethyl methanesulfonic acid), 5-bromouracil, 2-aminopurine, hydroxylamine, N-methyl-N'-nitro-N nitrosoguanidine, other carcinogenic compounds or the like, or a method using radiation processing as represented by X-ray processing, alpha ray processing, beta ray processing, gamma ray processing, or ion beam processing, or ultraviolet [UV] treatment.

Polyhydroxyalkanoate Synthase Gene

In the present invention, as a polyhydroxyalkanoate synthase gene (also referred to as a PHA synthase gene), at least one gene selected from an *Alcanivorax borkumensis*-derived gene, a *Hyphomonas neptunium*-derived gene, a *Rhodobacter sphaeroides*-derived gene, a *Rhizobium etli*-derived gene, a *Pseudomonas* sp.-derived gene, and a *Haloarcula marismortui*-derived gene is used. In particular, as a PHA synthase gene, an *Alcanivorax borkumensis*-derived gene and/or a *Hyphomonas neptunium*-derived gene is preferably used. In addition, the term "PHA synthase gene" refers to a gene encoding a protein that has activity of synthesizing polyhydroxyalkanoate using hydroxyacyl CoA as a substrate.

As the *Alcanivorax borkumensis*-derived gene, the PHA synthase gene derived from the SK2 strain preserved in the ATCC under Accession Number: 700651 can be preferably used. Also, as the *Hyphomonas neptuniums*-derived gene, a PHA synthase gene derived from the strain preserved in the NBRC under Accession Number: 14232 is preferably used.

As the *Rhodobacter sphaeroides*-derived gene, a PHA synthase gene derived from the strain preserved in the ATCC (American Type Culture Collection) under Accession Number: BAA-808D is preferably used. As the *Rhizobium etli*-derived gene, a PHA synthase gene derived from the CFN strain preserved in the NBRC (NITE Biological Resource Center) under Accession Number: 15573 is preferably used. As the *Pseudomonas* sp.-derived gene, a PHA synthase gene derived from the 61-3 strain preserved in the JCM (Japan Collection of Microorganisms) under Accession Number: 10015 is preferably used. As the *Haloarcula marismortui*-derived gene, a PHA synthase gene from the strain preserved in the JCM under Accession Number: 8966 is preferably used.

Specifically, the nucleotide sequence of the coding region in the *Alcanivorax borkumensis* (ATCC 700651)-derived PHA synthase gene is shown in SEQ ID NO: 5, and the amino acid sequence of the protein to be encoded by the gene is shown in SEQ ID NO: 6. The nucleotide sequence of the coding region in the *Hyphomonas neptunium* (NBRC 14232)-derived PHA synthase gene is shown in SEQ ID NO: 7, and the amino acid sequence of the protein to be encoded by the gene is shown in SEQ ID NO: 8.

Also, examples of the *Rhodobacter sphaeroides* (BAA-808D)-derived gene include the PHA synthase gene specified by Accession Number: YP354337 and the PHA synthase gene specified by Accession Number: ABA79557. The nucleotide sequence of the coding region in the PHA synthase gene specified by Accession Number:YP354337 is shown in SEQ ID NO: 9, and the amino acid sequence of the protein to be encoded by the gene is shown in SEQ ID NO: 10. The nucleotide sequence of the coding region in the PHA synthase gene specified by Accession Number: ABA79557 is shown in SEQ ID NO: 11, and the amino acid sequence of the protein to be encoded by the gene is shown in SEQ ID NO: 12.

The nucleotide sequence of the coding region in the *Rhizobium etli* CFN strain-derived PHA synthase gene is shown in SEQ ID NO: 13, and the amino acid sequence of the protein to be encoded by the gene is shown in SEQ ID NO: 14. The nucleotide sequence of the coding region in the *Pseudomonas* sp. 61-3 strain-derived PHA synthase gene is shown in SEQ ID NO: 15, and the amino acid sequence of the protein to be encoded by the gene is shown in SEQ ID NO: 16. The nucleotide sequence of the coding region in the *Haloarcula marismortui* (JCM 8966)-derived PHA synthase gene is shown in SEQ ID NO: 17, and the amino acid sequence of the protein to be encoded by the gene is shown in SEQ ID NO: 18.

Furthermore, in the present invention, examples of the PHA synthase gene are not limited to those having the nucleotide sequences encoding the amino acid sequences specified by the above specific SEQ ID NOS. The PHA synthase gene may be a PHA synthase gene encoding a protein that comprises an amino acid sequence having a deletion, a substitution, or an addition of 1 or a plurality of amino acid sequences with respect to the relevant amino acid sequence, and, has activity of synthesizing polylactic acid using lactic-acid CoA as a substrate. Here, the term "a plurality of amino acids" refers to, for example, 1 to 20, preferably 1 to 10, more preferably 1 to 7, further preferably 1 to 5, and particularly preferably 1 to 3 amino acids.

Furthermore, in the present invention, the PHA synthase gene may be a PHA synthase gene encoding a protein that comprises an amino acid sequence having, for example, 70% or more, preferably 80% or more, more preferably 90% or more, and most preferably 95% or more sequence similarity with the amino acid sequence specified by the above specific SEQ ID NO, and has activity of synthesizing polylactic acid using lactic-acid CoA as a substrate. Here, the value for sequence similarity refers to a value that is found by a computer program for blast algorithm implementation using database storing gene sequence information and the default setting.

Furthermore, in the present invention, the PHA synthase gene may be a PHA synthase gene comprising a polynucleotide that hybridizes under stringent conditions to at least a portion of a gene having the nucleotide sequence specified by the above specific SEQ ID NO:, and, encoding a protein having activity of synthesizing polylactic acid using lactic-acid CoA as a substrate. In addition, the term "stringent conditions" is synonymous with the conditions as described in the section of "Propionyl CoA transferase gene."

Also, techniques described in the section of "Propionyl CoA transferase gene" can be applied for deletion, substitution, or addition of an amino acid(s).

In particular, the recombinant microorganism according to the present invention is prepared by introducing the above-described PHA synthase gene, so that it can produce an aliphatic polyester oligomer, and particularly, a lactic acid oligomer outside the microorganism. Here, an oligomer having the degree of polymerization that differs depending on the types of PHA synthase gene to be used herein can be produced. With the recombinant microorganism prepared by introducing the *Alcanivorax borkumensis*-derived PHA synthase gene, tetrameric and pentameric aliphatic polyester oligomers (e.g., lactic acid oligomers) can be produced. Also, with the recombinant microorganism prepared by introducing the *Hyphomonas neptunium*-derived PHA synthase gene, a tetrameric aliphatic polyester oligomer (e.g., a lactic acid oligomer) can be produced.

Host Microorganism

Examples of a host microorganism to be used in the present invention include bacteria of the genus *Pseudomonas* such as the *Pseudomonas* sp. 61-3 strain, bacteria of the genus *Ralstonia* such as *R. eutropha*, bacteria of the genus *Bacillus* such as *Bacillus subtilis*, bacteria of the genus *Escherichia* such as *Escherichia coli*, bacteria of the genus *Corynebacterium*, yeast of the genus *Saccharomyces* such as *Saccharomyces cerevisiae*, and yeast of the genus *Candida* such as *Candida maltosa*. As a host microorganism, *Escherichia coli* is particularly preferably used.

A vector for introducing the above gene into a host cell may be a vector that is autonomously replicable in the host, and is preferably in the form of plasmid DNA or phage DNA. Examples of such a vector to be introduced into *Escherichia coli* include plasmid DNA such as pBR322, pUC18, and pBluescript II and phage DNA such as EMBL3, M13, and λgtII. Examples of a vector to be introduced into yeast include YEp13 and YCp50.

Both or either one of the above genes can be inserted into a vector by a gene recombination technique known by persons skilled in the art. Also, upon recombination, the above gene is preferably ligated downstream of a promoter capable of regulating transcription. As a promoter, any promoter capable of regulating transcription of a gene in a host can also be used herein. For example, when *Escherichia coli* is used as a host, a trp promoter, a lac promoter, a PL promoter, a PR promoter, a T7 promoter, or the like is used. When yeast is used as a host, a gall promoter, a gal10 promoter, or the like can be used.

Also, if necessary, a terminator sequence, an enhancer sequence, a splicing signal sequence, a polyA addition signal sequence, a ribosome binding sequence (SD sequence), a selection marker gene, and the like, which can be used in a microorganism for gene introduction, can be ligated to a vector. Examples of a selection marker gene include, in addition to drug resistance genes such as an ampicillin resistance gene, a tetracycline resistance gene, a neomycin resistance gene, a kanamycin resistance gene, and a chloramphenicol resistance gene, genes involved in intracellular biosynthesis of nutrients, such as amino acids or nucleic acids, or genes encoding fluorescent proteins such as green fluorescent protein.

The above vector can be introduced into a microorganism by a method known by persons skilled in the art. Examples of such a method for introducing a vector into a microorganism include a calcium phosphate method, electroporation, a spheroplast method, a lithium acetate method, a conjugal transfer method, and a method using calcium ions.

Production of Aliphatic Polyester

A target aliphatic polyester oligomer can be produced by culturing a recombinant microorganism (obtained by introducing the above pct gene and PHA synthase gene into a host microorganism) in medium containing carbon sources, causing generation and accumulation of the aliphatic polyester oligomer in the culture product, and then recovering the aliphatic polyester oligomer. The recombinant microorganism synthesizes lactic acid from sugar through a sugar metabolic pathway, and then propionyl CoA transferase encoded by the pct gene converts lactic acid into lactic acid-CoA. Furthermore, in the recombinant microorganism, PHA synthase encoded by the PHA synthase gene synthesizes an aliphatic polyester oligomer comprising lactic acid as a constitutional unit using lactic-acid CoA as a substrate. The oligomer may be polylactic acid (homopolymer) comprising only lactic acid as a constitutional unit, or a lactic acid-based copolymer comprising lactic acid and hydroxyalkanoic acid other than lactic acid as constitutional units. Also, oligomers to be produced in medium are mainly dimers, trimers, tetramers, and pentamers. Here, the term "mainly" means that the above oligomers account for 50% or more, preferably 70% or more, and more preferably 90% or more of the aliphatic polyester components contained in the medium.

When polylactic acid (homopolymer) is synthesized, hydroxyalkanoic acid other than lactic acid is not added to the medium, or a biosynthetic pathway for hydroxyalkanoic acid other than lactic acid in the host microorganism is deleted. Meanwhile, when a lactic acid-based copolymer comprising lactic acid and hydroxyalkanoic acid other than lactic acid as constitutional units is synthesized, hydroxyalkanoic acid other than lactic acid may be added to the medium, or the biosynthetic pathway for hydroxyalkanoic acid other than lactic acid may be provided for the host microorganism.

In particular, the recombinant microorganism according to the present invention produces aliphatic polyester oligomers outside the cells without accumulating aliphatic polyester within the cells. The recombinant microorganism of the present invention accumulates aliphatic polyester outside the cells, so that there is no need to increase cell growth efficiency in order to improve aliphatic polyester productivity. Therefore, the recombinant microorganism according to the present invention can produce aliphatic polyester oligomers at high levels even if a medium containing nutrient components to a degree such that growth is barely possible is used. Therefore, the recombinant microorganism according to the present invention is used so that high aliphatic polyester oligomer productivity can be achieved at low cost.

On the other hand, in the case of a recombinant microorganism that accumulates aliphatic polyester within cells, a policy employed herein to improve aliphatic polyester productivity involves increasing the growth efficiency of the recombinant microorganism and thus increasing the microbiomass. In this case, a medium with a high nutritional value should be used for increasing the growth efficiency of such a recombinant microorganism, resulting in very high cost. Also, in the case of a recombinant microorganism that accumulates aliphatic polyester within cells, culture must be completed at relatively early phase of the accumulation of aliphatic polyester within cells.

In contrast, the recombinant microorganism according to the present invention produces aliphatic polyester oligomers outside the cells, so that culture can be continued over a long time period and aliphatic polyester oligomers can be produced. Particularly in the case of the recombinant microorganism according to the present invention, fed-batch culture is preferably performed, comprising removing a portion from the medium and adding additional medium or some of medium components while continuing culture.

Meanwhile, when the recombinant microorganism according to the present invention is cultured for production of aliphatic polyester oligomers, low-cost medium containing general carbon sources and the like, such as minimal medium, is preferably used, but examples are not particularly limited thereto. Examples of carbon sources include carbohydrates such as glucose, fructose, sucrose, and maltose. Also, substances associated with fats and oils having a carbon number of 4 or more can also be used as carbon sources. Examples of a substance associated with fats and oils having a carbon number of 4 or more include natural fats and oils such as corn oil, soybean oil, safflower oil, sunflower oil, olive oil, coconut oil, palm oil, rape-seed oil, fish oil, whale oil, pig oil, and beef tallow oil, fatty acids such as butanoic acid, pentanoic acid, hexanoic acid, octanoic acid, decanoic acid, lauric acid, oleic acid, palmitic acid, linolenic acid, linoleic acid, and myristic acid, or esters thereof, and alcohols such as octanol, lauryl alcohol, oleyl alcohol, and palmityl alcohol, or esters thereof.

Examples of nitrogen sources include, in addition to ammonia and ammonium salts such as ammonium chloride, ammonium sulfate, and ammonium phosphate, peptone, meat extract, yeast extract, and corn steep liquor. Examples of an inorganic material include monopotassium phosphate, dipotassium phosphate, magnesium phosphate, magnesium sulfate, and sodium chloride.

Culture is preferably performed under aerobic conditions such as general shaking culture within a temperature range of 25° C.-37° C. for preferably 48 hours or more after the expression of the above pct gene and PHA synthase gene. During culture, antibiotics such as kanamycin, ampicillin, or tetracycline may be added to the medium. When either one of or both of the above pct gene and PHA synthase gene are introduced under control of an inducible promoter, a factor for inducing transcription from the promoter is added to the medium, and then culture is preferably performed for at least 72 hours.

In particular, lactic acid oligomers are preferably produced by culturing recombinant *Escherichia coli* in which the above pct gene and PHA synthase gene have been introduced. This method is advantageous in production cost, since lactic acid oligomers can be produced without adding a monomer component (e.g., lactic acid) composing a target polymer to the medium.

In addition, an aliphatic polyester oligomer such as a lactic acid oligomer can be recovered by a method known by persons skilled in the art. For example, cells are collected from a culture solution by centrifugation so as to remove cell components, and thus an aliphatic polyester oligomer such as a lactic acid oligomer can be recovered from the medium after removal of the cells according to a conventional method. The thus recovered product can be confirmed to be an aliphatic polyester oligomer such as a lactic acid oligomer by a general method such as gas chromatography or a nuclear magnetic resonance method.

EXAMPLES

Hereafter, the present invention is described in greater detail with reference to the examples, although the technical scope of the present invention is not limited thereto.

Example 1

Evaluation of Various PHA Synthase Genes

In this Example, lactic acid oligomer productivity was evaluated for various PHA synthase genes when the genes had been expressed with a *Megasphaera elsdenii*-derived pct gene.

First, a pTV118N-M.E PCT vector for introduction of the *Megasphaera elsdenii*-derived pct gene was constructed. The *M. elsdenii* (ATCC17753) genome was obtained by a conventional method, and then the pct gene was obtained by a PCR method. As primers for amplification of a DNA fragment containing the *M. elsdenii*-derived pct gene, MePCTN: 5'-atgagaaaagtagaaatcattac-3'(SEQ ID NO: 19) and MePCTC:5'-ttatttttcagtcccatgggaccgtcctg-3'(SEQ ID NO: 20) were used. In addition, the nucleotide sequences of the primers were prepared with reference to the sequences disclosed in WO02/42418.

The pct gene was amplified from the genome under the following PCR conditions (enzyme KOD plus) (94° C. for 1 min)×1, (94° C. for 0.5 min, 50° C. for 0.5 min, 72° C. for 2 min)×30, and (94° C. for 2 min). The amplification fragment was introduced into a TOPO BluntII vector, and then sequencing was performed. As a result, the reported sequence had 97.8% homology with the nucleotide sequence, and only one portion thereof differed from the amino acid sequence.

The *M. elsdenii*-derived pct gene obtained as described above by PCR was inserted between EcoR 1 and Pst I of a pTV118N vector (Takara Bio Inc.), so that a pTV118N-M.E PCT expression plasmid was constructed.

Next, the PHA synthase genes examined in this Example are listed in Table 2. In Table 2, regarding No. 1 (*Rhodobacter sphaeroides*) and No. 4 (*Rhodospirillum rubrum*), a plurality of genes registered under different accession numbers have been discovered, so that a plurality of genes were examined.

TABLE 2

| No. | Strain | Accession No. | Class | Biological resource center | No. |
|---|---|---|---|---|---|
| 1 | Rhodobacter sphaeroides | YP354337 ABA79557 | I I | ATCC | BAA-808D |
| 2 | Azorhizobium caulinodans | | I | NBRC | 14845 |
| 3 | Rhizobium etli CFN 42 | | I | " | 15573 |
| 4 | Rhodospirillum rubrum | AAD53179 CAB65395 | I I | ATCC | 25903 |
| 5 | Colwellia psychrerythraea 34H | | I | " | BAA-681D |
| 6 | Chromobacterium violaceum | | I | " | 12472D |
| 7 | Pseudomonas sp. 61-3 | | II | JCM | 10015 |
| 8 | Hyphomonas neptunium | | II | NBRC | 14232 |
| 9 | Haloquadratum walsbyi | | III | JCM | 12895 |
| 10 | Haloarcula marismortui | | III | " | 8966 |
| 11 | Synechocystis sp. PCC6803 | | III | ATCC | 27184D |
| 12 | Alcanivorax borkumensis SK2 | | III | " | 700651 |
| 13 | Bacillus cereus | | IV | " | 14579D |
| 14 | Acinetobacter baumannii ATCC 17978 | | — | " | 17978 |
| 15 | Magnetospirillum magneticum AMB-1 | | — | ATCC | 700264 |
| 16 | Xanthomonas campestris pv. Campestris | | — | " | 33913D |
| 17 | Ralstonia eutropha H16 | | I | | |

In addition, in Table 2, Class I means that the PHA synthase gene has strong activity and has high substrate specificity, Class II means that the PHA synthase gene has low substrate specificity, and has weak activity, Class III means that the PHA synthase gene further requires the presence of phaE for PHA synthase reaction, and Class IV means that the PHA synthase gene further requires the presence of phaR for PHA synthase reaction.

DNA fragments containing 19 types of PHA synthase gene derived from 17 types of microorganism (shown in No. 1 to No. 17) were amplified by 1 cycle of PCR or 2 cycles of PCR. The DNA fragments were introduced into pTV188N vectors in which the *Megasphaera elsdenii*-derived pct gene had been introduced. Primers for 1st PCR designed for amplification of the DNA fragments are shown in Table 3 and Table 4.

TABLE 3

| No. | Strain name | phaC gene name for management | Primer name | Sequence | SEQ ID NO: |
|---|---|---|---|---|---|
| 1 | Rhodobacter sphaeroides | R. sphae-YP | RsphaeroidesF | TCAGCGTTGCAGGATGTAGG | SEQ ID NO: 21 |
| | | | RsphaeroidesR | TCCATGTCTGACATGAAGTGGAA | SEQ ID NO: 22 |
| | | R. sphae-ABA | Rhodobacter-fwd 2 | TGCGCCGCAGAAAATCAACC | SEQ ID NO: 23 |
| | | | Rhodobacter-rvs 2 | ACAAGTCAATATGGCAACCGAAGAG | SEQ ID NO: 24 |
| 2 | Azorhizobium aulinodans | A. cauli | Azorhizobium-fwd 3 | AGGAGATATACATATGGAGGCGTTCGCC | SEQ ID NO: 25 |
| | | | Azorhizobium-rvs 3 | AGATCCAACTCAGGACTTCTCGCGTACG | SEQ ID NO: 26 |
| 3 | Rhizobium etli CFN 42 | R. etil | Rhizobium-fwd 2 | TTTCTCGTTCGGTCACGATG | SEQ ID NO: 27 |
| | | | Rhizobium-rvs 2 | TCGCTGTTTCTTAGGATGTCTC | SEQ ID NO: 28 |

TABLE 3-continued

| No. | Strain name | phaC gene name for management | Primer name | Sequence | SEQ ID NO: |
|---|---|---|---|---|---|
| 4 | Rhodospirillum rubrum | R. rubru-AAD R. rubru-CAB | R. rubrumF R. rubrumR | CCGGGCTCGATGTTTACGAC GACAAGTGAGTCGCCCCTATG | SEQ ID NO: 29 SEQ ID NO: 30 |
| 5 | Colwellia psychrerythraea 34H | C. psych | ColwelliaF ColwelliaR | TTACGCTAGGGTAGAGGAAG ATGGAATCGAATGAGCAGAA | SEQ ID NO: 31 SEQ ID NO: 32 |
| 6 | Chromobacterium violaceum | C. viola | C. violaceumF C. violaceumR | GACAACGATTTGCACGTTTC ACGATTGCTACTTCCATGTC | SEQ ID NO: 33 SEQ ID NO: 34 |
| 7 | Pseudomonas sp. 61-3 | Ps61-3.C2 | P. sp. 61-3 (phaC2)-fwd 2 P. sp. 61-3 (phaC2)-rvs 2 | ATGGCTTGACGAAGGAGTGT GGGTTTTCATCCAGTCTTCTTGG | SEQ ID NO: 35 SEQ ID NO: 36 |
| 8 | Hyphomonas neptunium | H. neptu | | | |
| 9 | Haloquadratum walsbyi | H. walsb | HwalsbphaEC1stFwd HwalsbphaEC1stRvs | ATGAGCAATAATGCAAACGACCCCACAG GAATCCTGCTGTCCAGTTATTCGTTCAG | SEQ ID NO: 37 SEQ ID NO: 38 |
| 10 | Haloarcula marismortui | H. maris | HmarisphaEC1stFwd HmarisphaEC1stRvs HaloarculaPhaEF HaloarculaPhaER | GCCGCCGAGGTACTATTATGAG AAAGGGGCGCCGAATTACAG CGTAAGTACGACAGTCGGTT GTCATGTTCTCCAGCGTCTT | SEQ ID NO: 39 SEQ ID NO: 40 SEQ ID NO: 41 SEQ ID NO: 42 |

TABLE 4

| No. | Strain name | phaC gene name for management | Primer name | Sequence | SEQ ID NO: |
|---|---|---|---|---|---|
| 11 | Synechocystis sp. PCC6803 | S. sp. | SynecphaEC1stFwd SynecphaEC1stRvs | ATGGAATCGACAAATAAAACCTGGACAGA AAAATTTTCACTGTCGTTCCGATAGCC | SEQ ID NO: 43 SEQ ID NO: 44 |
| 12 | Alcanivorax borkumensis SK2 | A. borku-YP | A. borkumensisF A. borkumensisR | CATTTCCAGGAGTCGTTGTG TTGTGCGTAAATCCATTCCC | SEQ ID NO: 45 SEQ ID NO: 46 |
| 13 | Bacillus cereus | B. cereus | BcereusphaC1stFwd BcereusphaC1stRvs BcereusphaR1stFwd BcereusphaR1stRvs | ACCAGAAAATAAAAAATGATAAAGAAGGA AATCGACCAA TTAATTAGAACGCTCTTCA TTGAATTGTTTCAAAAACGAA TTGGTCGATTTCCTTCTTTTATCATTTTTT ATTTTCTGGT | SEQ ID NO: 47 SEQ ID NO: 48 SEQ ID NO: 49 SEQ ID NO: 50 |
| 14 | Acinetobacter baumannii ATCC 17978 | A. bauma | A. baumanniiF A. baumanniiR | AATGTTCCACAGGTACAGTC CCAGCCTAAGGTTTAACAGG | SEQ ID NO: 51 SEQ ID NO: 52 |
| 15 | Magnetospirillum magneticum AMB-1 | M. magne-BAE | M. magneticumF M. magneticumR | CACTTGAAGGACGGATCGCT TCGCTTACCCCTTCTGCAAC | SEQ ID NO: 53 SEQ ID NO: 54 |
| 16 | Xanthomonas campestris pv. Campestris | X. campe | X. campestrisF X. campestrisR | GGCAGGATCAGCAGATGGTTC GATGGGCACGATCAAACCCT | SEQ ID NO: 55 SEQ ID NO: 56 |
| 17 | Ralstonia eutropha H16 | R. eutro | | | |

Primers for 2nd PCR designed for amplification of the DNA fragments are shown in Table 5 and Table 6.

TABLE 5

| No. | Strain name | phaC gene name for management | Primer name | Sequence | SEQ ID NO: |
|---|---|---|---|---|---|
| 1 | Rhodobacter sphaeroides | R. sphae-YP | RYP3543372ndFwd RYP3543372ndRev | CCGGTTCGAATCTAGAAATAATTTTGTTTAACT TTAAGAAGGAGATATACATATGTCTGACATG GAACCAGGCGGAACCTGCAGAGATCCAACTCAG CGTTGCAG | SEQ ID NO: 57 SEQ ID NO: 58 |

TABLE 5 -continued

| No. | Strain name | phaC gene name for management | Primer name | Sequence | SEQ ID NO: |
|---|---|---|---|---|---|
| | | R. sphae-ABA | RABA795572ndFwd | CCGGTTCGAATCTAGAAATAATTTTGTTTAACTTTAAGAAGGAGATATACATATGGCAACCGAA | SEQ ID NO: 59 |
| | | | RABA795572ndRev | GAACCAGGCGGAACCTGCAGAGATCCAACTCAAGCCCCGCC | SEQ ID NO: 60 |
| 2 | Azorhizobium caulinodans | A. cauli | Azorhizo-fwd | TCGAATCTAGAAATAATTTTGTTTAACTTTAAGAAGGAGATATACATATGGAGGCGT | SEQ ID NO: 61 |
| | | | Azorhizo-rvs | GGAACCTGCAGAGATCCAACTCAGGACTTCTC | SEQ ID NO: 62 |
| 3 | Rhizobium etli CFN 42 | R. etli | Rhizo-fwd | TCGAATCTAGAAATAATTTTGTTTAACTTTAAGAAGGAGATATACATATGTACAACA | SEQ ID NO: 63 |
| | | | Rhizo-rvs | GGAACCTGCAGAGATCCAACTCAGGTGCGTT | SEQ ID NO: 64 |
| 4 | Rhodospirillum rubrum | R. rubru-AAD | RrubruAAD2ndFwd | CCGGTTCGAATCTAGAAATAATTTTGTTTAACTTTAAGAAGGAGATATACATATGTTACGACA | SEQ ID NO: 65 |
| | | | RrubruAAD2ndRvs | GAACCAGGCGGAACCTGCAGAGATCCAACTCAGATCCTAAC | SEQ ID NO: 66 |
| | | R. rubru-CAB | Rhodospirillum-fwd | CCGGTTCGAATCTAGAAATAATTTTGTTTAACTTTAAGAAGGAGATATACATATGGCCAATCAG | SEQ ID NO: 67 |
| | | | Rhodospirillum-rvs | CAGGCGGAACCTGCAGAGATCCAACTCACGTAATCGC | SEQ ID NO: 68 |
| 5 | Cotwellia psychretythraea 34H | C. psych | Colwellia2ndFwd | CCGGTTCGAATCTAGAAATAATTTTGTTTAACTTTAAGAAGGAGATATACATATGGAATCGAAT | SEQ ID NO: 69 |
| | | | Colwellia2ndRev | GAACCAGGCGGAACCTGCAGAGATCCAACCTAAATACGCTT | SEQ ID NO: 70 |

TABLE 6

| No. | Strain name | phaC gene name for management | Primer name | Sequence | SEQ ID NO: |
|---|---|---|---|---|---|
| 6 | Chromobacterium violaceum | C. viola | CviolaphaC2ndFwd | CCGGTTCGAATCTAGAAATAATTTTGTTTAACTTTAAGAAGGAGATATACATATGCAGCAGTTC | SEQ ID NO: 71 |
| | | | CviolaphaC2ndRvs | GAACCAGGCGGAACCTGCAGAGATCCAACTCATTGCAGGCT | SEQ ID NO: 72 |
| 7 | Pseudomonas sp. 61-3 | Ps61-3.C2 | PspC22ndFwd | CCGGTTCGAATCTAGAAATAATTTTGTTTAACTTTAAGAAGGAGATATACATATGAGAGAGAAA | SEQ ID NO: 73 |
| | | | PspC22ndRvs | GAACCAGGCGGAACCTGCAGAGATCCAACTCAGCGCACGCG | SEQ ID NO: 74 |
| 8 | Hyphomonas neptunium | H. neptu | Hypho-fwd | TCGAATCTAGAAATAATTTTGTTTAACTTTAAGAAGGAGATATACATATGACGTCAC | SEQ ID NO: 75 |
| | | | Hypho-rvs | GGAACCTGCAGAGATCCAACCTAGTCGTT | SEQ ID NO: 76 |
| 9 | Haloquadratum walsbyi | H. walsb | HwalsbphaEC2ndFwd | CCGGTTCGAATCTAGAAATAATTTTGTTTAACTTTAAGAAGGAGATATACATATGAGCAATAAT | SEQ ID NO: 77 |
| | | | HwalsbphaEC2ndRvs | GAACCAGGCGGAACCTGCAGAGATCCAACCTATTTGATCAA | SEQ ID NO: 78 |
| 10 | Haloarcula marismortui | H. maris | HmarisphaEC2ndFwd | CCGGTTCGAATCTAGAAATAATTTTGTTTAACTTTAAGAAGGAGATATACATATGAGTAATACA | SEQ ID NO: 79 |
| | | | HmarisphaEC2ndRvs | GAACCAGGCGGAACCTGCAGAGATCCAACTTACAGTTGATC | SEQ ID NO: 80 |
| 11 | Synechocystis sp. PCC6803 | S. sp. | SynecphaEC2ndFwd | CCGGTTCGAATCTAGAAATAATTTTGTTTAACTTTAAGAAGGAGATATACATATGGAATCGACA | SEQ ID NO: 81 |
| | | | SynecphaEC2ndRvs | GAACCAGGCGGAACCTGCAGAGATCCAACTCACTGTCGTTC | SEQ ID NO: 82 |
| 12 | Alcanivorax borkumensis SK2 | A. borku-YP | Aborku2ndFwd | CCGGTTCGAATCTAGAAATAATTTTGTTTAACTTTAAGAAGGAGATATACATATGTGGATGCTA | SEQ ID NO: 83 |
| | | | Aborku2ndRvs | GAACCAGGCGGAACCTGCAGAGATCCAACCTATGCTGAGCG | SEQ ID NO: 84 |
| 13 | Bacillus cereus | B. cereus | BcereusphaRC2ndFwd | CCGGTTCGAATCTAGAAATAATTTTGTTTAACTTTAAGAAGGAGATATACATATGAATTGTTTC | SEQ ID NO: 85 |
| | | | BcereusphaRC2ndRvs | GAACCAGGCGGAACCTGCAGAGATCCAACTTAATTAGAACG | SEQ ID NO: 86 |

TABLE 6 -continued

| No. | Strain name | phaC gene name for management | Primer name | Sequence | SEQ ID NO: |
|---|---|---|---|---|---|
| 14 | *Acinetobacter baumannii* ATCC 17978 | A. bauma | Abauma2ndFwd | CCGGTTCGAATCTAGAAATAATTTTGTTTAAC TTTAAGAAGGAGATATACATATGCTCTCCAAT | SEQ ID NO: 87 |
|  |  |  | Abauma2ndRvs | GAACCAGGCGGAACCTGCAGAGATCCAACTTA ATCTGAACG | SEQ ID NO: 88 |
| 15 | *Magnetospirillum magneticum* AMB-1 | M. magne-BAE | Mmagne2ndFwd | CCGGTTCGAATCTAGAAATAATTTTGTTTAACT TTAAGAAGGAGATATACATATGGCGGAGGCGG | SEQ ID NO: 89 |
|  |  |  | Mmagne2ndRvs | GAACCAGGCGGAACCTGCAGAGATCCAACCTAA GTGCCTGC | SEQ ID NO: 90 |
| 16 | *Xanthomonas campestris* pv. *Campestris* | X. campe | Xanthomonas2ndFwd | CCGGTTCGAATCTAGAAATAATTTTGTTTAAC TTTAAGAAGGAGATATACATTTGATGGAACTG | SEQ ID NO: 91 |
|  |  |  | Xanthomonas2ndRev | GAACCAGGCGGAACCTGCAGAGATCCAACTCA TCGGCGCGC | SEQ ID NO: 92 |
| 17 | *Ralstonia eutropha* H16 | R. eutro | Reutro2ndfwd | CCGGTTCGAATCTAGAAATAATTTTGTTTAAC TTTAAGAAGGAGATATACATATGGCGACCGGC | SEQ ID NO: 93 |
|  |  |  | Reutro2ndrvs | GAACCAGGCGGAACCTGCAGAGATCCAACTCA TGCCTTGGC | SEQ ID NO: 94 |

Also, conditions for PCR using these primers are shown in Table 7 and Table 8.

TABLE 7

| № | phaC gene name for management | 1st | | 2nd | |
|---|---|---|---|---|---|
| | | Composition of reaction solution | Temperature conditions | Composition of reaction solution | Temperature conditions |
| 1 | R.sphae-YP | A | 94° C. for 2 min.→94° C. for 15 sec., 55° C. for 30 sec., 68° C. for 2 min. × 30 cycles→68° C. for 5 min. | E | 94° C. for 2 min.→94° C. for 15 sec., 50° C. for 30 sec., 68° C. for 2 min. × 5 cycles→94° C. for 15 sec., 60° C. for 30 sec., 68° C. for 2 min. × 30 cycles→68° C. for 5 min. |
| | R.sphae-ABA | ↑ | ↑ | ↑ | 94° C. for 2 min.→94° C. for 15 sec., 50° C. for 30 sec., 68° C. for 2 min. × 5 cycles→94° C. for 15 sec., 60° C. for 30 sec., 68° C. for 2 min. × 30 cycles→68° C. for 5 min. |
| 2 | A.cauli | | | F | 94° C. for 2 min.→94° C. for 15 sec., 53° C. for 30 sec., 68° C. for 2 min. × 5 cycles→94° C. for 15 sec., 60° C. for 30 sec., 68° C. for 2 min. × 30 cycles→68° C. for 5 min. |
| 3 | R.etil | B | | ↑ | 94° C. for 2 min.→94° C. for 15 sec., 52° C. for 30 sec., 68° C. for 2 min. × 5 cycles→94° C. for 15 sec., 60° C. for 30 sec., 68° C. for 2 min. × 30 cycles→68° C. for 5 min. |
| 4 | R.rubru-AAD | A | | | 94° C. for 2 min.→94° C. for 15 sec., 45° C. for 30 sec., 68° C. for 2 min. 20 sec. × 5 cycles→94° C. for 15 sec., 55° C. for 30 sec., 68° C. for 2 min. 20 sec. × 30 cycles→68° C. for 5 min. |
| | R.rubru-CAB | | | A | 94° C. for 2 min.→94° C. for 15 sec., 50° C. for 30 sec., 68° C. for 2 min. × 5 cycles→94° C. for 15 sec., 60° C. for 30 sec., 68° C. for 2 min. × 30 cycles→68° C. for 5 min. |
| 5 | C.psych | A | 94° C. for 2 min.→94° C. for 15 sec., 55° C. for 30 sec., 68° C. for 2 min. × 30 cycles→68° C. for 5 min. | E | 94° C. for 2 min.→94° C. for 15 sec., 50° C. for 30 sec., 68° C. for 2 min. × 5 cycles→94° C. for 15 sec., 60° C. for 30 sec., 68° C. for 2 min. × 30 cycles→68° C. for 5 min. |
| 6 | C.viola | ↑ | ↑ | F | 94° C. for 2 min.→94° C. for 15 sec., 50° C. for 30 sec., 68° C. for 2 min. 20 min. × 5 cycles→94° C. for 15 sec., 60° C. for 30 sec., 68° C. for 2 min. 20 min. × 30 cycles→68° C. for 5 min. |
| 7 | Ps61-3.C2 | B | | ↑ | ↑ |
| 8 | H.neptu | | | C | 94° C. for 2 min.→94° C. for 15 sec., 55° C. for 30 sec., 68° C. for 2 min. × 30 cycles→68° C. for 5 min. |
| 9 | H.walsb | A | 94° C. for 2 min.→94° C. for 15 sec., 52° C. for 30 sec., 68° C. for 2 min. 15 sec. × 30 cycle→68° C. for 5 min. | E | 94° C. for 2 min.→94° C. for 15 sec., 50° C. for 30 sec., 68° C. for 2 min. 10 min. × 5 cycles→94° C. for 15 sec., 60° C. for 30 sec., 68° C. for 2 min. 20 min. × 30 cycles→68° C. for 5 min. |
| 10 | H.maris | ↑ | ↑ | ↑ | ↑ |
| 11 | S.sp. | | | | |

TABLE 8

| № | phaC gene name for management | 1st Composition of reaction solution | 1st Temperature conditions | 2nd Composition of reaction solution | 2nd Temperature conditions |
|---|---|---|---|---|---|
| 12 | A.borku-YP | A | 94° C. for 2 min.→94° C. for 15 sec., 45° C. for 30 sec., 68° C. for 1 min. 30 sec. × 30 cycles→68° C. for 5 min. | F | 94° C. for 2 min.→94° C. for 15 sec., 50° C. for 30 sec., 68° C. for 1 min. 30 sec. × 5 cycles→94° C. for 15 sec., 60° C. for 30 sec., 68° C. for 1 min. 30 sec. × 30 cycles→68° C. for 5 min. |
| 13 | B.cereus | ↑ | 94° C. for 2 min.→94° C. for 15 sec., 45° C. for 30 sec., 68° C. for 1 min. 10 sec. × 30 cycles→68° C. for 5 min. | G | 94° C. for 2 min.→94° C. for 15 sec., 52° C. for 30 sec., 68° C. for 1 min. 10 sec. × 20 cycles→68° C. for 5 min. |
| 14 | A.bauma | | 94° C. for 2 min.→94° C. for 15 sec., 41.5° C. for 30 sec., 68° C. for 1 min. 30 sec. × 30 cycles→68° C. for 5 min. | H | 94° C. for 2 min.→94° C. for 15 sec., 50° C. for 30 sec., 68° C. for 2 min. × 5 cycles→94° C. for 15 sec., 60° C. for 30 sec., 68° C. for 2 min. × 30 cycles→68° C. for 5 min. |
| 15 | M.magne-BAE | | 94° C. for 2 min.→94° C. for 15 sec., 45° C. for 30 sec., 68° C. for 1 min. 30 sec. × 30 cycles→68° C. for 5 min. | ↑ | ↑ |
| 16 | X.campe | | ↑ | | |
| 17 | R.eutro | | | D | 94° C. for 1 min.→98° C. for 10 sec., 52° C. for 30 sec., 72° C. for 1 min. 55 sec. × 5 cycles→98° C. for 10 sec., 62° C. for 30 sec., 72° C. for 1 min. 55 sec. × 30 cycles→68° C. for 5 min. |

In addition, the compositions A to H of reaction solutions under the reaction conditions shown in Table 7 and Table 8 are shown in Table 9.

TABLE 9

Composition A of reaction solution

5 µl 10 × Buffer for KOD-Plus Ver.2 (final 1 ×)
5 µl 2.5 mM dNTPs (final 0.25 mM each)
2 µl 25 mM MgSO4 (final 1.5 mM)
1.5 µl PrimerF(10 pmol/µ) (final 0.3 µM)
1.5 µl PrimerR(10 pmol/µ) (final 0.3 µM)
10~200 ng templateDNA genome
1 µl KOD-Plus(1 U/µl) (final 1U/50 µl)
sterile deionaized water up to 50 µl Composition B of reaction solution 5 µl 10 × Buffer for KOD-Plus Ver.2 (final 1 ×)
5 µl 2 mM dNTPs (final 0.2 mM each)
2 µl 25 mM MgSO4 (final 1.5 mM)
1.5 µl PrimerF(10 pmol/µ) (final 0.3 µM)
1.5 µl PrimerR(10 pmol/µ) (final 0.3 µM)
10~200 ng templateDNA genome
1 µl KOD-P/lus-(1 U/µl) (final 1U/50 µl)
sterile deionaized water up to 50 µl Composition C of reaction solution 5 µl 10 × Buffer for KOD-Plus Ver.2 (final 1 ×)
5 µl 2 mM dNTPs (final 0.2 mM each)
2 µl 25 mM MgSO4 (final 1.5 mM)
2 µl PrimerF(10 pmol/µ) (final 0.3 µM)
2 µl PrimerR(10 pmol/µ) (final 0.3 µM)
10~200 ng templateDNA genome
1 µl KOD-Plus(1 U/µl) (final 1U/50 µl)
sterile deionaized water up to 50 µl Composition D of reaction solution 5 µl 10 × Pyrobest Buffer II (final 1 ×)
5 µl 2.5 mM dNTPs (final 0.25 mM each)
1.5 µl PrimerF(10 pmol/µ) (final 0.3 µM)
1.5 µl PrimerR(10 pmol/µ) (final 0.3 µM)

TABLE 9-continued

37 µg template eutropha/pet plasmid
1 µl Pyrobest(1 U/µl) (final 1U/50 µl)
sterile deionized water up to 50 µl
Composition E of reaction solution 5 µl 10 × Buffer for KOD-Plus Ver.2 (final 1 ×)
5 µl 2.5 mM dNTPs (final 0.25 mM each)
2 µl 25 mM MgSO4 (final 1.5 mM)
1.5 µl PrimerF(10 pmol/µ) (final 0.3 µM)
1.5 µl PrimerR(10 pmol/µ) (final 0.3 µM)
1 µl templateDNA(1stPCRproduct, diluted 1/500 after purification)
1 µl KOD-Plus(1 U/µl) (final 1U/50 µl)
sterile deionized water up to 50 µl Composition F of reaction solution 5 µl 10 × Buffer for KOD-Plus Ver.2 (final 1 ×)
5 µl 2.5 mM dNTPs (final 0.25 mM each)
2 µl 25 mM MgSO4 (final 1.5 mM)
1.5 µl PrimerF(10 pmol/µ) (final 0.3 µM)
1.5 µl PrimerR(10 pmol/µ) (final 0.3 µM)
1 µl templateDNA(1stPCRproduct, diluted 1/1000 after purification)
1 µl KOD-Plus(1 U/µl) (final 1U/50 µl)
sterile deionized water up to 50 µl Composition G of reaction solution (without primers)

5 µl 10 × Buffer for KOD-Plus Ver.2 (final 1 ×)
5 µl 2.5 mM dNTPs (final 0.25 mM each)
2 µl 25 mM MgSO4 (final 1.5 mM)
1 µl templateDNA(phaR 1stPCRproduct, purified without dilution)
1 µl KOD-Plus(1 U/µl) (final 1U/50 µl)
sterile deionized water up to 50 µl Composition H of reaction solution 5 µl 10 × Buffer for KOD-Plus Ver.2 (final 1 ×)
5 µl 2.5 mM dNTPs (final 0.25 mM each)
2 µl 25 mM MgSO4 (final 1.5 mM)
1.5 µl PrimerF(10 pmol/µ) (final 0.3 µM)
1.5 µl PrimerR(10 pmol/µ) (final 0.3 µM)

TABLE 9-continued

1 μl Left PCR reaction solution (without purification)
1 μl KOD-Plus(1 U/μl) (final 1U/50 μl)
sterile deionaized water up to 50 μl
Composition G' of reaction solution 5 μl 10 x Buffer for KOD-Plus Ver.2 (final 1 x)
5 μl 2.5 mM dNTPs (final 0.25 mM each)
2 μl 25 mM MgSO4 (final 1.5 mM)
1.5 μl PrimerF(10 pmol/μ) (final 0.3 μM)
1.5 μl PrimerR(10 pmol/μ) (final 0.3 μM)
1 μl Left PCR reaction solution (without purification)
1 μl KOD-Plus(1 U/μl) (final 1U/50 μl)
sterile deionaized water up to 50 μl In addition, regarding No. 13 (pha gene), 2 genes (phaR and phaC) were present sandwiching other genes. Hence, the genes were separately cloned by 1$^{st}$ PCR and then the resultants were linked to form a sequence by 2nd PCR. Furthermore, for ligation to a vector, PCR was performed again (composition of reaction solution: G'; temperature conditions: 94° C. for 2 minutes→94° C. for 15 seconds, 50° C. for 30 seconds, 68° C. for 1 minute and 40 seconds×5 cycles→94° C. for 15 seconds, 60° C. for 30 seconds, 68° C. for 1 minute and 40 seconds×30 cycles→68° C. for 5 minutes).

Also, for Nos. 2, 3, and 8 (phaC genes), each of the purified 2" PCR products and a pTV118N-PCT-C1 vector were digested with restriction enzymes (Xba I and Pst I (Takara Bio Inc.)) and then loaded on agarose gel (0.8%, TAE) together with 10× loading buffer (Takara Bio Inc.), followed by separation by electrophoresis, excision, and purification. Purification was performed using a MinElute Gel Extraction Kit (QIAGEN) according to protocols. Ligation and transformation were each performed according to protocols using Ligation-Convenience Kit (Nippon Gene Co., Ltd.) and ECOS competent *E. coli* JM109 (Nippon Gene Co., Ltd.). The thus obtained transformant was cultured in 2 ml of LB-Amp medium, and then plasmid extraction was performed using a QIAprep Spin Miniprep Kit (QIAGEN). Sequence reaction was performed using a Big Dye Terminator v3.1 Cycle Sequencing Kit (Applied Biosystems), and then the sequences were confirmed using a DNA sequencer 3100 Genetic Analyzer (Applied Biosystems).

Furthermore, for Nos. 1, 4-7, and 9-17 (phaC genes), ligation was performed using an In-Fusion 2.0 Dry-Down PCR Cloning Kit (Clontech Laboratories) in view of simpleness for experimental protocols or the presence of a Pst I site within each phaC gene (Nos. 4, 6, 10, and 12). The other portions were subjected to procedures similar to the above.

Various phaC genes obtained above were each incorporated into pTV118N-M.E PCT, so that a vector was obtained. The thus obtained vector was introduced into *Escherichia coli* W3110 competent cells, so that recombinant *Escherichia coli* expressing a *Megasphaera elsdenii*-derived pct gene and any one of the above PHA synthase genes was prepared. The thus obtained recombinant *Escherichia coli* was plated on LB medium containing ampicillin, followed by static culture overnight at 37° C. The thus obtained colonies were plated on 2 mL of LB liquid medium containing ampicillin, and then shake culture was performed within a test tube at 37° C. until OD600 reached 0.6 to 1.0. Thus, the resultant was used as a pre-culture solution.

Next, the pre-culture solution (2 mL) was added to 200 mL of M9 medium containing ampicillin, 2% glucose, and 0.1 mM IPTG, and then rotation culture was performed using a 500-mL buffled Erlenmeyer flask at 30° C. for 48 hours at 130 rpm.

After completion of culture, the culture solution was transferred to a 50-mL corning tube, cells were collected under conditions of 3000 rpm and 15 minutes, and thus a supernatant was obtained. The culture solution (200 μl) was transferred to a pressure-proof reaction tube, and then 1.6 mL of chloroform was added. Furthermore, 1.6 mL of a mixed solution of methanol and sulfuric acid (methanol:sulfuric acid=17:3 (volume ratio)) was added, followed by 3 hours of refluxing within a water bath set at 95° C. Subsequently, the pressure-proof reaction tube was removed and then cooled to room temperature. The solution within the tube was then transferred to a test tube. Ultrapure water (0.8 mL) was further added to the test tube, the solution was mixed using a vortex, and then left to stand. After the solution was sufficiently left to stand, the chloroform phase of the lower layer was fractionated using a Pasteur pipette. The chloroform phase was filtered with a 0.2-μm mesh organic solvent-resistant filter, the resultant was transferred to a vial bottle for GC-MS, and thus a sample for analysis was obtained.

As a GC-MS apparatus, HP6890/5973 (Hewlett-Packard Company) was used. As a column, BD-1 122-1063 (inner diameter: 0.25 mm; length: 60 m; membrane thickness: 1 μm (Agilent Technology)) was used. Temperature increase conditions employed herein comprise maintaining the temperature at 120° C. for 5 minutes, increasing the temperature at 10° C./min to 200° C., increasing the temperature at 20° C./min to 300° C., and then maintaining the temperature for 8 minutes.

FIG. 1 shows the results of measuring by GC-MS the amounts of lactic acid polymer produced. As shown in FIG. 1, it was revealed that many recombinant *Escherichia coli* cells produced lactic acid polymer in media. In particular, recombinant *Escherichia coli* in which an *Alcanivorax borkumensis*-derived PHA synthase gene (No. 12), a *Hyphomonas neptunium*-derived PHA synthase gene (No. 8), a *Rhodobacter sphaeroides*-derived PHA synthase gene (No. 1), a *Rhizobium etli*-derived PHA synthase gene (No. 3), a *Pseudomonas* sp.-derived PHA synthase gene (No. 7), or a *Haloarcula marismortui*-derived PHA synthase gene (No. 10) had been introduced were revealed to have good lactic acid oligomer productivity.

Meanwhile, Table 10 shows the results of examining lactic acid oligomer productivity using a kit for component determination by an enzyme method, F-Kit series (Roche Diagnostics).

TABLE 10

| Gene | Color development |
| --- | --- |
| pTV118N | − |
| PCT | − |
| No. 1-YP | + |
| No. 1-ABA | ± |
| No. 2 | ± |
| No. 3 | + |
| No. 4-AAD | ± |
| No. 4-CAB | ± |
| No. 5 | ± |
| No. 6 | ± |
| No. 7 | + |
| No. 8 | + |
| No. 9 | ± |
| No. 10 | + |
| No. 11 | ± |
| No. 12 | + |
| No. 13 | ± |
| No. 14 | ± |
| No. 15 | ± |
| No. 16 | ± |
| No. 17 | ± |

As shown in Table 10, it was revealed that recombinant *Escherichia coli* in which the *Alcanivorax borkumensis*-derived PHA synthase gene (No. 12), the *Hyphomonas neptunium*-derived PHA synthase gene (No. 8), the *Rhodobacter*

*sphaeroides*-derived PHA synthase gene (No. 1), the *Rhizobium etli*-derived PHA synthase gene (No. 3), the *Pseudomonas* sp.-derived PHA synthase gene (No. 7), or the *Haloarcula marismortui*-derived PHA synthase gene (No. 10) had been introduced had good lactic acid oligomer productivity.

Based on the results shown in FIG. 1 and Table 10, the culture solution of recombinant *Escherichia coli* (in which any one of the *Alcanivorax borkumensis*-derived PHA synthase gene (No. 12), the *Hyphomonas neptunium*-derived PHA synthase gene (No. 8), the *Rhodobacter sphaeroides*-derived PHA synthase gene (No. 1), the *Rhizobium etli*-derived PHA synthase gene (No. 3), the *Pseudomonas* sp.-derived PHA synthase gene (No. 7), and the *Haloarcula marismortui*-derived PHA synthase gene (No. 10) had been introduced) revealed to have good lactic acid oligomer productivity in a culture solution was examined using an electrospray ionization mass spectroscope (ESI-MS system) to find the degree of polymerization of a lactic acid oligomer contained therein. Samples for measurement were each prepared by adding methanol to a culture solution, in an amount equivalent thereto.

As an ESI-MS system, Q-TOF (Micromass) was used. The ionization method was electrospray ionization, and the ionization mode was negative ion mode. The capillary voltage was 3200 V, the cone voltage was 30 V, the ion source temperature was 80° C., and the desolvation temperature was 120° C. The method used for introducing a sample was an infusion method (direct introduction). Each sample was introduced at 5 µl/min. Also, the number of instances of integration (integration frequency) was 100 times.

The results of measuring lactic acid dimer, trimer, tetramer, and pentamer levels in medium for recombinant *Escherichia coli* in which any one of the *Hyphomonas neptunium*-derived PHA synthase gene (No. 8), the *Rhodobacter sphaeroides*-derived PHA synthase gene (No. 1), the *Rhizobium etli*-derived PHA synthase gene (No. 3), the *Pseudomonas* sp.-derived PHA synthase gene (No. 7), and the *Haloarcula marismortui*-derived PHA synthase gene (No. 10) had been introduced are shown in FIG. 2, FIG. 3, FIG. 4, and FIG. 5, respectively.

Furthermore, the results of measuring lactic acid dimer, trimer, tetramer, pentamer, hexamer, and heptamer levels in medium for recombinant *Escherichia coli* in which the *Alcanivorax borkumensis*-derived PHA synthase gene (No. 12) had been introduced are shown in FIG. 6, FIG. 7, FIG. 8, FIG. 9, FIG. 10, and FIG. 11, respectively. In addition, FIG. 6 to FIG. 11 show the result (top row) of measuring a culture solution, the result (middle row) of measuring a sample prepared by adding a lactic acid oligomer preparation (to be measured) to the culture solution, and the result (bottom row) of measuring a lactic acid oligomer preparation (to be measured).

Example 2

In this Example, differences in lactic acid oligomer productivity depending on medium type were examined using recombinant *Escherichia coli* prepared in Example 1 through introduction of the *Alcanivorax borkumensis*-derived PHA synthase gene (No. 12).

In this Example, a lactic acid oligomer was produced in medium in a manner similar to that in Example 1 except for using M9 medium (hereinafter, M9YE medium) prepared as medium with a high nutritional value by adding an yeast extract and M9 medium as medium with a low nutritional value. The lactic acid oligomer quantity was determined by GC-MS. In addition, M9 medium contained 6.8 g of $Na_2HPO_4$, 3 g of $KH_2PO_4$, 0.5 g of NaCl, and 1 g of $NH_4Cl$ per liter thereof, and further contained 2 ml of 1M $MgSO_4$, 100 ml of 20% glucose, 1 ml of 1% thiamine, and 0.1 ml of 1M $CaCl_2$.

A yeast extract (1 g) was added to 1 l of each M9YE medium.

Figure 12:
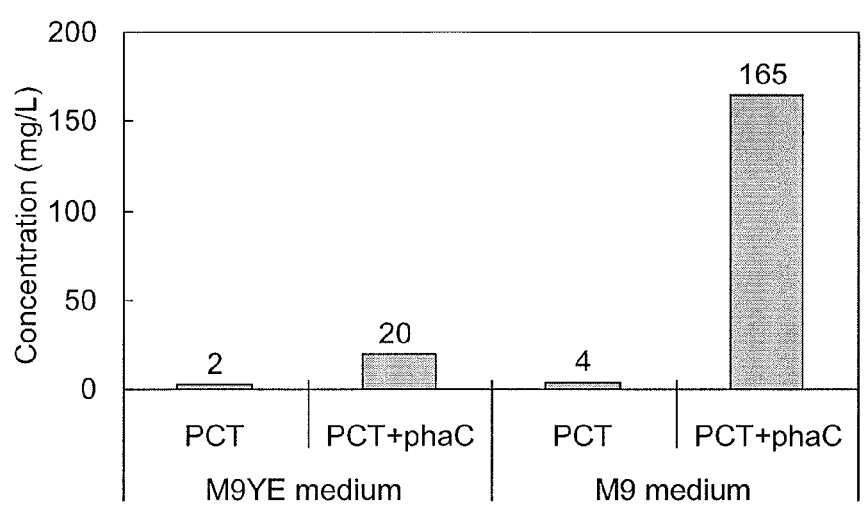
FIG. 12 is a characteristic diagram showing the results of examining differences in lactic acid oligomer productivity depending on medium types using recombinant *Escherichia coli* in which the *Alcanivorax borkumensis*-derived PHA synthase gene (No. 12) was introduced.

FIG. 12 shows the results of determining the lactic acid oligomer quantity by GC-MS. As shown in FIG. 12, recombinant *Escherichia coli* used herein exhibited characteristics such that it had higher lactic acid oligomer productivity when medium with a low nutritional value had been used. It could be determined on the basis of the results of this Example that increased lactic acid oligomer productivity was similarly obtained in the cases of the other recombinant *Escherichia coli* cells prepared in Example 1, even when medium with a low nutritional value such as M9 medium had been used. Therefore, it was revealed that the lactic acid oligomer can be produced at low cost through the use of recombinant *Escherichia coli* prepared in Example 1.

Example 3

In this Example, the relationship between the time for culture and lactic acid oligomer productivity was examined using recombinant *Escherichia coli* prepared in Example 1 through introduction of the *Alcanivorax borkumensis*-derived PHA synthase gene (No. 12).

Figure 13:
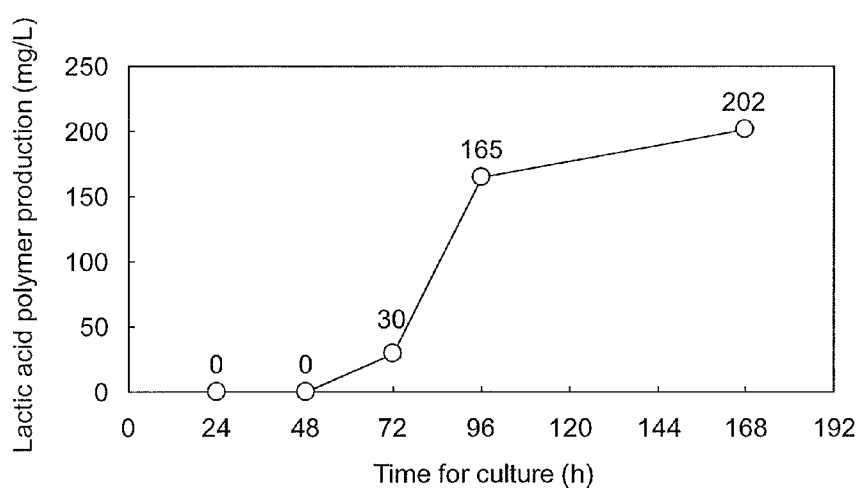
FIG. 13 is a characteristic diagram showing the results of examining a relationship between the time for culture and lactic acid oligomer productivity using recombinant *Escherichia coli* in which the *Alcanivorax borkumensis*-derived PHA synthase gene (No. 12) was introduced.

In this Example, a lactic acid oligomer was produced in medium in a manner similar to that in Example 1 except for continuing culture for 192 hours, and then the lactic acid oligomer quantity was determined by GC-MS. FIG. 13 shows the results of sampling culture solutions at stages of 24 hours, 48 hours, 76 hours, 96 hours, and 168 hours after the start of culture, and then determining the lactic acid oligomer quantity by GC-MS. As shown in FIG. 13, recombinant *Escherichia coli* used herein was observed to initiate the production of the lactic acid oligomer in a culture solution at 48 hours after the start of culture. The production of the lactic acid oligomer was observed to drastically increase at and after 72 hours (after the start of culture). Also, recombinant *Escherichia coli* used herein was observed to maintain its high level of production even after 168 hours after the start of culture.

It was similarly concluded on the basis of the results of this Example that the other recombinant *Escherichia coli* cells prepared in Example 1 maintain lactic acid oligomer productivity at high levels over long periods of time, for example. Therefore, it was revealed that a lactic acid oligomer can be produced at low cost through the use of recombinant *Escherichia coli* prepared in Example 1.

All publications, patents, and patent applications cited herein are incorporated herein by reference in their entirety.

The invention claimed is:

1. A recombinant microorganism, which is prepared by introducing: a gene encoding a protein having activity of converting lactic acid to lactic-acid CoA; and one or more genes encoding a protein(s) having activity of synthesizing polyhydroxyalkanoate using hydroxyacyl CoA as a substrate into a host microorganism, wherein one of said one or more genes that encode a protein having activity of synthesizing polyhydroxyalkanoate using hydroxyacyl CoA as a substrate is an *Alcanivorax borkumensis*-derived gene encoding a protein that comprises the amino acid sequence shown in SEQ ID NO: 6.

2. The recombinant microorganism according to claim 1, wherein the host microorganism is *Escherichia coli*.

* * * * *